United States Patent
Maeda et al.

(10) Patent No.: US 9,340,615 B2
(45) Date of Patent: May 17, 2016

(54) ANTI-AXL ANTIBODY

(75) Inventors: Atsuhiko Maeda, Shizuoka (JP);
Hajime Miyamoto, Kanagawa (JP);
Taichi Kuramochi, Shizuoka (JP);
Atsushi Matsuo, Shizuoka (JP);
Tomoyuki Igawa, Shizuoka (JP);
Hirotake Shiraiwa, Shizuoka (JP);
Hiroyuki Tsunoda, Shizuoka (JP);
Tatsuhiko Tachibana, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/320,317

(22) PCT Filed: May 14, 2010

(86) PCT No.: PCT/JP2010/058166
§ 371 (c)(1),
(2), (4) Date: Feb. 1, 2012

(87) PCT Pub. No.: WO2010/131733
PCT Pub. Date: Nov. 18, 2010

(65) Prior Publication Data
US 2012/0121587 A1    May 17, 2012

(30) Foreign Application Priority Data
May 15, 2009  (JP) ................................. 2009-118725

(51) Int. Cl.
C07K 16/00    (2006.01)
C07K 16/28    (2006.01)
C07K 16/30    (2006.01)
A61K 39/00    (2006.01)

(52) U.S. Cl.
CPC ........... *C07K 16/2863* (2013.01); *C07K 16/303* (2013.01); *A61K 2039/505* (2013.01); *C07K 2317/24* (2013.01); *C07K 2317/30* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,322,678 A | 6/1994 | Morgan et al. |
| 5,468,634 A | 11/1995 | Liu |
| 5,639,641 A | 6/1997 | Pedersen et al. |
| 5,670,373 A | 9/1997 | Kishimoto |
| 5,709,858 A | 1/1998 | Godowski et al. |
| 5,891,996 A | 4/1999 | Mateo de Acosta del Rio et al. |
| 6,329,511 B1 | 12/2001 | Vasquez et al. |
| 6,677,436 B1 | 1/2004 | Sato et al. |
| 6,723,319 B1 | 4/2004 | Ito et al. |
| 6,913,747 B1 | 7/2005 | Co et al. |
| 7,122,637 B2 | 10/2006 | Presta |
| 7,217,797 B2 | 5/2007 | Hinton et al. |
| 7,276,585 B2 | 10/2007 | Lazar et al. |
| 9,096,651 B2 | 8/2015 | Igawa et al. |
| 9,175,091 B2 | 11/2015 | Kitazawa et al. |
| 9,228,017 B2 | 1/2016 | Igawa et al. |
| 2001/0001663 A1 | 5/2001 | Kishimoto et al. |
| 2002/0187150 A1 | 12/2002 | Mihara et al. |
| 2003/0114398 A1 | 6/2003 | Chatterjee et al. |
| 2004/0071706 A1 | 4/2004 | Ito et al. |
| 2004/0081651 A1 | 4/2004 | Karpusas et al. |
| 2005/0084906 A1 | 4/2005 | Goetsch et al. |
| 2005/0142133 A1 | 6/2005 | Lazar et al. |
| 2005/0142635 A1 | 6/2005 | Tsuchiya et al. |
| 2005/0261229 A1 | 11/2005 | Gillies et al. |
| 2006/0019340 A1 | 1/2006 | Naor et al. |
| 2006/0134709 A1 | 6/2006 | Stavenhagen et al. |
| 2006/0141456 A1 | 6/2006 | Edwards et al. |
| 2006/0194280 A1 | 8/2006 | Dillon et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0041978 A1 | 2/2007 | Hattori et al. |
| 2007/0059312 A1 | 3/2007 | Baca et al. |
| 2007/0134234 A1 | 6/2007 | Smith et al. |
| 2007/0178102 A1 | 8/2007 | Yarden et al. |
| 2007/0224174 A1 | 9/2007 | Kang et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0239577 A1 | 9/2010 | Igawa et al. |

(Continued)

FOREIGN PATENT DOCUMENTS

| | | |
|---|---|---|
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 625 773 | 4/2007 |
| CA | 2 626 688 | 4/2007 |

(Continued)

OTHER PUBLICATIONS

Mariuzza et al. (Annu. Rev. Biophys. Biophys. Chem. 1987; 16: 139-159).*

(Continued)

*Primary Examiner* — Brad Duffy
(74) *Attorney, Agent, or Firm* — Fish & Richardson P.C.

(57) ABSTRACT

An objective of the present invention is to decrease the immunogenicity of mouse-derived anti-AXL antibodies in humans by humanizing them. The present invention provides antibodies that can bind to a specific region in Anexelekto (AXL) and humanized antibodies that are produced based on such antibodies. The anti-AXL antibodies of the present invention have high antitumor activity, and are useful as agents for decreasing the AXL expression level, antitumor agents, and diagnostic agents for cancer.

23 Claims, 7 Drawing Sheets

(56) References Cited

U.S. PATENT DOCUMENTS

| | | |
|---|---|---|
| 2010/0298542 A1 | 11/2010 | Igawa et al. |
| 2011/0044984 A1* | 2/2011 | Kitazawa et al. .......... 424/138.1 |
| 2011/0076275 A1 | 3/2011 | Igawa et al. |
| 2011/0111406 A1 | 5/2011 | Igawa et al. |
| 2011/0245473 A1 | 10/2011 | Igawa et al. |
| 2012/0065379 A1 | 3/2012 | Igawa et al. |
| 2012/0071634 A1 | 3/2012 | Igawa et al. |
| 2012/0238729 A1 | 9/2012 | Kuramochi et al. |
| 2013/0011866 A1 | 1/2013 | Igawa et al. |
| 2013/0101581 A1 | 4/2013 | Kuramochi et al. |
| 2015/0274809 A1 | 10/2015 | Igawa et al. |
| 2015/0284465 A1 | 10/2015 | Igawa et al. |

FOREIGN PATENT DOCUMENTS

| | | |
|---|---|---|
| CA | 2 700 986 | 4/2009 |
| EP | 0 783 893 | 7/1997 |
| EP | 1 069 185 | 1/2001 |
| EP | 1 382 969 | 1/2004 |
| EP | 1 847 602 | 10/2007 |
| EP | 2 194 066 | 6/2010 |
| EP | 2 206 775 | 7/2010 |
| JP | 2-028200 | 1/1990 |
| JP | 07-67688 | 3/1995 |
| JP | 2004-511426 | 4/2004 |
| JP | 2005-532805 | 11/2005 |
| JP | 2005-535341 | 11/2005 |
| JP | 2013-165716 | 8/2013 |
| JP | 5334319 | 11/2013 |
| JP | 5484060 | 5/2014 |
| RU | 2232773 | 7/2004 |
| RU | 2266298 | 12/2005 |
| WO | WO 92/19759 | 11/1992 |
| WO | WO 95/14710 | 6/1995 |
| WO | WO 96/11020 | 4/1996 |
| WO | WO 96/12503 | 5/1996 |
| WO | WO 97/09351 | 3/1997 |
| WO | WO 98/03546 | 1/1998 |
| WO | WO 99/51743 | 10/1999 |
| WO | WO 99/58572 | 11/1999 |
| WO | WO 01/30854 | 5/2001 |
| WO | WO 01/82899 | 11/2001 |
| WO | WO 02/072605 | 9/2002 |
| WO | WO 03/057881 | 7/2003 |
| WO | WO 03/105757 | 12/2003 |
| WO | WO 2004/008147 | 1/2004 |
| WO | WO 2004/016740 | 2/2004 |
| WO | WO 2004/068931 | 8/2004 |
| WO | WO 2004/096273 | 11/2004 |
| WO | WO 2005/035756 | 4/2005 |
| WO | WO 2005/047327 | 5/2005 |
| WO | WO 2005/056606 | 6/2005 |
| WO | WO 2005/067620 | 7/2005 |
| WO | WO 2005/123126 | 12/2005 |
| WO | WO 2006/019447 | 2/2006 |
| WO | WO 2006/030200 | 3/2006 |
| WO | WO 2006/030220 | 3/2006 |
| WO | WO 2006/047350 | 5/2006 |
| WO | WO 2006/071877 | 7/2006 |
| WO | WO 2006/075668 | 7/2006 |
| WO | WO 2006/109592 | 10/2006 |
| WO | WO 2007/089871 | 8/2007 |
| WO | WO 2007/108559 | 9/2007 |
| WO | WO 2007/114319 | 10/2007 |
| WO | WO 2007/114325 | 10/2007 |
| WO | WO 2008/092117 | 7/2008 |
| WO | WO 2008/145141 | 12/2008 |
| WO | WO 2009/041613 | 4/2009 |
| WO | WO 2009/041621 | 4/2009 |
| WO | WO 2009/041643 | 4/2009 |
| WO | WO 2009/052439 | 4/2009 |
| WO | WO 2009/062690 | 5/2009 |
| WO | WO 2009/063965 | 5/2009 |
| WO | WO 2009/100309 | 8/2009 |
| WO | WO 2009/125825 | 10/2009 |
| WO | WO 2011/111007 | 9/2011 |

OTHER PUBLICATIONS

Gussow et al. (Methods in Enzymology. 1991; 203: 99-121).*
Winkler et al (J. Imm., 265:4505-4514, 2000).*
USPTO Final Office Action and Interview Summary in U.S. Appl. No. 12/742,947, dated Mar. 7, 2013, 15 pages.
USPTO Restriction Requirement in U.S. Appl. No. 13/257,145, dated Mar. 20, 2013, 11 pages.
Allen et al., "Novel mechanism for gonadotropin-releasing hormone neuronal migration involving Gas6/Ark signaling to p38 mitogen-activated protein kinase," *Mol. Cell. Biol.*, 22(2):599-613 (2002).
Bellosta et al., "Signaling through the ARK tyrosine kinase receptor protects from apoptosis in the absence of growth stimulation," *Oncogene.*, 15(20):2387-97 (1997).
Budagian et al., "A promiscuous liaison between IL-15 receptor and Axl receptor tyrosine kinase in cell death control," *EMBO J.*, 24(24):4260-70 (2005).
Chirino et al., "Minimizing the immunogenicity of protein therapeutics," *Drug Discov. Today*, 9(2):82-90 (2004).
Chung et al., "Expression of the proto-oncogene Axl in renal cell carcinoma," *DNA Cell Biol.*, 22(8):533-40 (2003).
Craven et al., "Receptor tyrosine kinases expressed in metastatic colon cancer," *Int. J. Cancer*, 60(6):791-7 (1995).
Ewert et al., "Stability improvement of antibodies for extracellular and intracellular applications: CDR grafting to stable frameworks and structure-based framework engineering," *Methods.*, 34(2):184-99 (2004).
Fridell et al., "GAS6 induces Axl-mediated chemotaxis of vascular smooth muscle cells," *J. Biol. Chem.*, 273(12):7123-6 (1998).
Goruppi et al., "Requirement of phosphatidylinositol 3-kinase-dependent pathway and Src for Gas6-Axl mitogenic and survival activities in NIH 3T3 fibroblasts," *Mol. Cell Biol.*, 17(8):4442-53 (1997).
Hafizi et al., "Interaction of Axl receptor tyrosine kinase with C1-TEN, a novel C1 domain-containing protein with homology to tensin," *Biochem. Biophys. Res. Commun.*, 299(5):793-800 (2002).
Hafizi et al., "Signalling and functional diversity within the Axl subfamily of receptor tyrosine kinases," *Cytokine Growth Factor Rev.*, 17(4):295-304 (2006).
Hanes et al., "Picomolar affinity antibodies from a fully synthetic naive library selected and evolved by ribosome display," *Nat. Biotechnol.*, 18(12):1287-92 (2000).
Holland et al., "Multiple roles for the receptor tyrosine kinase ax1 in tumor formation," *Cancer Res.*, 65(20):9294-303.
Ito et al., "Expression of receptor-type tyrosine kinase, Axl, and its ligand, Gas6, in pediatric thyroid carcinomas around Chernobyl," *Thyroid.*, 12(11):971-5 (2002).
McCloskey et al., "GAS6 mediates adhesion of cells expressing the receptor tyrosine kinase Axl," *J. Biol. Chem.*, 272(37):23285-91 (1997).
Meric et al., "Expression profile of tyrosine kinases in breast cancer," *Clin. Cancer Res.*, 8(2):361-7 (2002).
Nakano et al., "Vascular smooth muscle cell-derived, Gla-containing growth-potentiating factor for Ca(2+)-mobilizing growth factors," *J. Biol. Chem.*, 270(11):5702-5 (1995).
Nakano et al., "Prevention of growth arrest-induced cell death of vascular smooth muscle cells by a product of growth arrest-specific gene, gas6," *FEBS Lett.*, 387(1):78-80 (1996).
Nemoto et al., "Overexpression of protein tyrosine kinases in human esophageal cancer," *Pathobiology.*, 65(4):195-203 (1997).
Neubauer et al., "Expression of axl, a transforming receptor tyrosine kinase, in normal and malignant hematopoiesis," *Blood*, 84(6):1931-41 (1994).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pavlaki et al., "Matrix metalloproteinase inhibitors (MMPIs): the beginning of phase I or the termination of phase III clinical trials," *Cancer Metastasis Rev.*, 22(2-3):177-203 (2003).

(56) References Cited

OTHER PUBLICATIONS

Sainaghi et al., "Gas6 induces proliferation in prostate carcinoma cell lines expressing the Axl receptor," *J. Cell. Physiol.*, 204(1):36-44 (2005).
Sawabu et al., "Growth arrest-specific gene 6 and Axl signaling enhances gastric cancer cell survival via Akt pathway," *Mol. Carcinog.*, 46(2):155-64 (2007).
Shieh et al., "Expression of axl in lung adenocarcinoma and correlation with tumor progression," *Neoplasia.*, 7(12):1058-64 (2005).
Stenhoff et al., "Vitamin K-dependent Gas6 activates ERK kinase and stimulates growth of cardiac fibroblasts," *Biochem. Biophys. Res. Commun.*, 319(3):871-8 (2004).
Sun et al., "Coexpression of Gas6/Axl in human ovarian cancers," *Oncology*, 66(6):450-7 (2004).
Vaisitti et al., "Cationization of monoclonal antibodies: another step towards the "magic bullet"?," *J. Biol. Regul. Homeost. Agents.*, 19(3-4):105-12 (2005).
Vajkoczy et al., "Dominant-negative inhibition of the Axl receptor tyrosine kinase suppresses brain tumor cell growth and invasion and prolongs survival," *Proc. Natl. Acad. Sci. U.S.A.*, 103(15):5799-804 (2006).
Varnum et al., "Axl receptor tyrosine kinase stimulated by the vitamin K-dependent protein encoded by growth-arrest-specific gene 6," *Nature*, 373(6515):623-6 (1995).
Yamagata et al., "Synaptic adhesion molecules," *Curr. Opin. Cell Biol.*, 15(5):621-32 (2003).
Fish & Richardson P.C., Response to Species Election Requirement dated Jun. 25, 2012 in U.S. Appl. No. 12/936,587, filed Jul. 25, 2012, 1 page.
Bayry et al , "Immuno affinity purification of foot and mouth disease virus type specific antibodies using recombinant protein adsorbed to polystyrene wells," *J. Virol. Methods*, 81:21-30 (1999).
Kobayashi et al., "A monoclonal antibody specific for a distinct region of hen egg-white lysozyme," *Mol. Immunol.*, 19:619-30 (1982).
Ozhegov et al., Tolkovyi Slovar Russkogo iazyka: 2004, p. 292 (with an English translation of the relevant passage defining "control").
USPTO Non-Final Office Action in U.S. Appl. No. 12/936,587, dated Nov. 7, 2012, 13 pages.
USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
USPTO Non-Final Office Action in U.S. Appl. No. 13/595,139, dated Nov. 14, 2012, 10 pages.
Casset et al., "A peptide mimetic of an anti-CD4 monoclonal antibody by rational design," *Biochem. Biophys. Res. Commun.*, 307:198-205 (2003).
DePascalis et al., "Grafting of "abbreviated" complementarity-determining regions containing specificity-determining residues essential for ligand contact to engineer a less immunogenic humanized monoclonal antibody," *J. Immunol.*, 169:3076-3084 (2002).
O'Bryan et al., "axl, a transforming gene isolated from primary human myeloid leukemia cells, encodes a novel receptor tyrosine kinase," *Mol. Cell Biol.*, 11(10):5016-31 (1991).
Paul, "Structure and function of immunoglobulins," Fundamental Immunology, Third Edition, 292-295 (1993).
Fish & Richardson P.C., Preliminary Amendment and Response to Restriction Requirement dated May 14, 2012 in U.S. Appl. No. 12/742,947, filed Jun. 14, 2012, 9 pages.
USPTO Non-Final Office Action in U.S. Appl. No. 12/742,947, dated Jul. 6, 2012, 25 pages.
USPTO Restriction Requirement in U.S. Appl. No. 12/936,587, dated Jun. 25, 2012, 5 pages.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
Adams et al., "Humanization of a recombinant monoclonal antibody to produce a therapeutic HER dimerization inhibitor, dimenon bitor, pertuzumab," *Cancer Immunol. Immunother.*, 55:717-727 (2006).
Altar et al., "AXL receptor tyrosine kinase expression in human breast cancer," Breast Cancer Research and Treatment, Springer, New York, NY (Abstracts—Poster session III) 46(1):91 (1997).
Armour et al., "Recombinant human IgG molecules lacking Fcgamma receptor I binding and monocyte triggering activities," *Eur. J. Immunol.*, 29(8):2613-24 (1999).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bender et al., "Immunogenicity, efficacy and adverse events of adalimumab in RA patients," *Rheumatol. Int.*, 27:269-274 (2007).
Binz et al., "Engineering novel binding proteins from nonimmunoglobulin domains," *Nat. Biotechnol.*, 23:1257-68 (2005).
Brown et al., "Tolerance of single, but not multiple, amino acid replacements in antibody $V_H$ CDR 2: a means of minimizing B cell wastage from somatic hypermutation?," *J. Immunol.*, 156(9):3285-91 (1996).
Chau et al., "HuM291(Nuvion), a humanized Fc receptor-nonbinding antibody against CD3, anergizes peripheral blood T cells as partial agonist of the T cell receptor," *Transplantation.*, 71(7):941-50 (2001).
Chu et al., "Accumulation of succinimide in a recombinant monoclonal antibody in mildly acidic buffers under elevated temperatures," *Pharm. Res.*, 24(6):1145-56 (2007).
Cole et al., "Human IgG2 variants of chimeric anti-CD3 are nonmitogenic to T cells," *J. Immunol.*, 159(7):3613-21 (1997).
Cordoba et al., "Non-enzymatic hinge region fragmentation of antibodies in solution," *J. Chromatogr. B. Analyt. Technol. Biomed. Life Sci.*, 818(2):115-21 (2005).
Couto et al., "Anti-BA46 Monoclonal Antibody Mc3: Humanization Using a Novel Positional Consensus and in Vivo and in Vitro Characterization," *Cancer Res.*, 55:1717-22 (1995).
Dall'Acqua et al., "Antibody humanization by framework shuffling," *Methods*, 36(1):43-60 (2005).
Davies et al., "Affinity improvement of single antibody VH domains: residues in all three hypervariable regions affect antigen binding," *Immunotechnology*, 2(3):169-79 (1996).
Deng et al., "An Agonist Murine Monoclonal Antibody to the Human c-Mpl Receptor Stimulates Megakaryocytopoiesis," *Blood*, 92:1981-88 (1998).
Dillon et al., "Structural and functional characterization of disulfide isoforms of the human IgG2 subclass," *J. Biol. Chem.*, 283(23):16206-15 (2008).
Gessner et al., "The IgG Fc receptor family," *Ann Hematol.*, 76(6):231-48 (1998).
Ghetie et al., "FcRn: the MHC class I-related receptor that is more than an IgG transporter," *Immunol. Today*, 18:592-598 (1997).
Ghetie et al., "Increasing the serum persistence of an IgG fragment by random mutagenesis," *Nat. Biotechnol.*, 15:637-640 (1997).
Giusti et al., "Somatic diversification of S107 from an antiphosphocholine to an anti-DNA autoantibody is due to a single base change in its heavy chain variable region," *Proc. Natl. Acad. Sci. U.S.A.*, 84(9):2926-30 (1987).

(56) References Cited

OTHER PUBLICATIONS

Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).

Graves et al., "Molecular modeling and preclinical evaluation of the humanized NR-LU-13 antibody," *Clin. Cancer Res.*, 5:899-908 (1999).

Guyre et al., "Increased potency of Fc-receptor-targeted antigens," *Cancer Immunol. Immunother.*, 45(3-4):146-8 (1997).

He et al., "Humanization and pharmacokinetics of a monoclonal antibody with specificity for both E- and P-selectin," *J. Immunol.*, 160:1029-35 (1998).

Hinton et al., "An engineered human IgG1 antibody with longer serum half-life," *J. Immunol.*, 176:346-356 (2006).

Holt et al., "Domain antibodies: proteins for therapy," *Trends Biotechnol.*, 21(11):484-90 (2003).

Hwang et al., "Use of human germline genes in a CDR homology-based approach to antibody humanization," Methods, 36:35-42 (2005).

Johnson et al., "Cation exchange-HPLC and mass spectrometry reveal C-terminal amidation of an IgG1 heavy chain," *Anal. Biochem.*, 360(1):75-83 (2007).

Jones et al., "Identification and removal of a promiscuous CD4+ T cell epitope from the C1 domain of factor VIII," *Thromb. Haemost.*, 3:991-1000 (2005).

Kashmiri et al., "Generation, characterization, and in vivo studies of humanized anticarcinoma antibody CC49," *Hybridoma*, 14:461-473 (1995).

Kim et al., "Antibody Engineering for the Development of Therapeutic Antibodies," Mol. Cells, 20:17-29 (2005).

Kussie et al., "A single engineered amino acid substitution changes antibody fine specificity," *J. Immunol.*, 152(1):146-52 (1994).

Liu et al., "Fine mapping of the antigen-antibody interaction of scFv215, a recombinant antibody inhibiting RNA polymerase II from *Drosophila melanogaster*," *J. Mol. Recognit.*, 12(2):103-11 (1999).

Lobo et al., "Antibody pharmacokinetics and pharmacodynamics," *J. Pharm. Sci.*, 93:2645-68 (2004).

MacCallum et al., "Antibody-antigen interactions: contact analysis and binding site topography," *J. Mol. Biol.*, 262:732-45 (1996).

Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).

Maynard et al., "Antibody engineering," *Annu. Rev. Biomed. Eng.*, 2:339-76 (2000).

Nishimoto et al., "Interleukin 6: from bench to bedside," *Nat. Clin. Pract. Rheumatol.*, 2:619-626 (2006).

Nishimoto et al., "Humanized anti-interleukin-6 receptor antibody treatment of multicentric Castleman disease," *Blood*, 106:2627-32 (2005).

Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).

Pavlou et al., "The therapeutic antibodies market to 2008," *Eur. J Pharm. Biopharm.*, 59(3):389-96 (2005).

Pint et al., "Design and use of a phage display library. Human antibodies with subnanomolar affinity against a marker of angiogenesis eluted from a two-dimensional gel," *J. Biol. Chem.*, 273(34):21769-76 (1998).

Poduslo et al., "Polyamine modification increases the permeability of proteins at the blood-nerve and blood-brain barriers," *J. Neurochem.*, 66:1599-1609 (1996).

R&D Systems, Safety Data Sheet, "Human Axl Antibody Monoclonal Mouse IgG1 Clone # 108724," Catalog No. MAB154 (2012).

Rajpal et al., A general method for greatly improving the affinity of antibodies by using combinatorial libraries, Proc. Natl. Acad. Sci. USA, 102:8466-71 (2005).

Reddy et al., "Elimination of Fc receptor-dependent effector functions of a modified IgG4 monoclonal antibody to human CD4," *J. Immunol.*, 164(4):1925-33 (2000).

Reichert et al., "Monoclonal antibody successes in the clinic," *Nat. Biotechnol.*, 23(9):1073-8 (2005).

Rothe et al., "Ribosome display for improved biotherapeutic molecules," *Expert Opin. Biol. Ther.*, 6:177-187 (2006).

Salfeld et al., "Isotype selection in antibody engineering," *Nat. Biotechnol.*, 25:1369-72 (2007).

Sato et al., "Reshaping a human antibody to inhibit the interleukin 6-dependent tumor cell growth," *Cancer Res.*, 53:851-856 (1993).

Schildbach et al., "Contribution of a single heavy chain residue to specificity of an anti-digoxin monoclonal antibody," *Protein Sci.*, 3(5):737-49 (1994).

Schildbach et al., "Heavy chain position 50 is a determinant of affinity and specificity for the anti-digoxin antibody 26-10," *J. Biol. Chem.*, 268(29):21739-47 (1993).

Shire et al., "Challenges in the development of high protein concentration formulations," *J. Pharm. Sci.*, 93(6):1390-402 (2004).

Strand et al., "Biologic therapies in rheumatology: lessons learned, future directions," *Nat. Rev. Drug Discov.*, 6(1):75-92 (2007).

Tsurushita et al., "Design of humanized antibodies: From anti-Tac to Zenapax," Methods, 36:69-83 (2005).

Vajdos et al., "Comprehensive functional maps of the antigen-binding site of an anti-ErbB2 antibody obtained with shotgun scanning mutagenesis," *J. Mol. Biol.*, 320(2):415-28 (2002).

Wu et al., "Development of motavizumab, an ultra-potent antibody for the prevention of respiratory syncytial virus infection in the upper and lower respiratory tract," *J. Mol. Biol.*, 368:652-665 (2007).

Xiang et al., "Study of B72.3 combining sites by molecular modeling and site-directed mutagenesis," *Protein Eng.*, 13(5):339-44 (2000).

Yamasaki et al., "Pharmacokinetic analysis of in vivo disposition of succinylated proteins targeted to liver nonparenchymal cells via scavenger receptors: importance of molecular size and negative charge density for in vivo recognition by receptors," *J. Pharmacol. Exp. Ther.*, 301:467-477 (2002).

Zuckier et al., "Chimeric human-mouse IgG antibodies with shuffled constant region exons demonstrate that multiple domains contribute to in vivo half-life," Cancer Res., 58:3905-08 (1998).

USPTO Non-Final Office Action in U.S. Appl. No. 12/679,922, dated Jan. 3, 2013, 25 pages.

International Search Report App. Ser. No. PCT/JP2007/057058, mailed May 7, 2001, 2 pages.

Fish & Richardson P.C., Response to Office Action dated Jul. 6, 2012 in U.S. Appl. No. 12/742,947, filed Jan. 7, 2013, 63 pages.

Igawa et al., "Engineering the variable region of therapeutic IgG antibodies," *MAbs*, 3(3):243-52 (2011).

Igawa et al., "Reduced elimination of IgG antibodies by engineering the variable region," *Protein Eng. Des. Sel.*, 23(5):385-92 (2010).

Lay et al., "Sulfasalazine suppresses drug resistance and invasiveness of lung adenocarcinoma cells expressing AXL," *Cancer Res.*, 67(8):3878-87 (2007).

Maeda et al., "pH-dependent receptor/ligand dissociation as a determining factor for intracellular sorting of ligands for epidermal growth factor receptors in rat hepatocytes," *J. Control Release*, 82(1):71-82 (2002).

Maxfield et al., "Endocytic recycling," *Nat. Rev. Mol. Cell Biol.*, 5(2):121-32 (2004).

Murtaugh et al., "A combinatorial histidine scanning library approach to engineer highly pH-dependent protein switches," *Protein Sci.*, 20(9):1619-31 doi:10.1002/pro 696 (2011).

Wang et al., "Polyethylene Glycol-modified Chimeric Toxin Composed of Transforming Growth Factor alpha and *Pseudomonas* Exotoxin," *Cancer. Res.*, 53:4588-4594 (1993).

European Search Report for App. Ser. No. EP 09 72 9337, dated Nov. 3, 2011, 3 pages.

USPTO Restriction Requirement in U.S. Appl. No. 12/742,947, mailed May 14, 2012, 7 pages.

International Preliminary Report on Patentability for App. Ser. No. PCT/JP2010/058166, dated Dec. 16, 2011, 15 pages.

USPTO Restriction Requirement in U.S. Appl. No. 12/936,587, dated Dec. 6, 2011, 7 pages.

(56) References Cited

OTHER PUBLICATIONS

Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/680,082, dated Jun. 6, 2012, 12 pages.
Amersham Biosciences, "Affinity Chromatography: Principles and Methods," Edition AD, pp. 16-18, 137 (2002).
Berzofsky et. al., "Antigen-antibody interaction," *Fundamental Immunology*, by Paul et al. (3$^{rd}$ Edition), Raven Press ( 1987-1989), Chapter 23, pp. 47-49 (with English translation).
Presta, "Engineering of therapeutic antibodies to minimize immunogenicity and optimize function," *Adv. Drug Deliv. Rev.*, 58(5-6):640-56 (2006).
Presta et al., "Molecular engineering and design of therapeutic antibodies," *Curr. Opin. Immunol.*, 20(4):460-70 (2008).
Roitt et al., *Immunology, M. Mir*, 150-155 (2000) (with corresponding English text: Roitt et al., "Antigen Recognition," *Immunology*, 5$^{th}$ Edition, 107-112).
Zhu et al., "MHC class I-related neonatal Fc receptor for IgG is functionally expressed in monocytes, intestinal macrophages, and dendritic cells," *J. Immunol.*, 166(5):3266-76 (2001).
USPTO Interview Summary in U.S. Appl. No. 12/742,947, dated Feb. 22, 2013, 3 pages.
USPTO Non-Final Office Action U.S. Appl. No. 12/680,082, dated Feb. 14, 2013, 12 pages.
Berzofsky et al., "Immunogenicity and Antigen Structure," *Fundamental Immunology*, by Paul et al. (3$^{rd}$ Edition), Raven Press (1984), Chapter 21, pp. 58-59 (with English translation).
Li et al., "Axl as a potential therapeutic target in cancer: role of Axl in tumor growth, metastasis and angiogenesis," *Oncogene*, 28(39):3442-3455 (2009).
Martinez et al., "Disulfide connectivity of human immunoglobulin G2 structural isoforms," *Biochemistry*, 47(28):7496-7508 (2008).
Roitt et al., *Immunology, M. Mir*, p. 110 (2000) (with English translation).
Rudikoff et al., "Single amino acid substitution altering antigen-binding specificity," *Proc. Natl. Acad. Sci. U.S.A.*, 79(6):1979-1983 (1982).
Wypych et al., "Human IgG2 antibodies display disulfide-mediated structural isoforms," *J. Biol. Chem.*, 283(23):16194-16205 (2008).
International Search Report for App. Ser. No. PCT/JP2010/058166, mailed Jun. 15, 2010, 5 pages.
Allen et al., "Interchain disulfide bonding in human IgG2 antibodies probed by site-directed mutagenesis," *Biochemistry*, 48(17):3755-66 (2009).
Dall'Acqua et al., "Modulation of the effector functions of a human IgG1 through engineering of its hinge region," *J. Immunol.*, 177(2):1129-38 (2006).
Pakula et al., "Genetic Analysis of Protein Stability and Function," *Annu. Rev. Genet.*, 23:289-310 (1989).
Paul, Fundamental Immunology, Third Edition, M. Mir, 3:250 (1987-1988) (with English translation of relevant p.).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Tarantula, "Glossary of biomedical terms", M: Inform Its Rospatent, 126 (2005) (with English translation of relevant page, see p. 105).
Fish & Richardson P.C., Preliminary Amendment and Response to Restriction Requirement dated Mar. 20, 2013 in U.S. Appl. No. 13/257,145, filed Apr. 22, 2013, 7 pages.
Fish & Richardson P.C., Amendment in Reply to Action dated Jan. 3, 2013 in U.S. Appl. No. 12/679,922, filed Jul. 2, 2013, 18 pages.
USPTO Final Office Action in U.S. Appl. No. 12/679,922, dated Aug. 2, 2013, 12 pages.
USPTO Non-Final Office Action in U.S. Appl. No. 13/257,145, dated Jul. 2, 2013, 20 pages.
Fish & Richardson P.C., Response to Final Office Action dated Mar. 7, 2013 in U.S. Appl. No. 12/742,947, filed Aug. 6, 2013, 10 pages.
Fish & Richardson P.C., Amendment in Reply to Non-Final Office Action dated Feb. 14, 2013 in U.S. Appl. No. 12/680,082, filed Aug. 12, 2013, 17 pages.
USPTO Final Office Action U.S. Appl. No. 12/680,082, dated Oct. 22, 2013, 12 pages.
USPTO Restriction Requirement in U.S. Appl. No. 13/257,112, dated Oct. 15, 2013, 10 pages.
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Wally et al., "Identification of a novel substitution in the constant region of a gene coding for an amyloidogenic kappa1 light chain," *Biochim Biophys Acta.*, May 31, 1999;1454(1):49-56.
Vajkoczy et al., "Dominant-negative inhibition of the Axl receptor tyrosine kinase suppresses brain tumor cell growth and invasion and prolongs survival-Date Supplement" Apr. 11, 2006;103(15):5799, p. 1S. Retrieved from the Internet: http://www.ncbi.nlm.nih.gov/pmc/articles/PMC1458653/bin/pnas_0510923103_index.html [retrieved on Feb. 10, 2015].
Datta-Mannan et al., "Monoclonal antibody clearance. Impact of modulating the interaction of IgG with the neonatal Fc receptor," *J Biol Chem.*, 282(3):1709-17 (2007).
Fish & Richardson P.C., Response to Final Office Action dated Jun. 19, 2014 in U.S. Appl. No. 12/742,947, filed Sep. 18, 2014, 9 pages.
USPTO Final Office Action in U.S. Appl. No. 12/742,947, dated Oct. 15, 2014, 8 pages.
Batra et al., "Pharmacokinetics and biodistribution of genetically engineered antibodies," *Curr Opin Biotechnol.*, Dec. 2002;13(6):603-8.
Paul, "Immunology," a Russian translation of English book, M.: Mir, 3:248-251 (1987-1988) (with English bibliographic data).
Pokrovskiy, "Small medical encyclopedia," in 6 volumes. Meditsinskaya entsiclopedia, 1A:139, right column (1991) (with English bibliographic data).
Stepanov, "Molecular Biology. Structure and Functions of Proteins," Nauka, 144-145 (2005) (with English bibliographic data).
Tsubaki et al., "C-terminal modification of monoclonal antibody drugs: amidated species as a general product-related substance," *Int J Biol Macromol.*, 52:139-47. doi: 10.1016/j.ijbiomac.2012.09.016. Epub Sep. 25, 2012.
Yarilin, Fundamentals of Immunology, Meditsina, 203-204 (1999) (with English bibliographic data).
USPTO Non-Final Office Action in U.S. Appl. No. 12/742,947, dated Jun. 19, 2014, 8 pages.
Smolen et al., "Interleukin-6: a new therapeutic target," *Arthritis Res Ther.*, 2006;8 Suppl 2:S5. Epub Jul. 28, 2006.
Chappel et al., "Identification of a secondary Fc gamma RI binding site within a genetically engineered human IgG antibody," *J Biol Chem.*, Nov. 25, 1993;268(33):25124-31.
Chappel et al., "Identification of the Fc gamma receptor class I binding site in human IgG through the use of recombinant IgG1/IgG2 hybrid and point-mutated antibodies," *Proc Natl Acad Sci USA.*, Oct. 15, 1991;88(20):9036-40.
Reist et al., "Human IgG2 constant region enhances in vivo stability of anti-tenascin antibody 81C6 compared with its murine parent," *Clin Cancer Res.*, Oct. 1998;4(10):2495-502.
Fish & Richardson P.C., Amendment in Reply to Office Action dated Oct. 15, 2014 in U.S. Appl. No. 12/742,947, filed Jan. 9, 2015, 12 pages.
USPTO Advisory Action in U.S. Appl. No. 12/742,947, dated Jan. 26, 2015, 2 pages.
Fish & Richardson P.C., Supplemental Amendment in Reply to Action of Oct. 15, 2014, and Advisory Action of Jan. 26, 2015 in U.S. Appl. No. 12/742,947, filed Feb. 13, 2015, 5 pages.
USPTO Notice of Allowance in U.S. Appl. No. 12/742,947, dated Jun. 18, 2015, 10 pages.

\* cited by examiner

| CLONE# | SUBTYPE | ANTITUMOR ACTIVITY (Panc-1: 2ND TRIAL) | BINDING DOMAIN |
|---|---|---|---|
| #225 | 1 | ++ | FND-1 |
| #284 | 2a | ++ | FND-1, IgD2 |
| #7 | 1 | + | IgD2 |
| #51 | 1 | + | IgD2 |
| #285 | 2a | − | IgD2 |
| #223 | 2b | − | IgD2 |
| #96 | 1 | − | IgD1 |
| #292 | 2b | − | IgD2 |
| #258 | 1 | − | IgD2 |

−: TGI(%) <30, +: TGI(%) <60, ++: 60=<TGI(%)

FIG. 1

ANTI-AXL ANTIBODY

CROSS-REFERENCE TO RELATED APPLICATIONS

This application is the National Stage of International Application Serial No. PCT/JP2010/058166, filed on May 14, 2010, which claims priority to Japanese Application Serial No. 2009-118725, filed on May 15, 2009.

TECHNICAL FIELD

The present invention relates to anti-anexelekto (AXL) antibodies, and anticancer agents containing the antibodies as an active ingredient.

BACKGROUND ART

Anexelekto (also referred to as "AXL", "UFO", "ARK", or "TYRO7"; hereinafter referred to as "AXL") is a receptor tyrosine kinase that exists on the cell membrane (Non-patent Document 1). It is said to be responsible for signal transduction to downstream molecules through its autophosphorylation, which occurs after it binds to the ligand Gas6 (growth arrest specific gene 6) (Non-patent Document 2).

AXL is presumed to have molecular functions involved in cell growth enhancement, suppression of apoptosis, cell migration, and cell adhesion. Experimentally observed phenomena in cells treated with Gas6 protein support this presumption. Reported experimental results include suppression of cell death and enhancement of cell growth in rat vascular smooth muscle (Non-patent Documents 3 and 4), acceleration of cell growth and the suppression of cell death after serum starvation in mouse NIH3T3 cells (Non-patent Documents 5 and 6), promotion of cell growth in mouse cardiac fibroblasts (Non-patent Document 7), enhancement of cell growth in human prostate cancer cells (Non-patent Document 8), enhancement of cell growth and infiltration and suppression of cell death in human gastric carcinoma cells (Non-patent Document 9), enhancement of the migration ability of human and rat vascular smooth muscle cells (Non-patent Document 10), enhancement of the cell migration ability of mouse neurons (Non-patent Document 11), and aggregation of cells highly expressing mouse AXL (Non-patent Document 12).

Similarly, PI3K-Akt pathway and MAPK pathway are said to function as downstream pathways of the signal transduction mediated by AXL based on molecular analyses of intracellular signals after treatment with Gas6 (Non-patent Document 2). An analysis with a yeast two-hybrid method using an AXL intracellular region as bait confirmed direct molecular interaction with these downstream pathways. As a result, GrbB2/PI3K/p55γ/SOCS-1/NcK2/RanBP2/C1-TEN were identified (Non-patent Document 13). The interactions of these molecules suggest the presence of intracellular signal transduction pathways as downstream from the AXL signal. Furthermore, the observed interactions support the presumption that AXL functions in cell growth enhancement, suppression of apoptosis, cell migration, and cell adhesion. AXL has also been identified as a gene highly expressed when TNFα-induced cell death of mouse fibroblasts is suppressed by IL-15. The suppression of TNFα-induced cell death was abolished by suppressing AXL expression, and the phosphorylation of IL-15 receptors and AXL was enhanced by treatment with IL-15. These experimental findings also suggest that signal transduction is mediated by the complex of AXL and IL-15 receptors (Non-patent Document 14).

Tumorigenicity of nude mice has been reported to disappear as a result of inhibiting Gas6-dependent phosphorylation of AXL in human glioma lines overexpressing the AXL dominant negative form (Non-patent Document 15). However, there were no reports or suggestions of anti-AXL antibody that inhibits phosphorylation and its existence remained unclear.

AXL is a single-pass transmembrane receptor tyrosine kinase, and the extracellular region is composed of two immunoglobulin-like domains (referred to as IgD1 and IgD2) and two fibronectin type III domains (referred to as FND1 and FND2) from the N-terminal side (Non-patent Document 1). Although FND is known to be expressed in molecules such as neural cell adhesion molecules and nephrins involved in intercellular adhesion, detailed functions of FND in AXL are unclear (Non-patent Document 16).

AXL has been identified as an oncogene that retains an inherent ability to transform cells, and has been studied as a carcinogenesis-related molecule. Many analyses of AXL expression have been reported on the protein and mRNA. The high expression of AXL protein has been reported in human cancer tissues and cancer cells, including lung cancer (Non-patent Document 17), breast cancer (Non-patent Document 18), ovarian cancer (Non-patent Document 19), thyroid cancer (Non-patent Document 20), melanoma (Non-patent Document 20), renal cancer (Non-patent Document 21), gastric cancer (Non-patent Document 9), and glioma (Non-patent Document 22). Furthermore, the high expression of AXL protein is suggested by the high level of AXL mRNA in esophageal cancer (Non-patent Document 23), colon cancer (Non-patent Document 24), and acute myeloid leukemia (Non-patent Document 25). There are also reports of inhibition of lumen formation via suppression of AXL by RNAi in HUVEC (Non-patent Document 26), reduced tumor-forming ability of human breast cancer cells in mice resulting from constitutive suppression of AXL (Non-patent Document 26), and reduced tumor-forming ability of human glioma cells in mice resulting from a constitutive high expression of dominant negative mutants (Non-patent Document 22). The involvement of AXL molecular functions in tumor growth is strongly suggested.

Polyclonal antibodies to the extracellular domain of AXL have been reported to have a migration inhibitory action on highly invasive breast cancer cell lines (Patent Document 1). However, non-clinical studies showed that drugs demonstrating cancer-cell-migration-inhibitory action do not necessarily demonstrate antitumor activity. For example, matrix metalloproteinase (hereinafter abbreviated to "MMP") has been known to promote tumor infiltration and migration. Thus, as candidates of anticancer agents, attention has been focused on various matrix metalloproteinase inhibitors that inhibit the enzyme activity of MMP, and clinical studies have been conducted on various pharmaceutical agents such as Batimastat, Marimastat, and Prinomastat. However, antitumor effects have not been observed in clinical trials (Non-patent Document 27).

Accordingly, there have been no reports or suggestions and it remains unknown whether antibodies that bind to a specific region of AXL have antitumor effects particularly in vivo, whether they can reduce AXL expression levels, and whether they can suppress cancer.

PRIOR ART REFERENCES

Patent Documents

Patent Document 1: WO 2004/008147
Patent Document 2: WO 2007/114319
Patent Document 3: WO 2009/041643

Non-Patent Documents

Non-patent Document 1: O'Bryan et al., Mol Cell Biol 1991; 11: 5016-5031
Non-patent Document 2: Varnum et al., Nature 1995; 373: 623-626
Non-patent Document 3: Nakano et al., FEBS Lett 1996; 387: 78-80
Non-patent Document 4: Nakano et al., J Biol Chem 1995; 270: 5702-5705
Non-patent Document 5: Goruppi et al., Mol Cell Biol 1997; 17: 4442-4453
Non-patent Document 6: Bellosta et al., Oncogene 1997; 15: 2387-2397
Non-patent Document 7: Stenhoff et al., Biochem Biophys Res Commun 2004; 319: 871-878
Non-patent Document 8: Sainaghi et al., J Cell Physiol 2005; 204: 36-44
Non-patent Document 9: Sawabu et al., Mol Carcinog 2007; 46: 155-164
Non-patent Document 10: Fridell et al., J Biol Chem 1998; 273: 7123-7126
Non-patent Document 11: Allen et al., Mol Cell Biol 2002; 22: 599-613
Non-patent Document 12: McCloskey et al., J Biol Chem 1997; 272: 23285-23291
Non-patent Document 13: Hafizi et al., Biochem Biophys Res Commun 2002; 299: 793-800
Non-patent Document 14: Budagian et al., Embo J 2005; 24: 4260-4270
Non-patent Document 15: Vajkoczy P et al., Proc Natl Acad Sci USA 2006; 103: 5799-5804
Non-patent Document 16: Yamagata et al., Curr. Opin. Cell Biol 2003; 15: 621-632
Non-patent Document 17: Shieh et al., Neoplasia 2005; 7: 1058-1064
Non-patent Document 18: Meric et al., Clin Cancer Res 2002; 8: 361-367
Non-patent Document 19: Sun et al., Oncology 2004; 66: 450-457
Non-patent Document 20: Ito et al., Thyroid 2002; 12: 971-975
Non-patent Document 21: Chung et al., DNA Cell Biol 2003; 22: 533-540
Non-patent Document 22: Vajkoczy et al., Proc Natl Acad Sci USA 2006; 103: 5799-5804
Non-patent Document 23: Nemoto et al., Pathobiology 1997; 65: 195-203
Non-patent Document 24: Craven et al., Int J Cancer 1995; 60: 791-797
Non-patent Document 25: Neubauer et al., Blood 1994; 84: 1931-1941
Non-patent Document 26: Holland et al., Cancer Res 2005; 65: 9294-9303
Non-patent Document 27: Pavlaki et al., Cancer Metastasis Rev. 2003; 22: 177-203
Non-patent Document 28: Vaisitti et al., J Biol Regul Homeost Agents. 2005; 19: 105-12
Non-patent Document 29: Pardridge et al., J Pharmacol Exp Ther. 1998; 286: 548-54

SUMMARY OF THE INVENTION

Problems to be Solved by the Invention

An objective of the present invention is to provide anti-anexelekto (AXL) antibodies, and anticancer agents comprising the antibodies as an active ingredient. More specifically, an objective of the present invention is to decrease immunogenicity in humans by humanizing the mouse-derived anti-AXL antibodies.

Means for Solving the Problems

The present inventors discovered that certain types of antibodies that bind to AXL have actions of decreasing AXL expression level in vitro, and antitumor activity in vivo. Furthermore, antibodies that bind to FND1 domain of AXL were found to have stronger antitumor activity than antibodies that bind to other AXL domains.

Furthermore, the present inventors succeeded in obtaining humanized anti-AXL antibodies by humanizing the obtained anti-AXL antibodies described above.

These humanized antibodies are expected to have decreased immunogenicity in humans than mouse-derived anti-AXL antibodies.

More specifically, the present invention relates to the following:

[1] an antibody that recognizes FND1 domain of AXL, which is an antibody of any one of (1) to (6) below:

(1) an antibody comprising a heavy chain variable region comprising a CDR1 comprising the amino acid sequence of any one of SEQ ID NOs: 33 to 37, a CDR2 comprising the amino acid sequence of any one of SEQ ID NOs: 38 to 48, and a CDR3 comprising the amino acid sequence of SEQ ID NO: 49;

(2) an antibody comprising a heavy chain variable region of SEQ ID NO: 2 (H0);

(3) an antibody comprising a light chain variable region comprising a CDR1 comprising the amino acid sequence of any one of SEQ ID NOs: 84 to 89, a CDR2 comprising the amino acid sequence of SEQ ID NO: 90, and a CDR3 comprising the amino acid sequence of SEQ ID NO: 91;

(4) an antibody comprising a light chain variable region of SEQ ID NO: 65 (L0);

(5) an antibody comprising the heavy chain variable region of (1) and the light chain variable region of (3); and (6) an antibody having one or more amino acid substitutions, deletions, additions, and/or insertions in the antibody of any one of (1) to (5), which has equivalent activity as the antibody of any one of (1) to (5);

[2] a humanized antibody that recognizes FND1 domain of AXL, which is an antibody of any one of (1) to (6) below:

(1) an antibody comprising a heavy chain variable region comprising a CDR1 comprising the amino acid sequence of any one of SEQ ID NOs: 33 to 37, a CDR2 comprising the amino acid sequence of any one of SEQ ID NOs: 38 to 48, and a CDR3 comprising the amino acid sequence of SEQ ID NO: 49, as well as an FR1 comprising the amino acid sequence of SEQ ID NO: 51, an FR2 comprising the amino acid sequence of SEQ ID NO: 53, an FR3 comprising the amino acid sequence of SEQ ID NO: 109 or 58, and an FR4 comprising the amino acid sequence of SEQ ID NO: 61;

(2) an antibody comprising the heavy chain variable region of SEQ ID NO: 2 (H0);

(3) an antibody comprising a light chain variable region comprising a CDR1 comprising the amino acid sequence of any one of SEQ ID NOs: 84 to 89, a CDR2 comprising the amino acid sequence SEQ ID NO: 90, and a CDR3 comprising the amino acid sequence of SEQ ID NO: 91, as well as an FR1 comprising the amino acid sequence of SEQ ID NO: 93, an FR2 comprising the amino acid sequence of SEQ ID NO: 96, an FR3 comprising the amino acid sequence of SEQ ID NO: 101, and an FR4 comprising the amino acid sequence of SEQ ID NO: 103;
(4) an antibody comprising the light chain variable region of SEQ ID NO: 65 (L0);
(5) an antibody comprising the heavy chain variable region of (1) and the light chain variable region of (3); and
(6) an antibody having one or more amino acid substitutions, deletions, additions, and/or insertions in the antibody of any one of (1) to (5), which has equivalent activity as the antibody of any one of (1) to (5);
[3] the antibody of [1] or [2], wherein the amino acid residue at position 94 by Kabat numbering in the heavy chain variable region is glycine;
[4] the antibody of any one of [1] to [3], wherein the amino acid sequence of the heavy chain variable region comprises at least one of the following amino acid residues:
(1) the amino acid residue at position 31 by Kabat numbering in the heavy chain variable region is aspartic acid, glutamic acid, lysine, or arginine;
(2) the amino acid residue at position 40 by Kabat numbering in the heavy chain variable region is proline;
(3) the amino acid residue at position 41 by Kabat numbering in the heavy chain variable region is arginine;
(4) the amino acid residue at position 43 by Kabat numbering in the heavy chain variable region is glutamine or glutamic acid;
(5) the amino acid residue at position 44 by Kabat numbering in the heavy chain variable region is arginine;
(6) the amino acid residue at position 48 by Kabat numbering in the heavy chain variable region is isoleucine;
(7) the amino acid residue at position 61 by Kabat numbering in the heavy chain variable region is glutamic acid, lysine, or arginine;
(8) the amino acid residue at position 62 by Kabat numbering in the heavy chain variable region is glutamic acid;
(9) the amino acid residue at position 64 by Kabat numbering in the heavy chain variable region is glutamine;
(10) the amino acid residue at position 65 by Kabat numbering in the heavy chain variable region is aspartic acid;
(11) the amino acid residue at position 73 by Kabat numbering in the heavy chain variable region is asparagine; and
(12) the amino acid residue at position 105 by Kabat numbering in the heavy chain variable region is glutamic acid or arginine;
[5] the antibody of any one of [1] to [3], wherein the amino acid sequence of the heavy chain variable region comprises at least one of the following amino acid residues:
(1) the amino acid residue at position 41 by Kabat numbering in the heavy chain variable region is arginine;
(2) the amino acid residue at position 43 by Kabat numbering in the heavy chain variable region is glutamine;
(3) the amino acid residue at position 44 by Kabat numbering in the heavy chain variable region is arginine;
(4) the amino acid residue at position 61 by Kabat numbering in the heavy chain variable region is arginine; and
(5) the amino acid residue at position 73 by Kabat numbering in the heavy chain variable region is asparagine;
[6] the antibody of any one of [1] to [5], wherein the amino acid sequence of the light chain variable region comprises at least one of the following amino acid residues:
(1) the amino acid residue at position 17 by Kabat numbering in the light chain variable region is arginine;
(2) the amino acid residue at position 24 by Kabat numbering in the light chain variable region is glutamine;
(3) the amino acid residue at position 27 by Kabat numbering in the light chain variable region is glutamic acid or arginine;
(4) the amino acid residue at position 29 by Kabat numbering in the light chain variable region is alanine;
(5) the amino acid residue at position 42 by Kabat numbering in the light chain variable region is glutamic acid or glutamine;
(6) the amino acid residue at position 45 by Kabat numbering in the light chain variable region is lysine;
(7) the amino acid residue at position 100 by Kabat numbering in the light chain variable region is arginine;
(8) the amino acid residue at position 104 by Kabat numbering in the light chain variable region is valine; and
(9) the amino acid residue at position 107 by Kabat numbering in the light chain variable region is glutamic acid;
[7] the antibody of any one of [1] to [5], wherein the amino acid sequence of the light chain variable region comprises at least one of the following amino acid residues:
(1) the amino acid residue at position 17 by Kabat numbering in the light chain variable region is arginine;
(2) the amino acid residue at position 24 by Kabat numbering in the light chain variable region is glutamine;
(3) the amino acid residue at position 27 by Kabat numbering in the light chain variable region is arginine;
(4) the amino acid residue at position 29 by Kabat numbering in the light chain variable region is alanine;
(5) the amino acid residue at position 45 by Kabat numbering in the light chain variable region is lysine;
(6) the amino acid residue at position 100 by Kabat numbering in the light chain variable region is arginine;
(7) the amino acid residue at position 104 by Kabat numbering in the light chain variable region is valine; and
(8) the amino acid residue at position 107 by Kabat numbering in the light chain variable region is glutamic acid;
[8] the antibody of any one of [1] to [5], comprising at least any one of the following heavy chain variable regions:
(1) a heavy chain variable region comprising a CDR1 comprising the amino acid sequence of SEQ ID NO: 33, a CDR2 comprising the amino acid sequence of SEQ ID NO: 38, and a CDR3 comprising the amino acid sequence of SEQ ID NO: 49;
(2) a heavy chain variable region comprising a CDR1 comprising the amino acid sequence of SEQ ID NO: 34, a CDR2 comprising the amino acid sequence of SEQ ID NO: 38, and a CDR3 comprising the amino acid sequence of SEQ ID NO: 49;
(3) a heavy chain variable region comprising a CDR1 comprising the amino acid sequence of SEQ ID NO: 35, a CDR2 comprising the amino acid sequence of SEQ ID NO: 38, and a CDR3 comprising the amino acid sequence of SEQ ID NO: 49;
(4) a heavy chain variable region comprising a CDR1 comprising the amino acid sequence of SEQ ID NO: 33, a CDR2 comprising the amino acid sequence of SEQ ID NO: 39, and a CDR3 comprising the amino acid sequence of SEQ ID NO: 49;
(5) a heavy chain variable region comprising a CDR1 comprising the amino acid sequence of SEQ ID NO: 33, a CDR2 comprising the amino acid sequence of SEQ ID NO: 40, and a CDR3 comprising the amino acid sequence of SEQ ID NO: 49;
(6) a heavy chain variable region comprising a CDR1 comprising the amino acid sequence of SEQ ID NO: 33, a CDR2 comprising the amino acid sequence of SEQ ID NO: 41, and a CDR3 comprising the amino acid sequence of SEQ ID NO: 49;
(7) a heavy chain variable region comprising a CDR1 comprising the amino acid sequence of SEQ ID NO: 33, a CDR2 comprising the amino acid sequence of SEQ ID NO: 42, and a CDR3 comprising the amino acid sequence of SEQ ID NO: 49;
(8) a heavy chain variable region comprising a CDR1 comprising the amino acid sequence of SEQ ID NO: 33, a CDR2 comprising the amino acid sequence of SEQ ID NO: 43, and a CDR3 comprising the amino acid sequence of SEQ ID NO: 49;
(9) a heavy chain variable region comprising a CDR1 comprising the amino acid sequence of SEQ ID NO: 33, a CDR2 comprising the amino acid sequence of SEQ ID NO: 44, and a CDR3 comprising the amino acid sequence of SEQ ID NO: 49;
(10) a heavy chain variable region comprising a CDR1 comprising the amino acid sequence of SEQ ID NO: 33, a CDR2 comprising the amino acid sequence of SEQ ID NO: 45, and a CDR3 comprising the amino acid sequence of SEQ ID NO: 49;
(11) a heavy chain variable region comprising a CDR1 comprising the amino acid sequence of SEQ ID NO: 33, a CDR2 comprising the amino acid sequence of SEQ ID NO: 46, and a CDR3 comprising the amino acid sequence of SEQ ID NO: 49;
(12) a heavy chain variable region comprising a CDR1 comprising the amino acid sequence of SEQ ID NO: 36, a CDR2 comprising the amino acid sequence of SEQ ID NO: 38, and a CDR3 comprising the amino acid sequence of SEQ ID NO: 49;
(13) a heavy chain variable region comprising a CDR1 comprising the amino acid sequence of SEQ ID NO: 37, a CDR2 comprising the amino acid sequence of SEQ ID NO: 38, and a CDR3 comprising the amino acid sequence of SEQ ID NO: 49;
(14) a heavy chain variable region comprising a CDR1 comprising the amino acid sequence of SEQ ID NO: 33, a CDR2 comprising the amino acid sequence of SEQ ID NO: 47, and a CDR3 comprising the amino acid sequence of SEQ ID NO: 49; and
(15) a heavy chain variable region comprising a CDR1 comprising the amino acid sequence of SEQ ID NO: 33, a CDR2 comprising the amino acid sequence of SEQ ID NO: 48, and a CDR3 comprising the amino acid sequence of SEQ ID NO: 49;
[9] the antibody of any one of [1] to [7], which is selected from the group consisting of (1) to (25) below:
(1) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 84, 90, and 91, respectively;
(2) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 85, 90, and 91, respectively;
(3) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 86, 90, and 91, respectively;
(4) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 87, 90, and 91, respectively;
(5) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 88, 90, and 91, respectively;
(6) an antibody comprising a heavy chain variable region comprising CDRs 1, 2, and 3 comprising the amino acid sequences of SEQ ID NOs: 34, 38, and 49, respectively, and a light chain variable region comprising CDRs 1, 2, and 3 comprising the amino acid sequences of SEQ ID NOs: 84, 90, and 91, respectively;
(7) an antibody comprising a heavy chain variable region comprising CDRs 1, 2, and 3 comprising the amino acid sequences of SEQ ID NOs: 35, 38, and 49, respectively, and a light chain variable region comprising CDRs 1, 2, and 3 comprising the amino acid sequences of SEQ ID NOs: 84, 90, and 91, respectively;
(8) an antibody comprising a heavy chain variable region comprising CDRs 1, 2, and 3 comprising the amino acid sequences of SEQ ID NOs: 33, 39, and 49, respectively, and a light chain variable region comprising CDRs 1, 2, and 3 comprising the amino acid sequences of SEQ ID NOs: 84, 90, and 91, respectively;
(9) an antibody comprising a heavy chain variable region comprising CDRs 1, 2, and 3 comprising the amino acid sequences of SEQ ID NOs: 33, 40, and 49, respectively, and a light chain variable region comprising CDRs 1, 2, and 3 comprising the amino acid sequences of SEQ ID NOs: 84, 90, and 91, respectively;
(10) an antibody comprising a heavy chain variable region comprising CDRs 1, 2, and 3 comprising the amino acid sequences of SEQ ID NOs: 33, 41, and 49, respectively, and a light chain variable region comprising CDRs 1, 2, and 3 comprising the amino acid sequences of SEQ ID NOs: 84, 90, and 91, respectively;
(11) an antibody comprising a heavy chain variable region comprising CDRs 1, 2, and 3 comprising the amino acid sequences of SEQ ID NOs: 33, 42, and 49, respectively, and a light chain variable region comprising CDRs 1, 2, and 3 comprising the amino acid sequences of SEQ ID NOs: 84, 90, and 91, respectively;
(12) an antibody comprising a heavy chain variable region comprising CDRs 1, 2, and 3 comprising the amino acid sequences of SEQ ID NOs: 33, 43, and 49, respectively, and a light chain variable region comprising CDRs 1, 2, and 3 comprising the amino acid sequences of SEQ ID NOs: 84, 90, and 91, respectively;
(13) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 84, 90, and 91, respectively;
(14) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 85, 90, and 91, respectively;
(15) an antibody comprising a heavy chain variable region comprising CDRs 1, 2, and 3 comprising the amino acid sequences of SEQ ID NOs: 33, 45, and 49, respectively, and a light chain variable region comprising CDRs 1, 2, and 3 comprising the amino acid sequences of SEQ ID NOs: 84, 90, and 91, respectively;
(16) an antibody comprising a heavy chain variable region comprising CDRs 1, 2, and 3 comprising the amino acid sequences of SEQ ID NOs: 33, 46, and 49, respectively, and a light chain variable region comprising CDRs 1, 2, and 3 comprising the amino acid sequences of SEQ ID NOs: 84, 90, and 91, respectively;
(17) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 89, 90, and 91, respectively;
(18) an antibody comprising a heavy chain variable region comprising CDRs 1, 2, and 3 comprising the amino acid sequences of SEQ ID NOs: 36, 38, and 49, respectively, and a light chain variable region comprising CDRs 1, 2, and 3 comprising the amino acid sequences of SEQ ID NOs: 84, 90, and 91, respectively;
(19) an antibody comprising a heavy chain variable region comprising CDRs 1, 2, and 3 comprising the amino acid sequences of SEQ ID NOs: 37, 38, and 49, respectively, and a light chain variable region comprising CDRs 1, 2, and 3 comprising the amino acid sequences of SEQ ID NOs: 84, 90, and 91, respectively;
(20) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 84, 90, and 91, respectively;
(21) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 84, 90, and 91, respectively;
(22) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 85, 90, and 91, respectively;
(23) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 87, 90, and 91, respectively;
(24) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 85, 90, and 91, respectively; and
(25) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 87, 90, and 91, respectively;
[10] the antibody of [1] or [2] comprising the heavy chain variable region of any one of SEQ ID NOs: 2 to 32, and the light chain variable region of any one of SEQ ID NOs: 65 to 83;
[11] a chimeric antibody comprising the heavy chain variable region of SEQ ID NO: 1, the light chain variable region of SEQ ID NO: 64, and human antibody-derived constant regions, or the antibody of [1] having one or more amino acid substitutions, deletions, additions, and/or insertions in the chimeric antibody, which has equivalent activity as the chimeric antibody;
[12] the antibody of any one of [1] to [11], wherein the amino acid residue at position 42 by Kabat numbering in the amino acid sequence of the light chain variable region is lysine;
[13] a pharmaceutical composition comprising the antibody of any one of [1] to [12] as an active ingredient;
[14] an anticancer agent comprising the antibody of any one of [1] to [12] as an active ingredient;
[15] the anticancer agent of [14] wherein the cancer is pancreatic cancer, gastric cancer, lung cancer, osteosarcoma, colon cancer, prostate cancer, melanoma, endometrial cancer, ovarian cancer, uterine leiomyoma, thyroid cancer, cancer stem cell, breast cancer, bladder cancer, renal cancer, glioma, neuroblastoma, or esophageal cancer;
[16] the anticancer agent of [14], wherein the cancer is glioma, gastric cancer, endometrial cancer, non-small-cell lung cancer, pancreatic adenocarcinoma, or breast cancer; and
[17] the anticancer agent of [14], wherein the cancer is pancreatic adenocarcinoma or breast cancer.

The present invention further provides the following:
[18] a method of treating cancer, comprising a step of administering the antibody of any one of [1] to [12] to a subject (for example, a mammal such as a human); and
[19] use of the antibody of any one of [1] to [12] in the manufacture of an anticancer agent.

The hybridoma (Accession No. FERM BP-10854) selected by the present inventors was deposited at the International Patent Organism Depositary of the National Institute of Advanced Industrial Science and Technology. The following section provides a description of the contents, specifying the deposition.
(a) Name and Address of the Depositary Institution
　Name: International Patent Organism Depositary, National Institute of Advanced Industrial Science and Technology
　Address: Tsukuba Central 6, 1-1-1 Higashi, Tsukuba, Ibaraki, Japan 305-8566
(b) Acceptance Date (Deposition Date): Jul. 5, 2007
(c) Accession No.
　AXL No. 225 #070402 (Ax225) (Accession No. FERM BP-10854)

The amino acid sequences of the heavy chain variable region and the light chain variable region of the antibody produced by the hybridoma are shown in SEQ ID NO: 1 and SEQ ID NO: 64, respectively. The amino acid sequences of the heavy chain variable region CDR1, CDR2, CDR3, FR1, FR2, FR3, and FR4 are shown in SEQ ID NO: 33, SEQ ID NO: 38, SEQ ID NO: 49, SEQ ID NO: 50, SEQ ID NO: 52, SEQ ID NO: 57, and SEQ ID NO: 60, respectively. The amino acid sequences of the light chain variable region CDR1, CDR2, CDR3, FR1, FR2, FR3, and FR4 are shown in SEQ ID NO: 84, SEQ ID NO: 90, SEQ ID NO: 91, SEQ ID NO: 92, SEQ ID NO: 95, SEQ ID NO: 100, and SEQ ID NO: 102, respectively.

Preferred antibody heavy chain variable regions and light chain variable regions of the present invention as well as the amino acid sequences of their CDR1, CDR2, CDR3, FR1, FR2, FR3, and FR4, and their corresponding SEQ ID NOs are shown in Table 1 and Table 2.

TABLE 1

| HEAVY CHAIN | FULL LENGTH OF VARIABLE REGION | CDR1 | CDR2 | CDR3 | FR1 | FR2 | FR3 | FR4 |
|---|---|---|---|---|---|---|---|---|
| chH | 1 | 33 | 38 | 49 | 50 | 52 | 57 | 60 |
| H0 | 2 | 33 | 38 | 49 | 51 | 53 | 58 | 61 |
| H9 | 3 | 33 | 38 | 49 | 51 | 53 | 59 | 61 |
| H17 | 4 | 34 | 38 | 49 | 51 | 53 | 59 | 61 |
| H18 | 5 | 35 | 38 | 49 | 51 | 53 | 59 | 61 |
| H19 | 6 | 33 | 38 | 49 | 51 | 54 | 59 | 61 |
| H20 | 7 | 33 | 38 | 49 | 51 | 55 | 59 | 61 |
| H21 | 8 | 33 | 39 | 49 | 51 | 53 | 59 | 61 |
| H22 | 9 | 33 | 40 | 49 | 51 | 53 | 59 | 61 |
| H23 | 10 | 33 | 41 | 49 | 51 | 53 | 59 | 61 |
| H24 | 11 | 33 | 42 | 49 | 51 | 53 | 59 | 61 |
| H25 | 12 | 33 | 43 | 49 | 51 | 53 | 59 | 61 |
| H26 | 13 | 33 | 44 | 49 | 51 | 53 | 59 | 61 |
| H26 | 13 | 33 | 44 | 49 | 51 | 53 | 59 | 61 |
| H26 | 13 | 33 | 44 | 49 | 51 | 53 | 59 | 61 |
| H26 | 13 | 33 | 44 | 49 | 51 | 53 | 59 | 61 |
| H26 | 13 | 33 | 44 | 49 | 51 | 53 | 59 | 61 |
| H27 | 14 | 33 | 45 | 49 | 51 | 53 | 59 | 61 |
| H28 | 15 | 33 | 46 | 49 | 51 | 53 | 59 | 61 |
| H30 | 16 | 33 | 38 | 49 | 51 | 53 | 59 | 62 |
| H31 | 17 | 33 | 44 | 49 | 51 | 54 | 59 | 61 |
| H32 | 18 | 33 | 44 | 49 | 51 | 53 | 59 | 62 |
| H33 | 19 | 33 | 44 | 49 | 51 | 54 | 59 | 62 |
| H34 | 20 | 36 | 38 | 49 | 51 | 53 | 59 | 61 |
| H35 | 21 | 37 | 38 | 49 | 51 | 53 | 59 | 61 |
| H36 | 22 | 33 | 38 | 49 | 51 | 56 | 59 | 61 |
| H37 | 23 | 33 | 47 | 49 | 51 | 53 | 59 | 61 |
| H38 | 24 | 33 | 48 | 49 | 51 | 53 | 59 | 61 |
| H39 | 25 | 33 | 38 | 49 | 51 | 53 | 59 | 63 |
| H40 | 26 | 36 | 38 | 49 | 51 | 56 | 59 | 61 |
| H41 | 27 | 37 | 38 | 49 | 51 | 56 | 59 | 61 |
| H46 | 28 | 33 | 48 | 49 | 51 | 56 | 59 | 61 |
| H47 | 29 | 33 | 47 | 49 | 51 | 56 | 59 | 61 |
| H48 | 30 | 33 | 38 | 49 | 51 | 56 | 59 | 63 |
| H49 | 31 | 33 | 48 | 49 | 51 | 56 | 59 | 63 |
| H50 | 32 | 33 | 47 | 49 | 51 | 56 | 59 | 63 |

TABLE 2

| LIGHT CHAIN | FULL LENGTH OF VARIABLE REGION | CDR1 | CDR2 | CDR3 | FR1 | FR2 | FR3 | FR4 |
|---|---|---|---|---|---|---|---|---|
| chL | 64 | 84 | 90 | 91 | 92 | 95 | 100 | 102 |
| L0 | 65 | 84 | 90 | 91 | 93 | 96 | 101 | 103 |
| L1 | 66 | 85 | 90 | 91 | 93 | 96 | 101 | 103 |
| L3 | 67 | 86 | 90 | 91 | 93 | 96 | 101 | 103 |
| L4 | 68 | 84 | 90 | 91 | 93 | 97 | 101 | 103 |
| L5 | 69 | 84 | 90 | 91 | 93 | 98 | 101 | 103 |
| L10 | 70 | 84 | 90 | 91 | 93 | 96 | 101 | 104 |
| L11 | 71 | 85 | 90 | 91 | 93 | 96 | 101 | 104 |
| L12 | 72 | 85 | 90 | 91 | 93 | 97 | 101 | 104 |
| L13 | 73 | 85 | 90 | 91 | 93 | 98 | 101 | 104 |
| L21 | 83 | 89 | 90 | 91 | 93 | 96 | 101 | 104 |
| L25 | 74 | 84 | 90 | 91 | 94 | 96 | 101 | 103 |
| L27 | 75 | 87 | 90 | 91 | 93 | 96 | 101 | 103 |
| L28 | 76 | 84 | 90 | 91 | 93 | 99 | 101 | 103 |
| L29 | 77 | 84 | 90 | 91 | 93 | 96 | 101 | 105 |
| L31 | 78 | 87 | 90 | 91 | 93 | 99 | 101 | 103 |
| L34 | 79 | 87 | 90 | 91 | 94 | 99 | 101 | 103 |
| L35 | 80 | 87 | 90 | 91 | 93 | 99 | 101 | 105 |
| L36 | 81 | 88 | 90 | 91 | 93 | 96 | 101 | 103 |
| L37 | 82 | 87 | 90 | 91 | 94 | 99 | 101 | 105 |

An antibody having one or more amino acid substitutions, deletions, additions, and/or insertions in the amino acid sequence of any of the antibodies mentioned above, and having equivalent activity to that antibody is also within the scope of the present invention.

In the present invention "an antibody having equivalent activity" means, for example, "an antibody having at least equivalent binding activity or in vivo activity". Specifically, "an antibody having one or more amino acid substitutions, deletions, additions, and/or insertions in the amino acid sequence of H0 and/or L0, and having antigen binding activity or in vivo activity that is at least equivalent compared to the H0/L0 antibody" is also within the scope of the present invention. Herein, in vivo activity includes antitumor activity and such in in vivo examinations. Specifically, the examinations include mouse xenograft model examinations employed in Example 6 of the present application.

Preferably, antibodies of the present invention are humanized antibodies that bind to the FND1 domain of AXL. That is, in another perspective, the present invention provides humanized antibodies that bind to AXL.

Furthermore, in another perspective, the present invention provides pharmaceutical compositions comprising any of the above-mentioned antibodies of the present invention. Preferably, the pharmaceutical compositions are anticancer agents.

Moreover, in another perspective, the present invention provides agents that decrease the level of AXL expression and diagnostic agents comprising any of the above-mentioned antibodies of the present invention.

Effects of the Invention

In comparison to mouse-derived anti-AXL antibodies, these humanized antibodies are expected to have decreased immunogenicity in humans.

BRIEF DESCRIPTION OF THE DRAWINGS

FIG. 1 shows the antitumor activities and binding domains of anti-AXL antibodies. −: TGI (%)<30, +: TGI (%)<60, ++: 60=<TGI (%).

MODE FOR CARRYING OUT THE INVENTION

Humanized Antibodies

Figure 2:
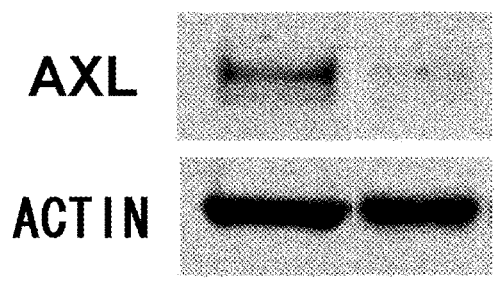
FIG. 2 shows photographs depicting the results of an experiment that evaluates the activity of Ax225 antibody to induce downmodulation of AXL in cancer cells. This antibody was shown to induce downmodulation of AXL protein.

An example of preferred embodiments of the antibodies of the present invention is a humanized antibody that binds to AXL. Humanized antibodies can be produced using known methods. Humanized antibodies are also called reshaped human antibodies.

In the present invention, a humanized antibody is composed of complementarity determining regions (CDRs) of a non-human animal-derived antibody, human antibody-derived framework regions (FRs), and human antibody-derived constant regions. Preferably, the non-human animal-derived antibody is Ax225 antibody (Application No. PCT/JP2008/070739) produced by the hybridoma deposited under Accession No. FERM BP-10854 (National Institute of Advanced Industrial Science and Technology, International Patent Organism Depository, Central 6, 1-1-1 Higashi, Tsukuba, Ibaraki, Japan, acceptance date (deposition date): Jul. 5, 2007). The method for obtaining Ax225 antibody is described in Referential Example 1. Binding of Ax225 antibody to the FND1 domain of the AXL is described in Referential Example 2. Referential Example 3 describes that Ax225 antibody has the activity of downmodulation of AXL.

Common genetic engineering techniques for producing humanized antibodies are also known (see EP Patent Application Publication No. EP 125023 and WO 96/02576). A humanized antibody is obtained by linking the obtained DNA to a DNA encoding a human antibody constant region or a modified human antibody constant region, then incorporating this into an expression vector, and transfecting the vector into a host to produce antibodies (see EP Patent Application Publication No. EP 239400 and WO 96/02576).

The humanized Ax225 antibody, a conjugate of the CDR regions of Ax225 antibody and the framework regions (FRs) of a human antibody, can be produced as follows. First, respective variable region sequences of the heavy chain (H chain) and the light chain (L chain) of humanized Ax225 antibody are designed, and several synthetic oligo-DNA fragments encoding these regions are designed. These oligo-DNA fragments are fused by assembly PCR to produce a gene encoding the full length of the variable regions (see the method described in WO 98/13388).

For the human antibody framework regions which will be fused with CDRs, those that will allow the CDRs to form favorable antigen binding sites will be selected. When necessary, amino acid substitutions, deletions, additions, and/or insertions can be carried out on the framework regions in the antibody variable regions.

Furthermore, the above-mentioned CDR sequences may have one or more amino acid substitutions, deletions, additions, and/or insertions. A CDR sequence that has undergone one or more amino acid substitutions, deletions, additions, and/or insertions preferably has equivalent or better properties as compared to the CDR sequence before modification in terms of binding activity, neutralizing activity, stability, immunogenicity, and/or pharmacokinetics. The number of amino acids that are substituted, deleted, added, and/or inserted is not particularly limited, but is preferably three amino acids or less per CDR, more preferably two amino acids or less, and more preferably one amino acid.

Amino acid substitutions, deletions, additions, and/or insertions can be carried out by the above-described methods.

A constant region used in the antibodies of the present invention is not particularly limited, and any constant region may be used. Preferred examples of the constant region to be used in the antibodies of the present invention include human antibody-derived constant regions (for example, C$\gamma$1, C$\gamma$2, C$\gamma$3, C$\gamma$4, C$\mu$, C$\delta$, C$\alpha$1, C$\alpha$2, and C$\epsilon$ for the H chain, and C$\kappa$, C$\lambda$, and such for the L chain). Particularly preferred examples of natural human antibody constant regions include constant regions derived from IgG1, IgG2, or IgG4.

When the antibody constant region of the present invention originates from IgG1, the antibody antitumor effect of the present invention which will be mentioned later is expected to be enhanced by its ADCC and CDC.

When the antibody constant region of the present invention originates from IgG4, the side effects of the antibody of the present invention are expected to be reduced.

Furthermore, a human antibody-derived constant region may have one or more amino acid substitutions, deletions, additions, and/or insertions for the purpose of decreasing heterogeneity, enhancing ADCC, prolonging half-life in plasma, and such. Herein, one or more amino acids are for example, 30 amino acids or less, preferably 15 amino acids or less, more preferably 10 amino acids or less, and particularly preferably two amino acids or less.

The antibodies of the present invention include not only bivalent antibodies represented by IgG, but also monovalent antibodies, or polyvalent antibodies represented by IgM, as long as they have binding activity and/or neutralizing activity against the AXL (preferably the FND1 domain). The polyvalent antibodies of the present invention include polyvalent antibodies having antigen binding sites which are all the same, and polyvalent antibodies having antigen binding sites which are partly or all different. The antibodies of the present invention are not limited to whole antibody molecules, and may be minibodies (low-molecular-weight antibodies) or their variants as long as they bind to the AXL.

The minibodies are antibodies that include an antibody fragment wherein a part of a whole antibody (for example, whole IgG) is missing, and they are not particularly limited as long as they have binding activity and/or neutralizing activity against AXL. The minibodies of the present invention are not particularly limited so long as they include a part of a whole antibody, but preferably include either VH or VL, and particularly preferably include both VH and VL. Another preferred example of the minibodies of the present invention includes minibodies comprising antibody CDRs. The CDRs included in the minibodies may be all six CDRs of the antibody or some of the CDRs.

The minibodies of the present invention preferably have a smaller molecular weight compared to the whole antibody; however, they may form multimers such as a dimer, trimer, or tetramer, and their molecular weight may become larger than the whole antibody.

Specific examples of antibody fragments include, for example, Fab, Fab', F(ab')2, and Fv. Specific examples of minibodies (low molecular weight antibodies) include Fab, Fab', F(ab')2, Fv, scFv (single-chain Fv), diabody, sc(Fv)2 (single-chain (Fv)2), etc. Polymers (such as dimers, trimers, tetramers, or polymers) of these antibodies are also included in the minibodies of the present invention.

Antibody fragments can be obtained by producing an antibody fragment by treating the antibody with an enzyme. Known examples of enzymes used to produce antibody fragments include papain, pepsin, plasmin, etc. Alternatively, genes encoding these antibody fragments can be constructed, introduced into an expression vector, and then expressed in suitable host cells (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

Digestive enzymes cleave a specific position of an antibody fragment to yield an antibody fragment with a specific structure, as indicated below. An arbitrary portion of an antibody can be deleted by applying genetic engineering techniques to an antibody fragment enzymatically obtained in this manner.

Antibody fragments obtainable by using the digestive enzymes mentioned above are as follows:
Papain digestion: F(ab)2 or Fab
Pepsin digestion: F(ab')2 or Fab'
Plasmin digestion: Facb As long as they have an AXL binding activity and/or neutralizing activity, minibodies of the present invention can include antibody fragments having a deletion of an arbitrary region.

"Diabody" refers to bivalent minibodies constructed by gene fusion (see Holliger, P. et al., Proc. Natl. Acad. Sci. U.S.A. (1993) 90, 6444-6448; EP 404,097; WO 93/11161, etc.). Diabodies are dimers composed of two polypeptide chains. Normally, VL and VH within the same chain of the polypeptide chains that forms a dimer are both bound by linkers. The linkers of the polypeptides in a diabody are typically too short to allow the VL and VH to bind to each other. Specifically, the number of amino acid residues that constitute a linker is preferably 2 to 12 residues, more preferably 3 to 10 residues, and particularly about five residues. Thus, the VL and VH encoded in the same polypeptide chain cannot form a single-chain variable region fragment, but instead form a dimer with a different single-chain variable region fragment. As a result, a diabody has two antigen-binding sites.

An scFv is an antibody of a single-chain polypeptide obtained by linking VH and VL through a linker or such (Huston, J. S. et al., Proc. Natl. Acad. Sci. U.S.A. (1988) 85, 5879-5883; and Plickthun, "The Pharmacology of Monoclonal Antibodies" Vol. 113, Ed Resenburg and Moore, Springer Verlag, New York, pp. 269-315, (1994)). The H chain V region and L chain V region in an scFv may be derived from any antibody described herein. There is no particular limitation on the peptide linkers that link the V regions. For example, any arbitrary single-chain peptide comprising about three to 25 residues can be used as a linker. Specifically, for example, peptide linkers which are mentioned below may be used.

The V regions of both chains can be linked by, for example, the PCR method described above. To link the V regions using the PCR method, a DNA encoding the entire or desired partial amino acid sequence of the DNAs below are used as templates.

a DNA sequence encoding the H chain or the H chain V region of the antibody, and
a DNA sequence encoding the L chain or the L chain V region of the above antibody Each DNA encoding the V regions of the H chain or L chain is amplified by the PCR method using pairs of primers with sequences corresponding to the sequences at both ends of the DNA to be amplified. Next, a DNA encoding the peptide linker portion is prepared. The DNA encoding the peptide linker can also be synthesized by PCR. Nucleotide sequences that can link the amplification products of each separately synthesized V region are added to the 5' side of the primers used at this time. Next, a PCR reaction is carried out using the "H chain V region DNA", the "peptide linker DNA", and the "L chain V region DNA" together with the primers for the assembly PCR.

The primers for the assembly PCR consist of a combination of a primer that anneals to the 5' side of the "H chain V region DNA" and a primer that anneals to the 3' side of the "L chain V region DNA". Therefore, the primers for the assembly PCR consist of a primer set that can amplify the DNA encoding the entire sequence of the scFv to be synthesized. Conversely, nucleotide sequences that can link to each V region DNA are added to the "peptide linker DNA". As a result, these DNAs are linked together and the full length of scFv is finally produced as an amplification product of the primers used for the assembly PCR. Once a DNA encoding an scFv is prepared, an expression vector comprising the DNA and recombinant cells transformed with the expression vector can be acquired with ordinary methods. The scFv can also be acquired by expressing the DNA encoding the scFv in cultures of the resulting recombinant cells.

The order of VHs and VLs to be linked is not particularly limited, and they may be arranged in any order. Examples of arrangements are listed below:
[VH] linker [VL]
[VL] linker [VH]

An sc(Fv)2 is a minibody in which two VHs and two VLs are linked by a linker or such to form a single chain (Hudson, et al., J. Immunol. Methods (1999) 231: 177-189). An sc(Fv)2 can be prepared, for example, by connecting scFvs with a linker.

The sc(Fv)2 of the present invention include antibodies preferably in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order. Examples of arrangements are listed below:
[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

The amino acid sequence of the VH or VL in the minibodies may include substitutions, deletions, additions, and/or insertions. Additionally, a part may be deleted or another polypeptide may be added as long as there is antigen binding activity when VH and VL are associated. Moreover, the variable region may be chimerized or humanized.

Any arbitrary peptide linker that can be introduced by genetic engineering, a synthetic compound linker (for example, those disclosed in Protein Engineering, (1996) 9 (3), 299-305) or such, can be used as the linker to link antibody variable regions in the present invention.

Peptide linkers are preferred in the present invention. There is no particular limitation on the length of the peptide linkers, and the length can be suitably selected by those skilled in the art according to the purpose of use. Normally, they are one to 100 amino acids, preferably from three to 50 amino acids, more preferably from five to 30 amino acids, and particularly preferably from 12 to 18 amino acids (for example, 15 amino acids).

For example, such peptide linkers include:

Ser

Gly Ser

Gly Gly Ser

Ser Gly Gly

Gly Gly Gly Ser           (SEQ ID NO: 110)

Ser Gly Gly Gly           (SEQ ID NO: 111)

Gly Gly Gly Gly Ser       (SEQ ID NO: 112)

Ser Gly Gly Gly Gly       (SEQ ID NO: 113)

Gly Gly Gly Gly Gly Ser   (SEQ ID NO: 114)

Ser Gly Gly Gly Gly Gly   (SEQ ID NO: 115)

Gly Gly Gly Gly Gly Gly Ser (SEQ ID NO: 116)

Ser Gly Gly Gly Gly Gly Gly (SEQ ID NO: 117)

-continued (Gly Gly Gly Gly Ser       (SEQ ID NO: 112))n (Ser Gly Gly Gly Gly       (SEQ ID NO: 113))n wherein n is an integer of one or more.

The amino acid sequence of the peptide linker can be suitably selected by those skilled in the art according to the objective. For example, n which determines the length of the peptide linker is ordinarily one to five, preferably one to three, and more preferably one or two.

A synthetic compound linker (chemical cross-linking agent) is cross-linking agents ordinarily used to cross-link peptides and such. Examples of cross-linking agents that are available on the market include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

Normally, three linkers are required when four antibody variable regions are linked. The multiple linkers used may be identical or different.

The antibodies of the present invention include antibodies with one or more amino acid residue additions in the amino acid sequence of the antibodies of the present invention. Furthermore, fusion proteins produced by fusing these antibodies with other peptides or proteins are also included. The fusion proteins can be produced by a method of fusing a polynucleotide encoding an antibody of the present invention and a polynucleotide encoding another peptide or polypeptide in-frame and inserting this into an expression vector, then expressing this in a host, and methods known to those skilled in the art may be used. Known peptides, for example, FLAG (Hopp, T. P. et al., BioTechnology (1988) 6: 1204-1210), 6×His containing six His (histidine) residues, 10×His, influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and such can be used as other peptides or polypeptides that are fused to the antibody of the present invention. Examples of other polypeptides that are fused to an antibody of the present invention are glutathione-S-transferase (GST), influenza agglutinin (HA), immunoglobulin constant region, β-galactosidase, maltose-binding protein (MBP), and such. Fusion polypeptides can be prepared by fusing a commercially available polynucleotide which encodes such a peptide or polypeptide with a polynucleotide encoding an antibody of the present invention, and by expressing the resulting fusion polynucleotide.

The antibodies of the present invention may be conjugated antibodies which are bound to various molecules including macromolecular substances such as polyethylene glycol (PEG) or hyaluronic acid, radioactive materials, fluorescent substances, luminescent substances, enzymes, and toxins. Such conjugated antibodies can be obtained by performing chemical modifications on obtained antibodies. Methods for modifying antibodies are already established in this field (for example, U.S. Pat. No. 5,057,313 and U.S. Pat. No. 5,156,840). The term "antibody" in the present invention also includes such conjugated antibodies.

The antibodies of the present invention also include antibodies with modified sugar chains. It is known that cytotoxic activity of antibodies can be enhanced by modifying the sugar chains of an antibody. Known examples of antibodies with modified sugar chains are the following:
glycosylated antibodies (for example, WO 99/54342);
antibodies deficient in fucose attached to sugar chains (for example, WO 00/61739 and WO 02/31140);
antibodies having a sugar chain with bisecting GlcNAc (for example, WO 02/79255), and such.

Furthermore, antibodies used in the present invention may be bispecific antibodies. Bispecific antibodies refer to antibodies that comprise within the same antibody molecule, variable regions recognizing different epitopes. In the present invention, the bispecific antibodies may be those recognizing different epitopes on the AXL molecule, or alternatively, those in which one of the antigen binding sites recognizes AXL, and the other antigen binding site recognizes another substance. Furthermore, from a different perspective, they may be bispecific antibodies in which one of the antigen binding sites recognizes AXL, and the other antigen binding site recognizes an antigen on human effector cells. Examples of antigens bound by the other antigen binding site of bispecific, AXL-recognizing antibody of the present invention include CD2, CD3, CD16, CD19, CD20, CD25, CD28, CD33, CD30, CD44, CD44v6, CD52, VEGF, VEGFR, EGF, EGFR, EGFRvIII, HER-2 neu, HER-3, HER-4, cMET, EpCAM, IGF-1R, TRAIL-R2, Tie-1, PDGFR-alpha, NKG2D, CCR5, Gas6, Mer, Tyro3, NCAM, Transferin receptor, Folate binding protein, IL-15, IL-15R, CEA, CA125, MUC-1, ganglioside GD3, Glypican-3, GM2, and Sonic Hedgehog (Shh).

Examples of the different epitopes on the AXL molecule bound by the other antigen binding site of bispecific, AXL-recognizing antibody of the present invention include IgD1, IgD2, and FND2.

Methods for producing bispecific antibodies are known. For example, a bispecific antibody can be produced by linking two types of antibodies that recognize different antigens. Each of the linked antibodies may be a half molecule, with the H and L chains, or a quarter molecule comprising only the H chain. Alternatively, fused cells that produce bispecific antibodies can be prepared by fusing hybridomas producing different monoclonal antibodies. Bispecific antibodies can also be prepared with genetic engineering techniques.

Antibodies of the present invention may differ in their amino acid sequences, molecular weights, isoelectric points, or the presence/absence or form of sugar chains depending on the later-described antibody-producing cells or hosts, or methods of purification. However, as long as the obtained antibodies have functions equivalent to the antibodies of the present invention, they are included in the present invention. For example, in some cases the amino acids included in the amino acid sequences described in the present invention are subjected to modification (for example, modification of the N-terminal glutamine to pyroglutamic acid by pyroglutamylation is a modification well known to those skilled in the art) after translation, but even when amino acids undergo post-translational modification in this manner, they are, as a matter of course, included in the amino acid sequences of the present invention. Furthermore, when an antibody of the present invention is expressed in prokaryotic cells such as *Escherichia coli*, a methionine residue is added to the N terminus of the amino acid sequence of the original antibody. Antibodies of the present invention also include such antibodies.

Polypeptides such as the anti-AXL antibodies of the present invention can be produced by methods known to those skilled in the art.

Anti-AXL antibodies can be prepared by a gene recombinant technique known to those skilled in the art based on a sequence of an anti-AXL antibody obtained, for example. Specifically, a polynucleotide encoding an antibody is constructed based on the sequence of an antibody that recognizes AXL, introduced into an expression vector, and then expressed in suitable host cells (see, for example, Co, M. S. et al., J. Immunol. (1994) 152, 2698-2976; Better, M. and Horwitz, A. H., Methods Enzymol. (1989) 178, 476-496; Plueckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

The vectors include, for example, M13-series vectors, pUC-series vectors, pBR322, pBluescript, and pCR-Script. When the purpose is subcloning or excision of cDNAs, examples of vectors include pGEM-T, pDIRECT, and pT7 in addition to the above-mentioned vectors. When using vectors for the purpose of producing the antibodies of this invention, expression vectors are particularly useful. When the objective is to express the vector in *E. coli*, for example, the vector should have characteristics that will lead to amplification in *E. coli*. Additionally, when *E. coli* such as JM109, DH5α, HB101, or XL1-Blue is used as a host, the vector must have a promoter, for example, a lacZ promoter (Ward et al. Nature (1989) 341, 544-546; FASEB J. (1992) 6, 2422-2427), araB promoter (Better et al. Science (1988) 240, 1041-1043), or T7 promoter that can allow efficient expression in *E. coli*. Other examples of such vectors include pGEX-5X-1 (manufactured by Pharmacia), "QIAexpress system" (manufactured by QIAGEN), pEGFP, and pET (in this case, the host is preferably BL21 expressing T7 RNA polymerase).

Furthermore, the expression plasmid vector may comprise a signal sequence for antibody secretion. For production into the periplasm of *E. coli*, the pelB signal sequence (Lei, S. P. et al. J. Bacteriol. (1987) 169, 4379) may be used as the signal sequence for antibody secretion. For example, calcium chloride methods or electroporation methods may be used to introduce the vector into a host cell.

In addition to *E. coli*, a vector for producing an antibody of the present invention may be, for example, expression vectors derived from mammals (e.g., pcDNA3 (manufactured by Invitrogen), pEF-BOS (Nucleic Acids Res. 1990, 18 (17), p5322), pEF, pCDM8), expression vectors derived from insect cells (e.g., "Bac-to-BAC baculovirus expression system" (manufactured by GIBCO-BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIPneo), expression vectors derived from yeasts (e.g., "*Pichia* Expression Kit" (manufactured by Invitrogen), pNV11, SP-Q01), and expression vectors derived from *Bacillus subtilis* (e.g., pPL608, pKTH50).

When an objective is expression in animal cells such as CHO, COS, and NIH3T3 cells, the expression plasmid vector must have a promoter necessary for expression in the cells, for example, an SV40 promoter (Mulligan et al. Nature (1979) 277, 108), MMLV-LTR promoter, EF1α promoter (Mizushima et al. Nucleic Acids Res. (1990) 18, 5322), CMV promoter, etc. It is even more preferable that the vector also carries a gene for selecting transformants (for example, a drug-resistance gene enabling selection by a drug (neomycin, G418, or such)). Examples of vectors with such characteristics include pMAM, pDR2, pBK-RSV, pBK-CMV, pOPRSV, pOP13, and such.

In addition, when an objective is to stably express a gene and amplify the gene copy number in cells, a method can be adopted in which CHO cells with a defective nucleic acid synthesis pathway is introduced with a vector containing a DHFR gene (for example, pSV2-dhfr ("Molecular Cloning 2nd edition" Cold Spring Harbor Laboratory Press, (1989))) which complements the defect, and methotrexate (MTX) is used for amplification. Alternatively, when an objective is transient gene expression, a method can be used in which a COS cell, which carries an SV40 T antigen-expressing gene on its chromosome, is transformed with a vector containing the SV40 replication origin (for example, pcD). The replication origin used may be those derived from polyoma viruses, adenoviruses, bovine papilloma viruses (BPV), and such. Furthermore, to increase the gene copy number in host cell systems, the expression vector may contain, as a selection marker, an aminoglycoside transferase (APH) gene, thymidine kinase (TK) gene, $E.\ coli$ xanthine guanine phosphoribosyl transferase (Ecogpt) gene, dihydrofolate reductase (dhfr) gene, and such.

The resulting antibodies of the present invention may be isolated from the inside or outside (such as medium) of host cells, and purified as substantially pure and homogenous antibodies. Methods for isolation and purification commonly used for antibody purification may be used for the isolation and purification of antibodies, and they are not limited to any method. Antibodies may be isolated and purified by appropriately selecting and combining, for example, column chromatographies, filtration, ultrafiltration, salting out, solvent precipitation, solvent extraction, distillation, immunoprecipitation, SDS-polyacrylamide gel electrophoresis, isoelectric focusing, dialysis, and recrystallization.

Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). These chromatographies can be carried out using liquid phase chromatographies such as HPLC and FPLC. Columns used for affinity chromatography include protein A column and protein G column. Examples of columns using protein A column include Hyper D, POROS, and Sepharose FF (GE Healthcare Biosciences). The present invention also includes antibodies that are highly purified using these purification methods.

The AXL-binding activity of the obtained antibodies can be measured using methods known to those skilled in the art. For example, Biacore, ELISA (enzyme linked immunosorbent assay), EIA (enzyme immunoassay), RIA (radioimmunoassay), or fluoroimmunoassay may be used as the method for measuring antigen binding activity of antibodies. For example, when using enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Agents for Lowering the AXL Expression Level

The present invention also provides agents that lower the AXL expression level comprising an anti-AXL antibody. The agent that lowers the AXL expression level reduces AXL expression level in cells expressing AXL. There is no particular limitation on the cells that express AXL. Examples of these cells include cancer cells (Calu-1, MDA-MB-231, DU-145, etc.).

The reduction in the expression level of AXL may be a reduction in the amount of AXL already present by the degradation of AXL, or such, or may be a reduction in the amount of newly expressed AXL by suppressing the expression of AXL.

The agents that lower the AXL expression level comprising the anti-AXL antibody of the present invention can be expressed as methods for lowering the expression level of AXL using an anti-AXL antibody. Moreover, the agents that lower the AXL expression level comprising the anti-AXL antibody of the present invention can be expressed as a use of an anti-AXL antibody for producing an agent for lowering the AXL expression level.

The anti-AXL antibodies of the present invention are expected to exhibit angiogenesis inhibitory activity, tumor-growth-suppressive effect, and such by lowering AXL expression levels.

Pharmaceutical Compositions

The cell-growth suppressants or agents that lower the AXL expression level of the present invention can be administered by either oral administration methods or parenteral administration methods. Parenteral administration methods are particularly preferred. Specific examples of such administration methods include administration by injection, transnasal administration, transpulmonary administration, and transcutaneous administration. The pharmaceutical compositions of the present invention can be administered systemically or locally by injection, for example, by intravenous injection, intramuscular injection, intraperitoneal injection, subcutaneous injection, or such. Suitable methods of administration can also be selected according to the age and symptoms of the patient. The dosage can be selected, for example, within the range of 0.0001 mg to 1,000 mg per kilogram body weight per administration. Alternatively, the dosage can be selected, for example, within the range of 0.001 to 100,000 mg/body per patient. However, the dosage of the pharmaceutical compositions of the present invention is not limited thereto.

The cell-growth suppressants or agents for lowering the AXL expression level of the present invention can be formulated according to ordinary methods (for example, Remington's Pharmaceutical Science, latest edition, Mark Publishing Company, Easton, USA), and may comprise pharmaceutically acceptable carriers or additives. Examples of the carriers and additives include, but are not limited to, surfactants, vehicles, colorants, fragrances, preservatives, stabilizers, buffers, suspension agents, isotonic agents, binders, disintegration agents, lubricants, fluidity promoters, and flavoring agents. Other commonly used carriers can be used appropriately. Specific examples of such carriers include light silicic anhydride, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium-chain fatty-acid triglycerides, polyoxyethylene hydrogenated castor oil 60, saccharose, carboxymethyl cellulose, cornstarch, inorganic salts, etc.

All prior art reference cited herein are incorporated by reference in their entirety.

EXAMPLES

Although the present invention will be explained in more detail by the following Examples, the present invention is not limited by these Examples.

Referential Example 1

Method for Obtaining Ax225 Antibody 1-1. Preparation of Antigen

Hamster ovary cells (CHO (dhfr⁻) cells) were transfected with the expression vector for a fusion protein (hAXL-ECD-mIgG2aFc), in which the extracellular domain of human AXL and an Fc domain of mouse IgG2a were fused, and CHO cell lines that produce hAXL-ECD-mIgG2aFc protein were cloned with G418 selection. The culture supernatant of the hAXL-ECD-mIgG2aFc protein-producing CHO cell lines collected using serum-free medium (CHO-S-SFM II; Gibco) was added to a Protein G Column (HiTrap Protein G HP, GE Healthcare) equilibrated with a binding buffer (20 mM phosphate buffer, pH 7.0). After the unbound proteins were washed with the binding buffer, fractions of hAXL-ECD-mIgG2aFc protein were collected with an elution buffer (100 mM glycine-HCl, pH 2.7) into tubes containing neutralizing buffer (1 M Tris-HCl, pH 9.0). Then the buffer of the purified protein was replaced with phosphate-buffered physiological saline (pH 7.35-7.65; Takara Bio) and the purified protein was concentrated using an ultrafiltration kit for a molecular weight fraction of 10 kDa (Centricon (registered trademark), Millipore). The concentration of the purified protein was calculated from the absorbance at 280 nm using a molar absorption coefficient calculated according to the calculation formula of Pace et al. (Prof Sci. (1995) 4: 2411-2423).

1-2. Preparation of Anti-AXL-Antibody-Producing Hybridoma Deposited Under Accession No. FERM BP-10854

Four BALB/c mice (male, six weeks old at the start of immunization, Charles River Laboratories Japan) and two MRL/lpr mice (male, six weeks old at the start of immunization, Charles River Laboratories Japan) were immunized as described below with the antigen prepared in the previous section (hAXL-ECD-mIgG2aFc protein). Antigen emulsified with Freund's complete adjuvant (FCA) (H37 Ra, Difco Laboratories) was administered subcutaneously at 40 μg/head as the initial immunization. Two weeks later, antigen emulsified with Freund's incomplete adjuvant (FIA) (Difco Laboratories) was administered subcutaneously at 40 μg/head. The animals were subsequently immunized three times more at one week intervals. Increases in the serum antibody titer in response to the antigen were confirmed by ELISA (Enzyme linked immunosorbent assay) as indicated in the following section, followed by a final immunization of intravenous administration of antigen diluted with phosphate-buffered physiological saline (phosphate-buffered saline without calcium ions or magnesium ions, PBS(−); Nissui Pharmaceutical) at 10 μg/head. Three days after the final immunization, mouse spleen cells and mouse myeloma cells P3X63Ag8U.1 (referred to as P3U1, ATCC CRL-1597) were fused according to ordinary methods using PEG 1500 (Roche Diagnostics). The fused cells were cultured in RPMI1640 medium (Invitrogen) containing 10% FBS (Invitrogen) (hereafter referred to as 10% FBS/RPMI1640). On the day after fusion, the fused cells were suspended in semifluid medium (StemCells) followed by the selective culture and colonization of the hybridomas. Hybridoma colonies were picked from the medium on the ninth or tenth day after fusion and seeded into a 96-well plate containing HAT selective medium (10% FBS/RPMI1640, 2 vol % HAT 50× concentrate [Dainippon Pharmaceutical] and 5 vol % BM-Condimed H1 [Roche Diagnostics]) at one colony per well. After culture for three to four days, the supernatant was collected from each well and the hybridomas with binding activity to the extracellular domain of human AXL were selected by measuring their binding activity to the aforementioned antigen and to a control protein fused with the Fc domain of mouse IgG2a by ELISA, as indicated in the following section.

The binding activities of the supernatants of the selected hybridomas are shown in Table 3.

TABLE 3

| | AXL | | | | |
|---|---|---|---|---|---|
| Clone No. | 2ndSC Abs AXL-mFc | 2ndSC Abs FGFR2-mFc | 2ndSC Abs Abs Δ | 2ndSC Abs AXL-His | IgG Binding |
| 225 | 0.629 | 0.055 | 0.574 | 0.642 | 0.859 |

The hybridoma selected by the present inventors was deposited at the International Patent Organism Depositary of the National Institute of Advanced Industrial Science and Technology. The following section provides a description of the contents, specifying the deposition.

(a) Name and Address of the Depositary Institution

Name: International Patent Organism Depositary, National Institute of Advanced Industrial Science and Technology Address: Tsukuba Central 6, 1-1-1 Higashi, Tsukuba, Ibaraki, Japan 305-8566

(b) Acceptance Date (Deposition Date): Jul. 5, 2007

(c) Accession No.

AXL No. 225 #070402 (Ax225) (Accession No. FERM BP-10854)

1-3. Binding Activity to Human AXL

Antigen (hAXL-ECD-mIgG2aFc protein) diluted to 1 μg/mL with coating buffer (100 mM sodium bicarbonate [pH 9.6], 0.02% sodium azide) or control protein fused with the Fc domain of mouse IgG2a was dispensed into a 96-well plate (Nunc-Immuno™ 96 MicroWell™ MaxiSorp™ plate; Nalge Nunc International) at 80 μL/well, followed by incubation overnight or longer at 4° C. After it was washed three times with phosphate-buffered physiological saline containing 0.05 vol % Tween (registered trademark) 20 (tPBS(−)), the plate was blocked overnight or longer at 4° C. with diluent buffer (1/5 dilution of BlockingOne; Nacalai Tesque). Then the buffer was removed and mouse antiserum or hybridoma culture supernatant diluted with diluent buffer was added to the plate at 80 μL/well, followed by incubation for one hour at room temperature. The plate was then washed three times with tPBS(−), and HRP-labeled anti-mouse IgG antibody (Stressgen), diluted 1/5000 with diluent buffer, was added at 80 μL/well, followed by incubation for one hour at room temperature. After the plate had been washed five times with tPBS(−), a chromogenic substrate, Peroxidase Substrate (Kirkegaad & Perry Laboratories), was added at 80 μL/well, followed by incubation for 20 minutes at room temperature. Following the addition of Peroxidase Stop Solution (Kirkegaad & Perry Laboratories) at 80 μL/well, the absorbance at 405 nm was measured with a Microplate Reader Model 3550 (Bio-Rad Laboratories).

1-4. Purification of Antibody from Hybridoma Culture Supernatant

The resulting hybridomas described above were cultured in HAT selective medium using low-IgG FBS (Invitrogen) as the FBS. Protein G beads (Pharmacia), in which the solvent was replaced with wash buffer (20 mM sodium acetate buffer, pH 5.0), were added to 20-50 mL of the culture supernatant at 50 μL per 10 mL of culture supernatant, followed by mixing by inversion overnight at 4° C. After the Protein G beads had been recovered and washed with wash buffer, the antibody was eluted with elution buffer (50 mM sodium acetate buffer, pH 3.3), followed immediately by neutralization with neutralizing buffer (Tris-HCl buffer, pH 7.8). The buffer was replaced with phosphate-buffered physiological saline (pH 7.35-7.65; Nissui Pharmaceutical) and the purified antibody was concentrated using an ultrafiltration kit for a molecular weight fraction of 10 kDa (Amicon (registered trademark), Millipore), followed by sterilization with a 0.22 µm sterilization filter (Millipore GV, Millipore).

Referential Example 2

Binding Activity to Human AXL-FND1 and Human AXL-IgD2

2-1. Binding Activity to Human AXL-FND1 and Human AXL-IgD2

The binding abilities of anti-AXL monoclonal antibody to AXL-fibronectin type 3 domain 1 (AXL-FND1) and AXL immunoglobulin family domain 2 (AXL-IgD2) were tested.

2-2. Preparation of Human Recombinant AXL-FND1 and Human Recombinant AXL-IgD2 Expression Vectors Human recombinant AXL-FND1 was prepared by amplifying by PCR a region equivalent to the 225th to 331st amino acids from full-length human AXL cDNA (O'Bryan, et al., Mol. Cell. Biol. (1991) 11: 5016-5031) (GenBank No. NM_021913), cloning the amplified products to pET-41a(+) (Novagen) to express fusion proteins with GST-tag, and constructing pET-AXL-FND1. Other domains were prepared by amplifying by PCR a region AXL-IgD2 equivalent to the 137th to 224th amino acids, and cloning the amplified products to pET-41a(+) to express fusion proteins with GST-tag.

Each of the prepared vectors (5 µl) was transformed to DH5α (Toyobo Co., Ltd., Cat. No. DNA-903) by a heat shock method and then cultured in SOC medium. Colonies were selected after culturing overnight at 37° C. on an LB plate containing kanamycin.

2-3. Purification of Human Recombinant AXL-FND1 and Human Recombinant AXL-IgD2

Each of the produced colonies were precultured overnight at 37° C. in 20 mL of LB medium containing kanamycin and then transferred to 500 mL of medium. The each colony was cultured to an $A_{600}$ of 0.5±0.05 and IPTG was added to be a concentration of 0.5 mM. After culturing for one hour at 37° C., the bacterial cells were collected and suspended in Buffer A (50 mM Tris-HCl (pH 8.0), 1 mM EDTA, 0.5 mM PMSF, and 1 mM DTT). Freezing and thawing was repeated twice using liquid nitrogen. NP-40 was then added to 0.5% and the cells were homogenized with an ultrasonic homogenizer (30 seconds×5) and centrifuged for 30 minutes at 244,000×G, and then the supernatant was recovered.

Human recombinant AXL-FND1 was purified in the manner described below using the resulting supernatant. Solubilized E. coli supernatant was mixed with Glutathione Sepharose™ 4B Fast Flow (GE Healthcare) and stirred for one hour at 4° C. with a rotator. After centrifugation for five minutes at 500×G, the supernatant was discarded and the Glutathione Sepharose™ 4B was washed by adding Buffer A. This washing procedure was repeated three times. After transferring the human recombinant AXL-FND1 from the washed Glutathione Sepharose™ 4 Fast Flow to a mini-column, it was separated and eluted from the Glutathione Sepharose™ 4 Fast Flow with 50 mM Tris-HCl (pH 7.5) and 25 mM glutathione. Each of other AXL domains was expressed, separated, and eluted in the same manner.

2-4. Evaluation of Binding Activity of Anti-AXL Antibody to AXL-FND1 by Western Blotting The human recombinant AXL-FND1 separated and eluted from the Glutathione Sepharose™ 4 Fast Flow, as well as AXL-IgD1, AXL-IgD2, AXL-FND2, AXL-IgD1+IgD2, AXL-IgD2+FND1, and AXL-FND1+FND2 were quantified using the BIO-RAD Dc Protein Assay. 1 µg each was mixed with NuPAGE (registered trademark) Sample Buffer (Invitrogen), and electrophoresed with NuPAGE (registered trademark) 10% Bis-Tris Gel. The electrophoresed gel was transferred to an Immobilon™-FL (Millipore) PVDF membrane. The PVDF membrane containing the transferred protein was blocked with Odyssey (registered trademark) Blocking Buffer (LI-COR) and immersed in a primary antibody solution in which anti-AXL antibody was diluted to 5 µg/mL, and incubated overnight at 4° C. The PVDF membrane containing the transferred protein and immersed in the primary antibody solution was washed four times for five minutes each with 0.1% TBS-T (TBS (Tris-Buffered Saline (Takara)) containing 0.1% Tween-20). The PVDF membrane immersed in anti-AXL antibody was immersed in Alexa Fluor (registered trademark) 680 Goat Anti-mouse IgG (H+L) (Invitrogen) secondary antibody solution diluted to 80 ng/mL and incubated for one hour at room temperature. After washing the PVDF membrane immersed in the secondary antibody solution three times for five minutes each with 0.1% TBS-T, the membrane was washed for five minutes with TBS-T containing 0.01% SDS and then washed for five minutes with TBS. The binding of the washed PVDF membrane was then evaluated by scanning with the Odyssey (registered trademark) far infrared imaging system.

2-5. Results

The evaluation results are shown in FIG. 1.

Anti-AXL antibody produced by a hybridoma deposited under Accession No. FERM BP-10854 (Ax225) was demonstrated to recognize FND1 of AXL (FIG. 1). Anti-AXL antibody produced by a hybridoma deposited under Accession No. FERM BP-10857 (Ax284) was considered to recognize FND1 and IgD2 of AXL (FIG. 1). Anti-AXL antibody produced by a hybridoma deposited under Accession No. FERM BP-10850 (Ax7) and anti-AXL antibody produced by a hybridoma deposited under Accession No. FERM BP-10851 (Ax51) were demonstrated to recognize IgD2 of AXL (FIG. 1).

Referential Example 3

Assay of the Induction of AXL Protein Downmodulation by the Antibody Ax225

The ability of the anti-AXL monoclonal antibody to induce the downmodulation of AXL within cancer cells was tested. Human non-small-cell lung cancer cell line Calu-1 was seeded into six-well plates at a density of $4 \times 10^5$ cells/well and 24 hours later, the medium was replaced with medium from which the serum had been removed (serum-starved medium) and then the cells were cultured overnight. Next, the anti-AXL monoclonal antibody prepared as described above was added at 2 µg/mL, and recombinant GAS6 (R&D) was added at 200 ng/mL to act as the positive control, followed by incubation for 24 hours at 37° C. Next, the cells were washed with PBS(−) and the protein was extracted from the cells with the previously described cell lysis buffer. The cell lysis products, immunoprecipitated with a commercially available anti-AXL antibody (Santa Cruz™), were separated on 7% NuPAGE (Invitrogen), immunoblotted by western blotting, and tyrosine phosphorylation assay, as previously described.

25 µg of each protein solution was suspended in NuPAGE-LDS sample buffer (Invitrogen), heated for 10 minutes at 70° C., and electrophoresed for one hour at 150 V on 7% NuPAGE (Invitrogen). The gels separated by electrophoresis were electrophoretically transferred to a 0.45 µm polyvinylidene difluoride filter (Immobilon-FL, Millipore) over the course of one hour at 30 mA in NuPAGE transfer buffer (Invitrogen) and the buffer containing 20 vol % methanol. The filter was washed with TBS (50 mM Tris-HCl [pH 7.6], 150 mM NaCl) and then blocked by incubation overnight in Odyssey blocking buffer (Li—COR). The filter was washed four times for five minutes each with TBST and then incubated for two hours at room temperature with anti-AXL antibody (diluted 1:15,000 with TBST; Santa Cruz) and anti-actin antibody (diluted 1:5,000 with TBST). After the filter had been washed four times for five minutes each with TBST, it was incubated for one hour with Alexa 680-labeled anti-rabbit secondary antibody (Invitrogen) diluted 1:10,000 with TBST and IRDye 800-labeled anti-goat secondary antibody (Rockland) diluted 1:10,000 with TBST. After it had been washed three times for five minutes each with TBST, the filter was washed again once for five minutes with TBS, and then scanned with the Odyssey infrared imaging system (Li—COR).

The AXL blots were observed to weaken following exposure to the Ax225 antibody (FIG. 2). Therefore, the Ax225 antibody can induce the downmodulation of AXL protein.

Referential Example 4

Measurement of Antitumor Effects of the Anti-AXL Antibody in a Mouse Xenograft Model with Human Pancreatic Adenocarcinoma 1. Preparation of a Mouse Xenograft Model with Human Pancreatic Adenocarcinoma The human pancreatic adenocarcinoma cell line PANC-1, purchased from Dainippon Pharmaceutical (currently Dainippon Sumitomo Pharma), was prepared at $5 \times 10^7$ cells/mL with HBSS. 200 µL of the cell suspension ($1 \times 10^7$ cells/mouse) was subcutaneously grafted into the inguinal region of a CAnN.Cg-Foxn1<nu>/CrlCrlj nu/nu (BALB-nu/nu) mouse purchased from Charles River Laboratories, Japan. The mouse was subjected to the experiment when the mean tumor volume had reached about 210 mm³

2. Antibody Preparation and Administration

The Ax225 antibody was prepared at 2 mg/mL with PBS and administered twice a week for two weeks at 20 mg/kg into the peritoneal cavity of the mouse xenografted with human pancreatic adenocarcinoma. As the negative control, PBS was administered in the same manner. Gemzar (Eli Lilly Japan) was prepared at 12 mg/mL with physiological saline as the positive control and administered intraperitoneally at 120 mg/kg twice a week for two weeks.

3. Evaluation of Antitumor Effects

Figure 3:
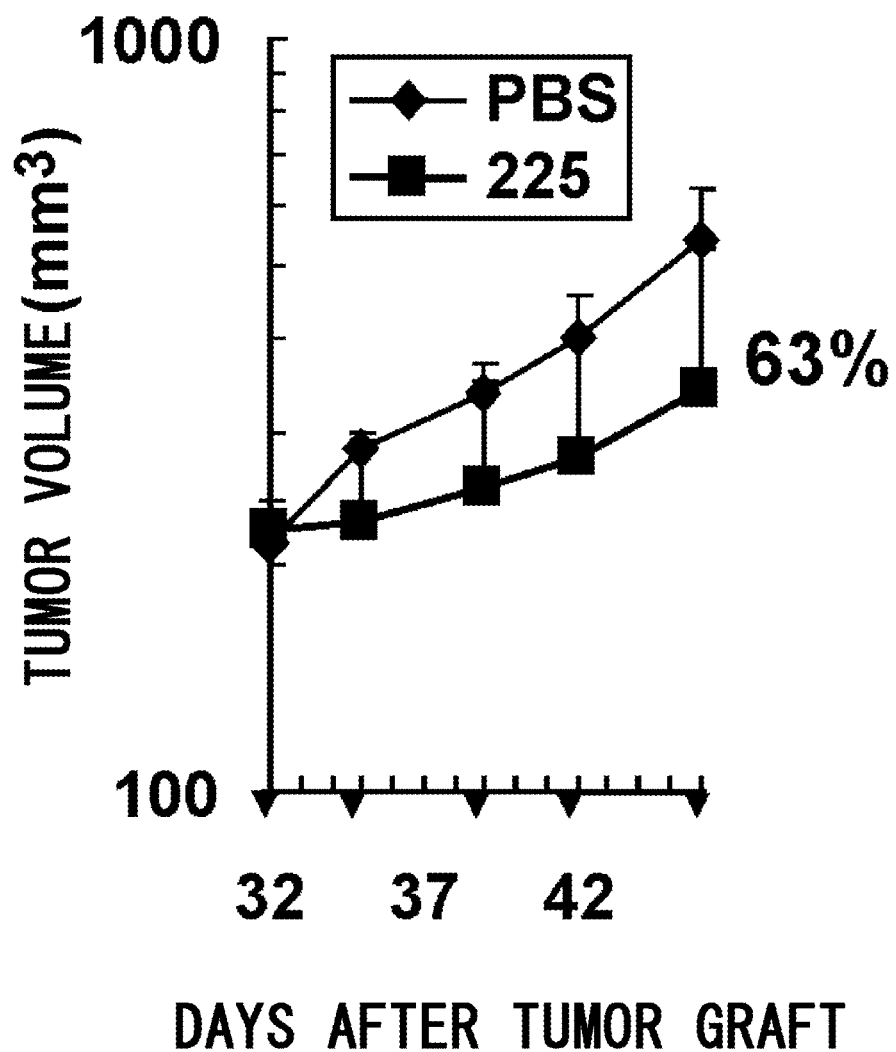
FIG. 3 depicts a graph showing the antitumor effect of anti-AXL antibody on human pancreatic adenocarcinoma-xenografted mouse model.

The antitumor effects in a mouse xenograft model with human pancreatic adenocarcinoma were calculated as tumor-growth-suppressive effects by comparing the tumor growth in the antibody-treated group with the tumor growth in the negative control group four days after the final administration (FIG. 3).

Tumor-growth-suppressive effect (%)=(1−amount of tumor growth in the antibody-treated group/ amount of tumor growth in the control group)× 100

4. Statistical Processing

Tumor volume was expressed as the mean±standard deviation. Statistical analysis consisted of a comparison between the control group and the treated group by the LSD method using the SAS Preclinical Package Ver. 5.0. Reliability of 95% (*: p<0.05) was determined to constitute significance.

5. Results

The Ax225 antibody inhibited tumor growth and demonstrated antitumor effects (FIG. 3).

Referential Example 5

Measurement of Antitumor Effects of Anti-AXL Antibody on Mouse Xenograft Model with Human Pancreatic Adenocarcinoma (2)

1. Preparation of Mouse Xenograft Model with Human Pancreatic Adenocarcinoma

Human pancreatic adenocarcinoma cell line PANC-1 purchased from Dainippon Pharmaceutical (currently Dainippon Sumitomo Pharma) was prepared to $5 \times 10^7$ cells/mL with HBSS. 200 µL of the cell suspension ($1 \times 10^7$ cells/mouse) were subcutaneously grafted to the inguinal regions of CAnN.Cg-Foxn1<nu>/CrlCrlj nu/nu (BALB-nu/nu) mice purchased from Charles River Laboratories, Japan. The mice were used in the experiment when the mean tumor volume reached about 270 mm³

2. Antibody Preparation and Administration

The Ax225 antibody and anti-AXL antibodies obtained similarly as Ax225 antibody but have a different epitope were prepared to 2 mg/mL with PBS and administered into the peritoneal cavity of the mice xenografted with human pancreatic adenocarcinoma twice a week for two weeks at 20 mg/kg. PBS was administered in the same manner for use as a negative control. Gemzar (Eli Lilly Japan) was prepared to 12 mg/mL with physiological saline for use as a positive control and administered intraperitoneally twice a week for two weeks at 120 mg/kg.

3. Evaluation of Antitumor Effects

Antitumor effects in a mouse xenograft model with human pancreatic adenocarcinoma were calculated as tumor-growth-suppressive effects by comparing with the amount of tumor growth of a negative control group four days after final administration.

Tumor growth suppressive effect (%)=(1−amount of tumor growth of the antibody-treated group/ amount of tumor growth of the control group)× 100

4. Results

The results for suppression of tumor growth are shown in FIG. 1. A tumor-growth-suppressive effect (%) of lower than 30% is indicated as "−", that of 30% or more is indicated as "+", and that of 60% or more is indicated as "++".

Antibodies that bind to FND-1 demonstrated 60% or more of TGI activity even if administration was begun at the time when mean tumor volumes had reached about 270 mm³. This finding that anti-AXL antibodies that bind to FND-1 have such significant antitumor effects in vivo was determined for the first time in this study and was completely unexpected.

Example 1

Production of Chimeric Antibodies

Production of Chimeric Antibody Expression Vectors

To produce chimeric Ax225 antibodies, in which the human IgG1 constant region and Ax225 antibody variable region are fused, two synthetic oligo-DNAs, a sense strand and an antisense strand, were designed for each of the H and L chains such that the 5' end of the cDNA encoding the human IgG1 constant region (H chain: human γ1; L chain: human κ) and the 3' end of the cDNA encoding Ax225 antibody variable region were fused. Hereinafter, they will be referred to as H-chain sense fusion primer (A), H chain antisense fusion primer (B), L chain sense fusion primer (C), and L chain antisense fusion primer (D). Each of the synthetic oligo-DNAs was admixed, and a gene encoding the chimeric Ax225 antibody was produced by assembly PCR. The first step of expressing the chimeric antibody by assembly PCR involved performing PCR according to the following conditions using four combinations: a sense strand produced by adding a Kozak sequence and a restriction enzyme site to the H chain 5' end of Ax225 cDNA (E) and the above-mentioned (B); an antisense strand produced by adding a restriction enzyme site to the H chain 3' end region of Ax225 cDNA (F) and the above-mentioned (A); a sense strand produced by adding a restriction enzyme site and a Kozak sequence to the L chain 5' end region of Ax225 cDNA (G) and the above-mentioned (D); and an antisense strand produced by adding a restriction enzyme site to the L chain 3' end region of Ax225 cDNA (H) and the above-mentioned (C). A reaction mixture comprising the attached PCR Buffer, dNTPs, PrimeSTAR, a cDNA encoding the Ax225 H chain or L chain, and one synthetic oligo-DNA was heated at 98° C. for one minute, and then subjected to PCR reaction consisting of 30 cycles of 98° C. for 10 seconds, 55° C. for 10 seconds, and 72° C. for one minute. The second PCR was performed using the gene fragments amplified in the first PCR reaction as the template. For the H chain, mixture of the fragments amplified using the (E) (B) and (F) (A) combinations were used, and for the L chain, mixture of the fragments amplified using the (G) (D) and (H) (C) combinations were used. As primers, (E) and (F) were used for the H chain and (G) and (H) were used for the L chain. After heating at 98° C. for one minute, PCR reaction consisting of 30 cycles of 98° C. for 10 seconds, 55° C. for 10 seconds, and 72° C. for one minute thirty seconds was carried out.

The obtained amplified fragments were cloned into an animal cell expression vector. The nucleotide sequence of each DNA fragment was determined using BigDye Terminator Cycle Sequencing Kit (Applied Biosystems) on an ABI PRISM 3730xL DNA Sequencer or an ABI PRISM 3700 DNA Sequencer (Applied Biosystems) according to the method described in the attached manual.

Expression and Purification of Chimeric Antibodies

Human embryonic renal cancer cell-derived FreeStyle™ 293-F cells (Invitrogen) were suspended in FreeStyle™ 293 Expression Medium (Invitrogen), and were seeded at 30 mL per 125-mL flask (CORNING) at a cell density of 1×10⁶ cells/mL. Opti-MEM I Reduced Serum Medium (Invitrogen) was added to the prepared plasmid DNA mixture solution (a total of 30 μg) to make the volume 1 mL. Furthermore, Opti-MEM I Reduced Serum Medium (Invitrogen) was added to 60 μL of 293 fectin (Invitrogen) to make the volume 1 mL, and this was mixed with the plasmid DNA mixture solution. The mixture solution was incubated at room temperature for 20 minutes, and was added to the cell suspension. This was incubated for three to six days in a $CO_2$ incubator (37° C., 8% $CO_2$). After the culture supernatant was collected, the cells were removed by centrifugation (approximately 2,000 g for five minutes at room temperature), and this was also passed through a 0.22 μm MILLEX®-GV filter (Millipore). Each sample was stored at 4° C. until use. Antibodies were purified from this supernatant using Protein A Sepharose (GE Healthcare). The absorbance at 280 nm was measured on an ND-1000 Spectrophotometer (NanoDrop), and the concentration was calculated by the method of Pace et al. (Protein Science (1995) 4: 2411-2423).

Example 2

Humanization of Ax225 Antibody

Affinity Measurements Using Biacore

To screen for humanized Ax225 antibodies, assessment of binding activity to AXL-FND1 was carried out by the following method using Biacore.

2-1. Preparation of Expression Vectors for Human Recombinant AXL-FND1

To prepare human recombinant AXL-FND1, the region corresponding to the amino acid positions 225 to 331 in the full-length human AXL cDNA (O'Bryan et al., Mol. Cell. Biol. 1991; 11: 5016-5031) (GenBank # NM_021913) was amplified by PCR, and this was cloned into pET-41b(+) (Novagen) for expression of the fusion protein with GST-tag, and pET-AXL-FND1 was constructed.

Each of the produced vectors (5 μL) was transfected into BL21-CodonPlus (DE3) RIPL (Stratagene, Cat #230280) by the heat shock method, cells were cultured in an SOC medium and then cultured overnight on a kanamycin-containing LB plate at 37° C., and then colonies were selected.

2-2. Purification of Human Recombinant AXL-FND1

Each of the produced colonies was pre-cultured in 3 mL of kanamycin-containing MagicMedia (Invitrogen) for three hours at 37° C., transferred to 500 mL of medium, and cultured overnight at 25° C. Bacterial cells were then collected and suspended in Buffer A (20 mM Tris-HCl (pH 8), 10 mM EDTA, 30 mM NaCl, Protease inhibitor mixture (complete Mini, EDTA-free (Roche))), and then lysozyme solution was added at a final concentration of 2 mg/mL. This was incubated on ice for one hour, then upon addition of Triton-X100 at a final concentration of 0.5% and NaCl at a final concentration of 100 mM, this was incubated on ice for ten minutes. After the cells were disrupted (30 seconds×5) using an ultrasonic homogenizer, they were centrifuged at 244,000×G for 20 minutes, and the supernatant was collected.

Using the obtained supernatant, human recombinant AXL-FND1 was purified as follows. Glutathione Sepharose™ 4B Fast Flow (GE Healthcare) was washed with PBS, then mixed with a solubilized E. coli supernatant, and left for binding overnight at 4° C. Glutathione Sepharose™ 4B Fast Flow was collected and washing operation with 30 mL of washing buffer (20 mM Tris-HCl (pH 8), 500 mM NaCl, 1% Triton-X100, protease inhibitor mixture) was repeated four times. Glutathione Sepharose™ 4B Fast Flow was transferred to a column, and further washing operation was carried out using 5 mL of the washing buffer. Separation and elution from Glutathione Sepharose™ 4B Fast Flow to obtain the human recombinant AXL-FND1 involved three repetitions of an elution operation using 5 mL of elution buffer (100 mM Tris-HCl (pH 8), 20 mM glutathione, 120 mM NaCl).

2-3. Affinity Analysis with Biacore Using Protein A

Kinetic analyses of antigen-antibody reactions of humanized AXL antibodies were carried out using Biacore T100 (BIACORE). rec-Protein A (Zymed) (hereinafter, Protein A) was immobilized onto a sensor chip, various antibodies were bound to it, then an antigen as the analyte was flushed to measure the antibody-antigen interaction. Human recombinant AXL-FND1 (prepared in 2-2; hereinafter referred to as GST-FND1) prepared at various concentrations was used as the antigen. From the sensorgrams obtained through the measurements, kinetic parameters, namely binding rate constant $k_a$ (1/Ms) and dissociation rate constant $k_d$ (1/s), were calculated, and $K_d$ (M) was calculated based on these values. Biacore T100 Evaluation Software (BIACORE) was used to calculate each of the parameters.

The sensor chips were produced by immobilizing approximately 3000 RU of Protein A onto CM5 (BIACORE) by amine coupling. Using the produced sensor chip, kinetic analyses were carried out on the interaction between the Protein A-bound antibodies and GST-FND1. HBS-EP+ was used as the running buffer, and the flow rate was set to 30 µL/min. Each antibody was prepared at 1 µg/mL using the running buffer, and was subjected to binding with Protein A for two minutes. GST-FND1 as the analyte was prepared at 0.5 and 2.0 µg/mL using HBS-EP+. Measurements were carried out by first binding the various humanized AXL antibodies, chimeric AXL antibodies, or mouse AXL antibodies of interest to Protein A, then applying an analyte solution to them for a two-minute interaction, and then switching to HBS-EP+ (BIACORE) for a two-minute measurement of the dissociation phase. After completion of measurement of the dissociation phase, 30 µL of 10 mM glycine-HCl (pH 2.0) was used for washing to regenerate the sensor chip. Such binding, dissociation, and regeneration were defined as one cycle of analysis. All experiments were performed at 25° C.

Selection of Each Framework Sequence

To humanize the Ax225 antibody, the variable region sequences of the Ax225 antibody and the human germline sequences were compared. Of these, FR sequences which will serve as a template for humanization are summarized in Table 4. As for the humanized variable region H chain, the sequence comprising FR1, FR2, FR3(2), and FR4 described in Table 4 was defined as H0 (SEQ ID NO: 2). As for the L chain, the sequence comprising FR1, FR2, FR3, and FR4 was defined as L0 (SEQ ID NO: 65). CDRs and FRs were determined according to Kabat numbering.

In the sequence of H chain FR3, the residue at position 94 by Kabat numbering has been reported to have great influence on the three-dimensional structure of CDR3 (Morea et al., J. Mol. Biol. 1998, 275: 269-294). This residue is glycine (G) in Ax225 (SEQ ID NO: 57), but as indicated for FR3(1) (SEQ ID NO: 109) in Table 4, the corresponding residue in the germline sequence selected for humanization was arginine (R). Therefore, substitution of arginine would take place as a result of humanization, and decrease in activity was expected. Accordingly, the residue of Ax225 at position 94 in the H chain was kept and the sequence of FR3(2) in which this residue is glycine (SEQ ID NO: 58) was used.

TABLE 4

| | Germline | SEQUENCE |
|---|---|---|
| H0 | | |
| FR1 | Germline: hVH_2_26 | QVTLKESGPVLVKPTETLTLTCTVSGFSLS (SEQ ID NO: 51) |
| FR2 | Germline: hVH_1_24 | WVRQAPGKGLEWMG (SEQ ID NO: 53) |
| FR3(1) | Germline: hVH_2_26 | RLTISKDTSKSQVVLTMTNMDPVDTATYYCAR (SEQ ID NO: 109) |
| FR3(2) | Germline: hVH_2_26 (G is substituted at position 94) | RLTISKDTSKSQVVLTMTNMDPVDTATYYCAG (SEQ ID NO: 58) |
| FR4 | Germline: hJH1 | WGQGTLVTVSS (SEQ ID NO: 61) |
| L0 | | |
| FR1 | Germline: hVK_2_30 | DVVMTQSPLSLPVTLGQPASISC (SEQ ID NO: 93) |
| FR2 | Germline: hVK_1D_8 | WYQQKPGKAPELLIY (SEQ ID NO: 96) |
| FR3 | Germline: hVK_2_40 | GVPDRFSGSGSGTDFTLKISRVEAEDVGVYYC (SEQ ID NO: 101) |
| FR4 | Germline: hJK2 | FGQGTKLEIK (SEQ ID NO: 103) |

Production of Humanized Ax225 Variable Regions H0 and L0

Synthetic oligo-DNAs were designed for the H chain and L chain to produce variable regions of humanized Ax225 antibody in which the CDR regions of Ax225 antibody are grafted into the FR regions of the humanized template sequences. Each of the synthetic oligo-DNAs was admixed, and a gene encoding the variable regions of humanized Ax225 was produced by assembly PCR. The H chain was named H0 and the L chain was named L0. Assembly PCR was carried out using KOD-Plus (TOYOBO), and by PCR method according to the following conditions. Amplified fragments were obtained by subjecting a reaction mixture comprising the attached PCR Buffer, dNTPs, MgSO$_4$, KOD-Plus, and 10 pmol of synthetic oligo-DNA to heating at 94° C. for five minutes, and then performing two PCR reaction cycles consisting of 94° C. for two minutes, 55° C. for two minutes, and 68° C. for two minutes, and then adding a primer including a restriction enzyme site and a Kozak sequence added to the 5' end of the variable region and a primer including a restriction enzyme site added to the 3' end of the variable region at 10 pmols each, and then performing 35 cycles of PCR reaction consisting of 94° C. for 30 seconds, 55° C. for 30 seconds, and 68° C. for one minute. The obtained amplified fragments were cloned using an animal cell expression vector, and fused to the constant region.

Here, amidation of the C-terminal amino group due to deletion of the C-terminal amino acid lysine residue and deletion of two C-terminal amino acids glycine and lysine is reported as heterogeneity derived from the H-chain C-terminal sequence of IgG antibody (Anal. Biochem. 2007 Jan. 1; 360 (1): 75-83). A known method for decreasing such heterogeneity is to delete two H-chain C-terminal amino acids, namely to delete glycine at position 446 and lysine at position 447 by EU numbering (Patent Document 4: WO 2009/041613). Since absence of heterogeneity derived from the H-chain C-terminal sequence is desirable for the humanized Ax225 antibody as well, the IgG1 sequence in which the glycine at position 446 and lysine at position 447 by EU numbering in human IgG1 are deleted (SEQ ID NO: 106) was used as the constant region sequence. On the other hand, for the L chain, natural-type human κ chain (SEQ ID NO: 107) was used as the constant region sequence.

Discovery of Amino Acid Residues Essential to Maintenance of Activity

As described earlier, glycine in the Ax225 H chain at position 94 by Kabat numbering was predicted to play an important role in the binding with AXL.

Therefore, to evaluate the effect of this residue on activity, a modified form (H6; SEQ ID NO: 108) was produced, wherein the residue of the chimeric antibody H chain (chH; SEQ ID NO: 1) at position 94 by Kabat numbering was substituted with the residue for human germline sequence which is arginine. The mutant was produced by performing assembly PCR which utilizes PCR. Specifically, sense-strand and antisense-strand oligo-DNAs that were designed based on the amino acid sequence containing the modified site were synthesized. The sense strand oligo-DNA containing the modified site and the antisense oligo-DNA which binds to the vector into which the gene to be modified is inserted, and the antisense strand oligo-DNA containing the modified site and the sense strand oligo-DNA that binds to the vector into which the gene to be modified is inserted were combined respectively, and by performing PCR using PrimeSTAR (TAKARA), two fragments, 5'-end and 3'-end fragments containing the modified site were produced. Each mutant was produced by linking the two fragments by assembly PCR. The produced mutants were inserted into an expression vector that enables expression of the inserted gene in animal cells, and the nucleotide sequence of the obtained expression vector was determined by a method known to those skilled in the art.

Expression and purification of chH/L0 (H-chain chH/SEQ ID NO: 1; L chain L0/SEQ ID NO: 65) and H6/L0 (H chain H6/SEQ ID NO: 108; L chain L0/SEQ ID NO: 65) were carried out according to the method of Example 1. The sequences for chH and H6 are completely the same except for position 94 by Kabat numbering, so the effect of this residue alone can be evaluated.

The results of affinity evaluation of chH/L0 and H6/L0 by Biacore are shown in Table 5. A significant decrease in affinity was confirmed for H6/L0 in comparison to chH/L0. This showed that for binding of the Ax225 antibody and humanized Ax225 antibody to AXL-FND1, glycine is preferred as the residue at position 94 by Kabat numbering in the H chain, and arginine is inappropriate.

TABLE 5

| H | L | KD(M) |
|---|---|---|
| chH | L0 | 1.59E−09 |
| H6 | L0 | 1.23E−08 |

Production of H9, an H-Chain Variable Region with Improved Affinity

The amino acid residue at position 73 by Kabat numbering of H0 (SEQ ID NO: 2), which is the H chain of H0/L0, is threonine (T), but upon consideration based on a three-dimensional structural model, substitution of this residue with asparagine (N) as in the sequence of the Ax225 antibody was expected to increase in affinity.

Therefore, the threonine (T) at position 73 by Kabat numbering in FR3 of H0 (SEQ ID NO: 2) was replaced with asparagine (N) to produce H9 (SEQ ID NO: 3). The mutant was produced by performing assembly PCR which utilizes PCR. Specifically, first, sense-strand and antisense-strand oligo-DNAs that were designed based on the amino acid sequence containing the modified site were synthesized. The sense strand oligo-DNA containing the modified site and the antisense oligo-DNA which binds to the vector into which the gene to be modified is inserted, and the antisense strand oligo-DNA containing the modified site and the sense strand oligo-DNA that binds to the vector into which the gene to be modified is inserted were combined respectively, and by performing PCR using PrimeSTAR (TAKARA), two fragments, 5'-end and 3'-end fragments containing the modified site were produced. Each mutant was produced by linking the two fragments by assembly PCR. The produced mutants were inserted into an expression vector that enables expression of the inserted gene in animal cells, and the nucleotide sequence of the obtained expression vector was determined by a method known to those skilled in the art. Antibodies were produced and purified according to the method of Example 1.

Affinity measurement of H9/L0 was carried out by the method of Example 2, and the result is shown in Table 6. Increase in affinity was confirmed for H9/L0 in comparison to H0/L0.

TABLE 6

| | KD(M) |
|---|---|
| H0/L0 | 4.44E−09 |
| H9/L0 | 3.58E−09 |

Example 3

Identification of Mutation Sites which Will Change the Isoelectric Point

Identification of Mutation Sites

As a method for regulating the plasma half-life of an antibody, a method of controlling the surface charge of an antibody molecule by modifying amino acid residues exposed to the surface of an antibody molecule is known (Patent Documents 2 and 3). Specifically, it is known that decreasing the isoelectric point (pI) value of an antibody enables prolongation of the plasma half-life of the antibody. Conversely, it is known that increasing the isoelectric point of an antibody shortens its plasma half-life, and improves its tissue distribution properties (Non-patent Documents 28 and 29).

From the above, a humanized Ax225 antibody with a modified isoelectric point is expected to have a stronger antitumor activity due to prolonged plasma half-life or improved tissue distribution properties. Therefore, amino acid residues that allow regulation of pharmacokinetics of the humanized Ax225 antibody by adjusting the surface charge on the antibody molecule without having effects on the antibody's binding activity against antigens and three-dimensional structure were identified. Specifically, mutation sites that can change the isoelectric point without greatly reducing affinity as measured by Biacore were searched for in the variable region of H9/L0 (H chain H9/SEQ ID NO: 3; L chain L0/SEQ ID NO: 65).

As a result of using a three-dimensional structural model of the humanized Ax225 antibody to screen for mutation sites that can change the isoelectric point of the variable region without greatly decreasing the binding to AXL, several mutation sites were found. Modifications in the H chain and L chain that decrease the isoelectric point are shown in Table 7 and Table 8 (modification sites in the H chain for decreasing the isoelectric point), and Table 9 (modification sites in the L chain for decreasing the isoelectric point); and modifications in the H chain and L chain that increase the isoelectric point are shown in Table 10 and Table 11 (modification sites in the H chain for increasing the isoelectric point), and Table 12 (modification sites in the L chain for increasing the isoelectric point). Each of the variants were produced and purified by the method of Example 1.

Affinity evaluation of each of the variants by Biacore was carried out by the method of Example 2. As shown in Tables 13 to 15, the affinity of each of the variants did not show a large decrease compared to that of H9/L0. The SEQ ID NOs of the H chain and L chain of each of the variants are also shown in Tables 13 to 15.

TABLE 7

| NAME | CLASSIFICATION | H9 SEQUENCE | MUTATED POSITION (kabat No.) | AMINO ACID BEFORE MUTATION (H9) | AMINO ACID AFTER MUTATION | SEQUENCE AFTER MUTATION |
|---|---|---|---|---|---|---|
| H17 | CDR1 | SFGVD (SEQ ID NO: 33) | 31 | S | D | DFGVD (SEQ ID NO: 34) |
| H18 | CDR1 | SFGVD (SEQ ID NO: 33) | 31 | S | E | EFGVD (SEQ ID NO: 35) |
| H19 | FR2 | WVRQAPGKGLEWMG (SEQ ID NO: 53) | 43 | K | Q | WVRQAPGQGLEWMG (SEQ ID NO: 54) |
| H20 | FR2 | WVRQAPGKGLEWMG (SEQ ID NO: 53) | 40<br>43<br>48 | A<br>K<br>M | P<br>E<br>I | WVRQPPGEGLEWIG (SEQ ID NO: 55) |
| H21 | CDR2 | VIWGGGSTNYNSALKS (SEQ ID NO: 38) | 61 | S | E | VIWGGGSTNYNEALKS (SEQ ID NO: 39) |
| H22 | CDR2 | VIWGGGSTNYNSALKS (SEQ ID NO: 38) | 62 | A | E | VIWGGGSTNYNSELKS (SEQ ID NO: 40) |
| H23 | CDR2 | VIWGGGSTNYNSALKS (SEQ ID NO: 38) | 64 | K | Q | VIWGGGSTNYNSALQS (SEQ ID NO: 41) |
| H24 | CDR2 | VIWGGGSTNYNSALKS (SEQ ID NO: 38) | 65 | S | D | VIWGGGSTNYNSALKD (SEQ ID NO: 42) |
| H25 | CDR2 | VIWGGGSTNYNSALKS (SEQ ID NO: 38) | 64<br>65 | K<br>S | Q<br>D | VIWGGGSTNYNSALQD (SEQ ID NO: 43) |
| H26 | CDR2 | VIWGGGSTNYNSALKS (SEQ ID NO: 38) | 61<br>64<br>65 | S<br>K<br>S | E<br>Q<br>D | VIWGGGSTNYNEALQD (SEQ ID NO: 44) |

TABLE 8

| NAME | CLASSIFICATION | H9 SEQUENCE | MUTATED POSITION (kabat No.) | AMINO ACID BEFORE MUTATION (H9) | AMINO ACID AFTER MUTATION | SEQUENCE AFTER MUTATION |
|---|---|---|---|---|---|---|
| H27 | CDR2 | VIWGGGSTNYNSALKS (SEQ ID NO: 38) | 62<br>64<br>65 | A<br>K<br>S | E<br>Q<br>D | VIWGGGSTNYNSELQD (SEQ ID NO: 45) |
| H28 | CDR2 | VIWGGGSTNYNSALKS (SEQ ID NO: 38) | 61<br>62<br>64<br>65 | S<br>A<br>K<br>S | E<br>E<br>Q<br>D | VIWGGGSTNYNEELQD (SEQ ID NO: 46) |
| H30 | FR4 | WGQGTLVTVSS (SEQ ID NO: 61) | 105 | Q | E | WGEGTLVTVSS (SEQ ID NO: 62) |
| H31 | FR2 | WVRQAPGKGLEWMG (SEQ ID NO: 53) | 43 | K | Q | WVRQAPGQGLEWMG (SEQ ID NO: 54) |
|  | CDR2 | VIWGGGSTNYNSALKS (SEQ ID NO: 38) | 61<br>64<br>65 | S<br>K<br>S | E<br>Q<br>D | VIWGGGSTNYNEALQD (SEQ ID NO: 44) |

TABLE 8-continued

| NAME | CLASSIFICATION | H9 SEQUENCE | MUTATED POSITION (kabat No.) | AMINO ACID BEFORE MUTATION (H9) | AMINO ACID AFTER MUTATION | SEQUENCE AFTER MUTATION |
|---|---|---|---|---|---|---|
| H32 | CDR2 | VIWGGGSTNYNSALKS (SEQ ID NO: 38) | 61 64 65 | S K S | E Q D | VIWGGGSTNYNEALQD (SEQ ID NO: 44) |
|  | FR4 | WGQGTLVTVSS (SEQ ID NO: 61) | 105 | Q | E | WGEGTLVTVSS (SEQ ID NO: 62) |
| H33 | FR2 | WVRQAPGKGLEWMG (SEQ ID NO: 53) | 43 | K | Q | WVRQAPGQGLEWMG (SEQ ID NO: 54) |
|  | CDR2 | VIWGGGSTNYNSALKS (SEQ ID NO: 38) | 61 64 65 | S K S | E Q D | VIWGGGSTNYNEALQD (SEQ ID NO: 44) |
|  | FR4 | WGQGTLVTVSS (SEQ ID NO: 61) | 105 | Q | E | WGEGTLVTVSS (SEQ ID NO: 62) |

Table 8 is a continuation of Table 7.

TABLE 9

| NAME | CLASSIFICATION | L0 SEQUENCE | MUTATED POSITION (kabat No.) | AMINO ACID BEFORE MUTATION (L0) | AMINO ACID AFTER MUTATION | SEQUENCE AFTER MUTATION |
|---|---|---|---|---|---|---|
| L1 | CDR1 | RSSQNIVHTNGNTYLE (SEQ ID NO: 84) | 24 | R | Q | QSSQNIVHTNGNTYLE (SEQ ID NO: 85) |
| L3 | CDR1 | RSSQNIVHTNGNTYLE (SEQ ID NO: 84) | 24 27 | R Q | Q E | QSSENIVHTNGNTYLE (SEQ ID NO: 86) |
| L4 | FR2 | WYQQKPGKAPELLIY (SEQ ID NO: 96) | 42 | K | E | WYQQKPGEAPELLIY (SEQ ID NO: 97) |
| L5 | FR2 | WYQQKPGKAPELLIY (SEQ ID NO: 96) | 42 | K | Q | WYQQKPGQAPELLIY (SEQ ID NO: 98) |
| L10 | FR4 | FGQGTKLEIK (SEQ ID NO: 103) | 104 107 | L K | V E | FGQGTKVEIE (SEQ ID NO: 104) |
| L11 | CDR1 | RSSQNIVHTNGNTYLE (SEQ ID NO: 84) | 24 | R | Q | QSSQNIVHTNGNTYLE (SEQ ID NO: 85) |
|  | FR4 | FGQGTKLEIK (SEQ ID NO: 103) | 104 107 | L K | V E | FGQGTKVEIE (SEQ ID NO: 104) |
| L12 | CDR1 | RSSQNIVHTNGNTYLE (SEQ ID NO: 84) | 24 | R | Q | QSSQNIVHTNGNTYLE (SEQ ID NO: 85) |
|  | FR2 | WYQQKPGKAPELLIY (SEQ ID NO: 96) | 42 | K | E | WYQQKPGEAPELLIY (SEQ ID NO: 97) |
|  | FR4 | FGQGTKLEIK (SEQ ID NO: 103) | 104 107 | L K | V E | FGQGTKVEIE (SEQ ID NO: 104) |
| L13 | CDR1 | RSSQNIVHTNGNTYLE (SEQ ID NO: 84) | 24 | R | Q | QSSQNIVHTNGNTYLE (SEQ ID NO: 85) |
|  | FR2 | WYQQKPGKAPELLIY (SEQ ID NO: 96) | 42 | K | Q | WYQQKPGQAPELLIY (SEQ ID NO: 98) |
|  | FR4 | FGQGTKLEIK (SEQ ID NO: 103) | 104 107 | L K | V E | FGQGTKVEIE (SEQ ID NO: 104) |

TABLE 10

| NAME | CLASSIFICATION | H9 SEQUENCE | MUTATED POSITION (kabat No.) | AMINO ACID BEFORE MUTATION (H9) | AMINO ACID AFTER MUTATION | SEQUENCE AFTER MUTATION |
|---|---|---|---|---|---|---|
| H34 | CDR1 | SFGVD (SEQ ID NO: 33) | 31 | S | K | KFGVD (SEQ ID NO: 36) |
| H35 | CDR1 | SFGVD (SEQ ID NO: 33) | 31 | S | R | RFGVD (SEQ ID NO: 37) |
| H36 | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
| H37 | CDR2 | VIWGGGSTNYNSALKS | 61 | S | R | VIWGGGSTNYNRALKS (SEQ ID NO: 47) |
| H38 | CDR2 | VIWGGGSTNYNSALKS (SEQ ID NO: 38) | 61 | S | K | VIWGGGSTNYNKALKS (SEQ ID NO: 48) |
| H39 | FR4 | WGQGTLVTVSS (SEQ ID NO: 61) | 105 | Q | R | WGRGTLVTVSS (SEQ ID NO: 63) |
| H40 | CDR1 | SFGVD (SEQ ID NO: 33) | 31 | S | K | KFGVD (SEQ ID NO: 36) |
|  | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
| H41 | CDR1 | SFGVD (SEQ ID NO: 33) | 31 | S | R | RFGVD (SEQ ID NO: 37) |
|  | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
| H46 | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
|  | CDR2 | VIWGGGSTNYNSALKS (SEQ ID NO: 38) | 61 | S | K | VIWGGGSTNYNKALKS (SEQ ID NO: 48) |

TABLE 11

| NAME | CLASSIFICATION | H9 SEQUENCE | MUTATED POSITION (kabat No.) | AMINO ACID BEFORE MUTATION (H9) | AMINO ACID AFTER MUTATION | SEQUENCE AFTER MUTATION |
|---|---|---|---|---|---|---|
| H47 | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
|  | CDR2 | VIWGGGSTNYNSALKS (SEQ ID NO: 38) | 61 | S | R | VIWGGGSTNYNRALKS (SEQ ID NO: 47) |
| H48 | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
|  | FR4 | WGQGTLVTVSS (SEQ ID NO: 61) | 105 | Q | R | WGRGTLVTVSS (SEQ ID NO: 63) |
| H49 | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |
|  | CDR2 | VIWGGGSTNYNSALKS (SEQ ID NO: 38) | 61 | S | K | VIWGGGSTNYNKALKS (SEQ ID NO: 48) |
|  | FR4 | WGQGTLVTVSS (SEQ ID NO: 61) | 105 | Q | R | WGRGTLVTVSS (SEQ ID NO: 63) |
| H50 | FR2 | WVRQAPGKGLEWMG (SEQ ID NO: 53) | 41<br>43<br>44 | P<br>K<br>G | R<br>Q<br>R | WVRQARGQRLEWMG (SEQ ID NO: 56) |

TABLE 11-continued

| NAME | CLASSIFICATION | H9 SEQUENCE | MUTATED POSITION (kabat No.) | AMINO ACID BEFORE MUTATION (H9) | AMINO ACID AFTER MUTATION | SEQUENCE AFTER MUTATION |
|---|---|---|---|---|---|---|
| | CDR2 | VIWGGGSTNYNSALKS (SEQ ID NO: 38) | 61 | S | R | VIWGGGSTNYNRALKS (SEQ ID NO: 47) |
| | FR4 | WGQGTLVTVSS (SEQ ID NO: 61) | 105 | Q | R | WGRGTLVTVSS (SEQ ID NO: 63) |

Table 11 is a continuation of Table 10.

TABLE 12

| NAME | CLASSIFICATION | L0 SEQUENCE | MUTATED POSITION (kabat No.) | AMINO ACID BEFORE MUTATION (L0) | AMINO ACID AFTER MUTATION | SEQUENCE AFTER MUTATION |
|---|---|---|---|---|---|---|
| L25 | FR1 | DVVMTQSPLSLPVTLGQPASISC (SEQ ID NO: 93) | 17 | Q | R | DVVMTQSPLSLPVTLGRPASISC (SEQ ID NO: 94) |
| L27 | CDR1 | RSSQNIVHTNGNTYLE (SEQ ID NO: 84) | 27 | Q | R | RSSRNIVHTNGNTYLE (SEQ ID NO: 87) |
| L28 | FR2 | WYQQKPGKAPELLIY (SEQ ID NO: 96) | 45 | E | K | WYQQKPGKAPKLLIY (SEQ ID NO: 99) |
| L29 | FR4 | FGQGTKLEIK (SEQ ID NO: 103) | 100 | Q | R | FGRGTKLEIK (SEQ ID NO: 105) |
| L31 | CDR1 | RSSQNIVHTNGNTYLE (SEQ ID NO: 84) | 27 | Q | R | RSSRNIVHTNGNTYLE (SEQ ID NO: 87) |
| | FR2 | WYQQKPGKAPELLIY (SEQ ID NO: 96) | 45 | E | K | WYQQKPGKAPKLLIY (SEQ ID NO: 99) |
| L34 | FR1 | DVVMTQSPLSLPVTLGQPASISC (SEQ ID NO: 93) | 17 | Q | R | DVVMTQSPLSLPVTLGRPASISC (SEQ ID NO: 94) |
| | CDR1 | RSSQNIVHTNGNTYLE (SEQ ID NO: 84) | 27 | Q | R | RSSRNIVHTNGNTYLE (SEQ ID NO: 87) |
| | FR2 | WYQQKPGKAPELLIY (SEQ ID NO: 96) | 45 | E | K | WYQQKPGKAPKLLIY (SEQ ID NO: 99) |
| L35 | CDR1 | RSSQNIVHTNGNTYLE (SEQ ID NO: 84) | 27 | Q | R | RSSRNIVHTNGNTYLE (SEQ ID NO: 87) |
| | FR2 | WYQQKPGKAPELLIY (SEQ ID NO: 96) | 45 | E | K | WYQQKPGKAPKLLIY (SEQ ID NO: 99) |
| | FR4 | FGQGTKLEIK (SEQ ID NO: 103) | 100 | Q | R | FGRGTKLEIK (SEQ ID NO: 105) |
| L37 | FR1 | DVVMTQSPLSLPVTLGQPASISC (SEQ ID NO: 93) | 17 | Q | R | DVVMTQSPLSLPVTLGRPASISC (SEQ ID NO: 94) |
| | CDR1 | RSSQNIVHTNGNTYLE (SEQ ID NO: 84) | 27 | Q | R | RSSRNIVHTNGNTYLE (SEQ ID NO: 87) |
| | FR2 | WYQQKPGKAPELLIY (SEQ ID NO: 96) | 45 | E | K | WYQQKPGKAPKLLIY (SEQ ID NO: 99) |
| | FR4 | FGQGTKLEIK (SEQ ID NO: 103) | 100 | Q | R | FGRGTKLEIK (SEQ ID NO: 105) |

TABLE 13

| HEAVY CHAIN | LIGHT CHAIN | SEQ ID NO OF HEAVY CHAIN | SEQ ID NO OF LIGHT CHAIN | KD(M) |
|---|---|---|---|---|
| H9 | L0 | 3 | 65 | 3.58E−09 |
| H9 | L1 | 3 | 66 | 2.49E−09 |
| H9 | L3 | 3 | 67 | 2.97E−09 |
| H9 | L4 | 3 | 68 | 2.64E−09 |

TABLE 13-continued

| HEAVY CHAIN | LIGHT CHAIN | SEQ ID NO OF HEAVY CHAIN | SEQ ID NO OF LIGHT CHAIN | KD(M) |
|---|---|---|---|---|
| H9 | L5 | 3 | 69 | 2.53E−09 |
| H9 | L10 | 3 | 70 | 2.92E−09 |
| H9 | L11 | 3 | 71 | 2.40E−09 |
| H9 | L12 | 3 | 72 | 2.55E−09 |
| H9 | L13 | 3 | 73 | 2.45E−09 |
| H17 | L0 | 4 | 65 | 3.46E−09 |
| H18 | L0 | 5 | 65 | 4.31E−09 |
| H19 | L0 | 6 | 65 | 2.63E−09 |
| H20 | L0 | 7 | 65 | 3.21E−09 |
| H21 | L0 | 8 | 65 | 2.35E−09 |
| H22 | L0 | 9 | 65 | 3.14E−09 |
| H23 | L0 | 10 | 65 | 2.39E−09 |
| H24 | L0 | 11 | 65 | 2.56E−09 |
| H25 | L0 | 12 | 65 | 2.50E−09 |
| H26 | L0 | 13 | 65 | 2.50E−09 |
| H26 | L10 | 13 | 70 | 2.38E−09 |
| H26 | L11 | 13 | 71 | 2.71E−09 |
| H26 | L12 | 13 | 72 | 2.79E−09 |
| H26 | L13 | 13 | 73 | 2.50E−09 |
| H27 | L0 | 14 | 65 | 3.03E−09 |
| H28 | L0 | 15 | 65 | 2.94E−09 |
| H30 | L0 | 16 | 65 | 2.70E−09 |
| H31 | L0 | 17 | 65 | 2.54E−09 |
| H31 | L10 | 17 | 70 | 3.03E−09 |
| H31 | L11 | 17 | 71 | 3.05E−09 |
| H31 | L12 | 17 | 72 | 3.14E−09 |
| H32 | L0 | 18 | 65 | 2.82E−09 |
| H32 | L10 | 18 | 70 | 2.80E−09 |
| H32 | L11 | 18 | 71 | 2.74E−09 |
| H32 | L12 | 18 | 72 | 2.64E−09 |
| H32 | L13 | 18 | 73 | 2.74E−09 |
| H33 | L0 | 19 | 65 | 3.04E−09 |
| H33 | L11 | 19 | 71 | 3.06E−09 |
| H33 | L12 | 19 | 72 | 3.06E−09 |
| H33 | L13 | 19 | 73 | 3.02E−09 |

TABLE 14

| HEAVY CHAIN | LIGHT CHAIN | SEQ ID NO OF HEAVY CHAIN | SEQ ID NO OF LIGHT CHAIN | KD(M) |
|---|---|---|---|---|
| H9 | L25 | 3 | 74 | 3.54E−09 |
| H9 | L27 | 3 | 75 | 3.07E−09 |
| H9 | L28 | 3 | 76 | 3.06E−09 |
| H9 | L29 | 3 | 77 | 3.49E−09 |
| H9 | L31 | 3 | 78 | 2.46E−09 |
| H9 | L34 | 3 | 79 | 2.80E−09 |
| H9 | L35 | 3 | 80 | 2.37E−09 |
| H9 | L37 | 3 | 82 | 2.69E−09 |
| H34 | L0 | 20 | 65 | 5.94E−09 |
| H35 | L0 | 21 | 65 | 3.65E−09 |
| H36 | L0 | 22 | 65 | 1.96E−09 |
| H36 | L1 | 22 | 66 | 2.03E−09 |
| H36 | L10 | 22 | 70 | 1.87E−09 |
| H36 | L11 | 22 | 71 | 2.08E−09 |
| H36 | L27 | 22 | 75 | 1.94E−09 |
| H36 | L28 | 22 | 76 | 1.95E−09 |
| H36 | L31 | 22 | 78 | 1.67E−09 |
| H36 | L34 | 22 | 79 | 2.01E−09 |
| H36 | L35 | 22 | 80 | 1.94E−09 |
| H36 | L37 | 22 | 82 | 2.20E−09 |
| H37 | L0 | 23 | 65 | 2.92E−09 |
| H38 | L0 | 24 | 65 | 2.92E−09 |
| H39 | L0 | 25 | 65 | 3.43E−09 |
| H40 | L0 | 26 | 65 | 3.51E−09 |
| H41 | L0 | 27 | 65 | 2.35E−09 |
| H46 | L0 | 28 | 65 | 1.87E−09 |
| H46 | L1 | 28 | 66 | 1.84E−09 |
| H46 | L10 | 28 | 70 | 1.88E−09 |
| H46 | L11 | 28 | 71 | 1.80E−09 |
| H46 | L27 | 28 | 75 | 1.90E−09 |
| H46 | L28 | 28 | 76 | 1.86E−09 |
| H46 | L31 | 28 | 78 | 1.90E−09 |
| H46 | L34 | 28 | 79 | 2.22E−09 |

TABLE 14-continued

| HEAVY CHAIN | LIGHT CHAIN | SEQ ID NO OF HEAVY CHAIN | SEQ ID NO OF LIGHT CHAIN | KD(M) |
|---|---|---|---|---|
| H46 | L35 | 28 | 80 | 2.04E−09 |
| H46 | L37 | 28 | 82 | 2.30E−09 |

TABLE 15

| HEAVY CHAIN | LIGHT CHAIN | SEQ ID NO OF HEAVY CHAIN | SEQ ID NO OF LIGHT CHAIN | KD(M) |
|---|---|---|---|---|
| H47 | L0 | 29 | 65 | 1.84E−09 |
| H47 | L1 | 29 | 66 | 1.89E−09 |
| H47 | L10 | 29 | 70 | 1.89E−09 |
| H47 | L11 | 29 | 71 | 1.83E−09 |
| H47 | L27 | 29 | 75 | 1.60E−09 |
| H47 | L28 | 29 | 76 | 1.52E−09 |
| H47 | L31 | 29 | 78 | 1.83E−09 |
| H47 | L34 | 29 | 79 | 2.20E−09 |
| H47 | L35 | 29 | 80 | 1.68E−09 |
| H47 | L37 | 29 | 82 | 2.38E−09 |
| H48 | L0 | 30 | 65 | 2.09E−09 |
| H48 | L1 | 30 | 66 | 2.09E−09 |
| H48 | L10 | 30 | 70 | 2.06E−09 |
| H48 | L11 | 30 | 71 | 2.00E−09 |
| H48 | L27 | 30 | 75 | 1.99E−09 |
| H48 | L28 | 30 | 76 | 2.07E−09 |
| H48 | L31 | 30 | 78 | 1.98E−09 |
| H48 | L34 | 30 | 79 | 2.27E−09 |
| H48 | L35 | 30 | 80 | 2.07E−09 |
| H48 | L37 | 30 | 82 | 2.19E−09 |
| H49 | L0 | 31 | 65 | 2.06E−09 |
| H49 | L1 | 31 | 66 | 1.91E−09 |
| H49 | L10 | 31 | 70 | 2.05E−09 |
| H49 | L11 | 31 | 71 | 1.92E−09 |
| H49 | L27 | 31 | 75 | 2.08E−09 |
| H49 | L28 | 31 | 76 | 2.11E−09 |
| H49 | L31 | 31 | 78 | 1.94E−09 |
| H49 | L34 | 31 | 79 | 2.21E−09 |
| H49 | L35 | 31 | 80 | 2.08E−09 |
| H49 | L37 | 31 | 82 | 2.43E−09 |
| H50 | L0 | 32 | 65 | 1.89E−09 |
| H59 | L1 | 32 | 66 | 1.86E−09 |
| H50 | L10 | 32 | 70 | 1.90E−09 |
| H50 | L11 | 32 | 71 | 1.82E−09 |
| H50 | L27 | 32 | 75 | 1.95E−09 |
| H50 | L28 | 32 | 76 | 1.97E−09 |
| H50 | L31 | 32 | 78 | 1.93E−09 |
| H50 | L34 | 32 | 79 | 2.36E−09 |
| H50 | L35 | 32 | 80 | 2.24E−09 |
| H50 | L37 | 32 | 82 | 2.72E−09 |

Example 4

Introduction of Mutations that Suppress Deamidation Reactions

Antibodies used for pharmaceuticals have heterogeneity even though they are monoclonal antibodies obtained from a clone derived from a single antibody-producing cell. Such antibody heterogeneity occurs due to modifications such as oxidation and deamidation, and is known to increase during long term storage or when subjected to stress conditions such as heat stress or light stress (Reference Document: Heterogeneity of Monoclonal Antibodies: Journal of Pharmaceutical Sciences, vol. 97, No. 7, 2426-2447). However, when developing an antibody as a pharmaceutical, the physicochemical properties of that protein, particularly homogeneity and stability, are extremely important, and reducing the heterogeneity of the substance of interest and, if possible, being a single substance is desired.

Deamidation reaction takes place non-enzymatically in the asparagine (N) and glutamine (Q) side chains, and is a reaction in which the amides present in the asparagine and glutamine side chains are changed to carboxylic acids. Deamidation reaction which takes place during storage causes the above-mentioned heterogeneity; therefore, it is desirably suppressed as much as possible. Furthermore, it is reported that the deamidation reaction readily occurs particularly at a site where asparagine (N) and glycine (G) are next to each other ( ... NG ... ) (Geiger et al., J. Biol. Chem. 1987; 262: 785-794). Since a sequence in which asparagine (N) and glycine (G) are next to each other exists in CDR1 of L0 (SEQ ID NO: 65), amino acid substitution at this site was considered to enable suppression of the deamidation reaction.

Specifically, suppression of deamidation reaction by amino acid substitution was carried out as follows. Substitution of alanine (A) for glycine (G) at position 29 by Kabat numbering in L0 (SEQ ID NO: 65) was considered to enable suppression of the deamidation reaction. Therefore, L36 (SEQ ID NO: 81) in which glycine (G) is replaced with alanine (A) at position 29 by Kabat numbering in L0 (SEQ ID NO: 65) was produced. Similarly, substitution of alanine (A) for glycine (G) at position 29 by Kabat numbering in L11 (SEQ ID NO: 71) was considered to enable suppression of the deamidation reaction. Therefore, L21 (SEQ ID NO: 83) in which glycine (G) is replaced with alanine (A) at position 29 by Kabat numbering in L11 (SEQ ID NO: 71) was produced. These were used to produce H9/L36 (H chain: H9/SEQ ID NO: 3; L chain: L36/SEQ ID NO: 81), H36/L36 (H chain: H36/SEQ ID NO: 22; L chain: L36/SEQ ID NO: 81), and H32/L21 (H chain: H32/SEQ ID NO: 18; L chain: L21/SEQ ID NO: 83). These variants were produced and purified by the method of Example 1.

Affinity measurements on the produced variants were carried out by the method of Example 2. The results are shown in Table 16. All variants had affinity that was not remarkably decreased compared to that of H9/L0, and suppression of the deamidation reaction was considered to be possible.

TABLE 16

| H | L | KD(M) |
|---|---|---|
| H9 | L0 | 3.58E−09 |
| H9 | L36 | 3.60E−09 |
| H36 | L36 | 2.59E−09 |
| H32 | L21 | 3.81E−09 |

Example 5

Discovery of Mutation Sites for Increasing the Antibody Expression Level

As a method for producing antibody pharmaceuticals, a method that uses mammalian cells to construct a stable transfectant that produces the antibody of interest is generally used. Herein, since the level of antibody expression by the stable transfectant is an important factor linked to production cost of antibody pharmaceuticals, it is desirable that the antibody expression level is sufficiently high.

To evaluate the effects of Ax225 antibody humanization on the antibody expression level, four types of antibodies, chimeric chH/chL antibody (H chain chH/SEQ ID NO: 1; L chain chL/SEQ ID NO: 64); H0/chL wherein the H chain alone is humanized (H chain H0/SEQ ID NO: 2; L chain chL/SEQ ID NO: 64); chH/L0 wherein the L chain alone is humanized (H chain chH/SEQ ID NO: 1; L chain L0/SEQ ID NO: 65); and H0/L0 wherein both chains are humanized (H chain H0/SEQ ID NO: 2; L chain L0/SEQ ID NO: 65), were expressed according to the method of Example 1.

Quantification of Antibody Concentration in the Culture Supernatant by Biacore-Q Quantification of antibody concentration in the culture supernatant using Biacore-Q (BIACORE) was carried out by the following method.

The sensor chips were produced by immobilizing approximately 5,000 RU of recombinant Protein A onto CM5 (GE Healthcare) by amine coupling. HBS-EP was used as the running buffer, 10 mM glycine-HCl (pH 1.5) was used as the regeneration buffer, and the flow rate was set to 5 μL/min. Furthermore, to produce a calibration curve, the chimeric antibody or the humanized antibody expressed and purified by the method of Example 1 were prepared at concentrations of 2,000, 1,000, 500, 250, 125, and 62.5 ng/mL.

The collected culture supernatant was suitably diluted using HBS-EP to produce antibody concentrations that correctly lie on the calibration curve. The prepared culture supernatant and the samples for calibration curve production were subjected to Biacore-Q, and by measuring and analyzing using BIACORE Q Control Software on COM1, antibody concentration in the culture supernatant was calculated.

Figure 4:
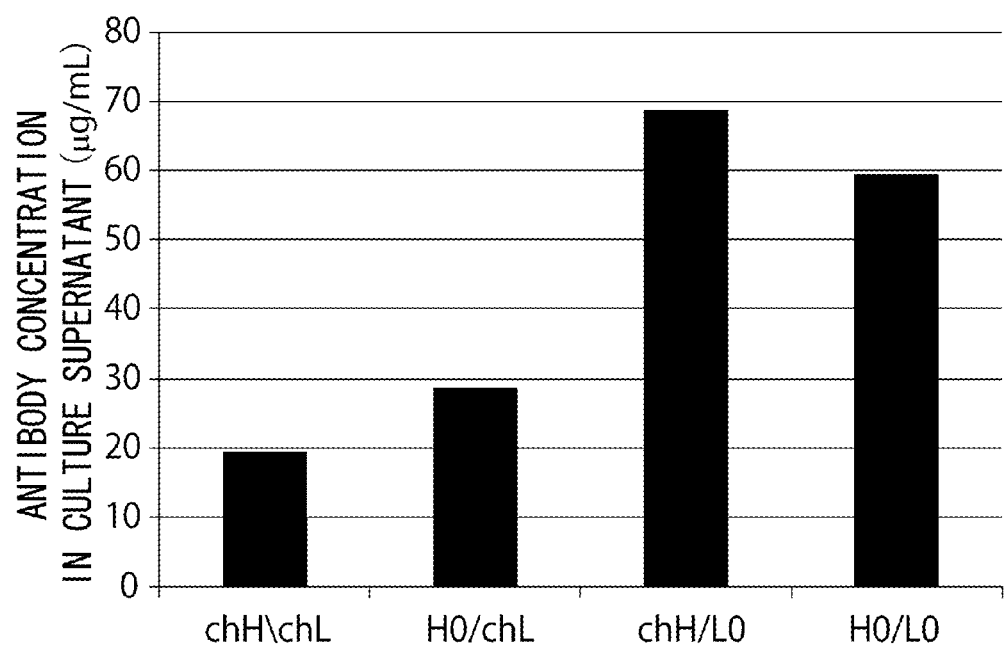
FIG. 4 depicts a graph showing the expression levels of humanized Ax225 antibodies.

As a result, it was found that humanizing the L chain increased the level of Ax225 antibody expression by two- to three-folds (FIG. 4).

Identification of Mutation Sites that Increase the Antibody Expression Level

From the three-dimensional structural model, the residue at position 42 by Kabat numbering in the L chain FR2 was expected to contribute greatly to the expression level. Specifically, substituting lysine (K) for the residue at position 42 by Kabat numbering was expected to enable enhancement of the expression level. This speculation does not contradict the fact that the residue at position 42 by Kabat numbering in the chimeric antibody L chain (chL/SEQ ID NO: 64) is glutamine (Q), whereas this residue in the humanized antibody L chain (L0/SEQ ID NO: 65) is lysine (K).

To evaluate the effect of the residue at position 42 by Kabat numbering in the L chain on the expression level, H32/L11 (H chain H32/SEQ ID NO: 18; L chain L11/SEQ ID NO: 71) and H32/L12 (H chain H32/SEQ ID NO: 18; L chain L12/SEQ ID NO: 72) were expressed by the method of Example 1, and the antibody concentration in the culture supernatant was measured. The difference between the two types of L chains, L11 and L12, used herein is that the residue at position 42 by Kabat numbering in the L11 is lysine (K) whereas that in L12 is replaced with glutamic acid (E). Since the sequences of the two are completely identical except for position 42 by Kabat numbering, the influence of this residue alone can be evaluated.

Figure 5:
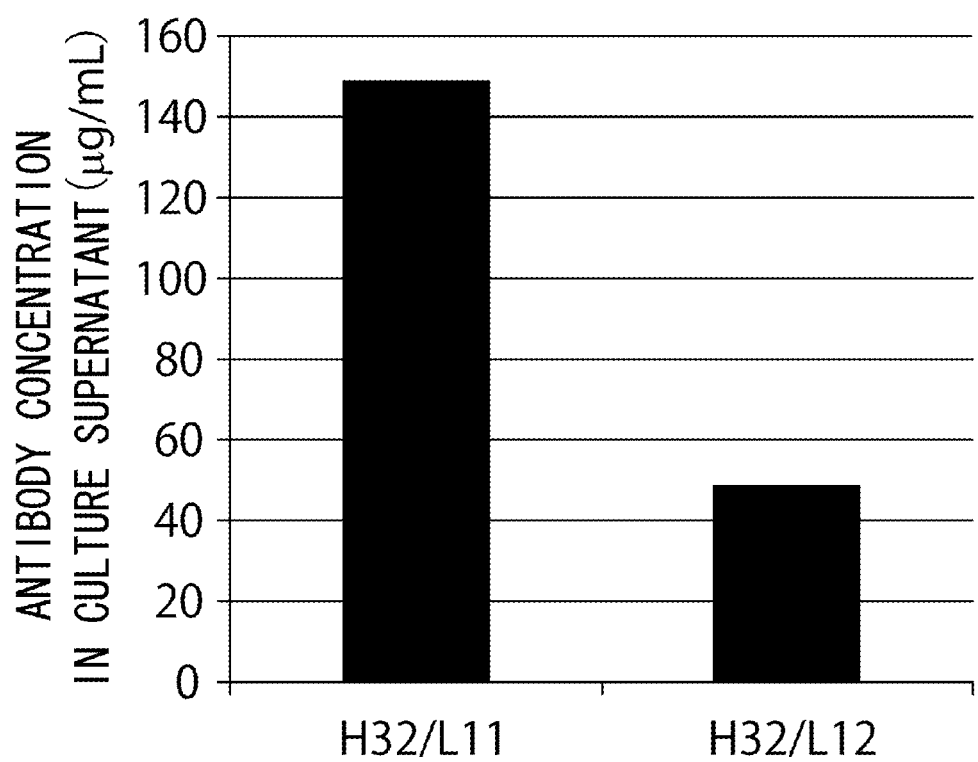
FIG. 5 depicts a graph showing the expression levels of humanized Ax225 antibodies.

The results are shown in FIG. 5. H32/L11 whose position 42 by Kabat numbering is lysine showed an approximately three-fold enhancement of the expression level as compared to H32/L12 in which this residue is glutamic acid. Therefore, substituting lysine for the residue at position 42 by Kabat numbering was shown to enable great enhancement of the expression level (FIG. 5).

Example 6

Measurement of Antitumor Effect of Humanized Ax225 Antibody on Mouse Xenograft Model with Human Pancreatic Adenocarcinoma 6-1. Production of Mouse Xenograft Model with Human Pancreatic Adenocarcinoma Human pancreatic adenocarcinoma cell line PANC-1 obtained from Dainippon Pharma Co., Ltd. (currently Dainippon Sumitomo Pharma Co., Ltd.) was prepared using HBSS to provide $2.5 \times 10^7$ cells/mL. Two-hundred microliters of the cell suspension solution ($5 \times 10^6$ cells/mouse) was inoculated subcutaneously to the inguinal region of CAnN.Cg-Foxn1<nu>/CrlCrlj nu/nu (BALB-nu/nu) mice purchased from Japan Charles River Co. Ltd. When the tumor volume reached approximately 240 mm³, the mice were subjected to the experiment.

6-2. Antibody Preparation and Administration

The antibody was prepared at 1 mg/mL in PBS, and was administered intraperitoneally to human pancreatic adenocarcinoma-xenografted mice at 10 mg/kg once a week for two weeks. As a negative control, PBS was administered similarly.

6-3. Evaluation of Antitumor Effects

The antitumor effect in the human pancreatic adenocarcinoma-xenografted mouse model was calculated as a tumor growth inhibiting effect by comparison with the amount of tumor growth in the negative control group seven days after the final administration.

[tumor growth inhibiting effect (%)]=(1−[amount of tumor growth in the antibody-treated group]/[amount of tumor growth in the control group])×100

6-4. Statistical Treatment

The tumor volume was expressed by the mean±standard deviation. Statistical analyses were carried out by comparing the control group and the treated group by the LSD method using SAS Preclinical Package Version 5.0. A 95% confidence level (*; p<0.05) was used to indicate significance.

6-5. Results

Figure 6:
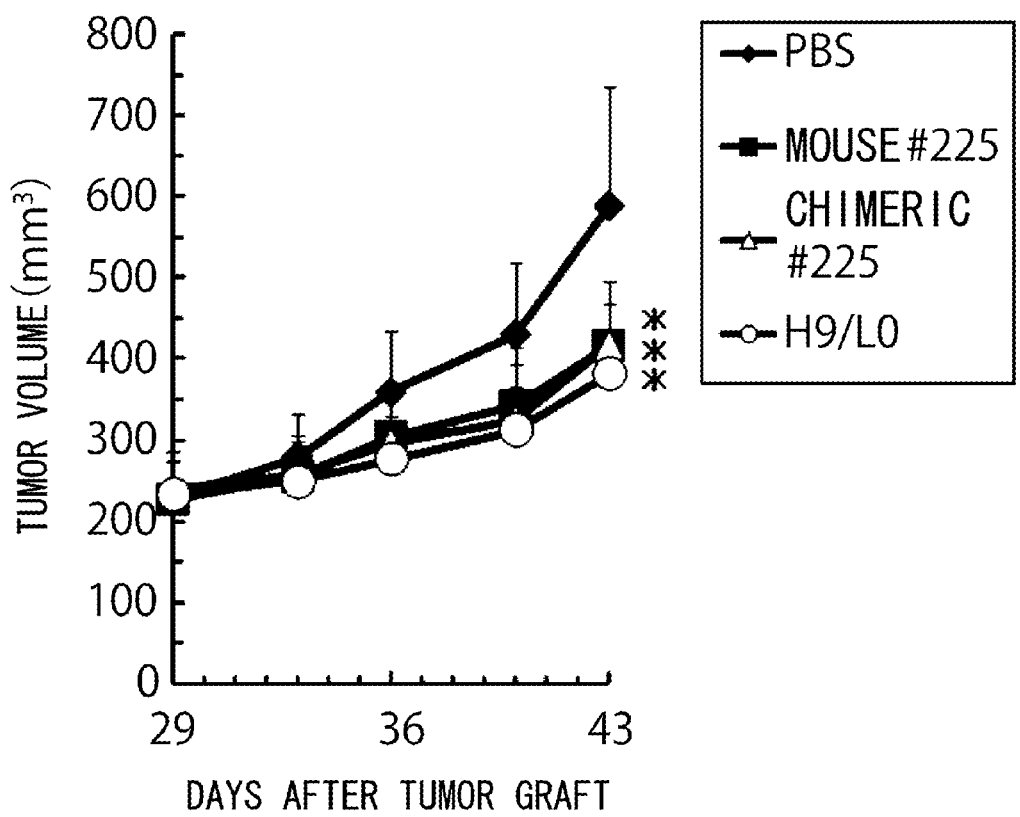
FIG. 6 depicts a graph showing the tumor growth inhibiting effects of the humanized Ax225 antibody (H9/L0). The asterisk (*) indicates that p<0.05.

As shown in FIG. 6, similarly to the mouse antibody and the chimeric antibody, the humanized Ax225 antibody (H9/L0) showed significant tumor growth inhibiting effects as compared to the PBS-administered group.

Example 7

Measurement of Antitumor Effects of Humanized Anti-AXL Antibodies on Mouse Xenograft Model with Human Pancreatic Adenocarcinoma (2)

7-1. Production of Mouse Xenograft Model with Human Pancreatic Adenocarcinoma

Human pancreatic adenocarcinoma cell line PANC-1 obtained from Dainippon Pharma Co., Ltd. (currently Dainippon Sumitomo Pharma Co., Ltd.) was prepared using HBSS to provide $2.5 \times 10^7$ cells/mL. Two-hundred microliters of the cell suspension solution ($5 \times 10^6$ cells/mouse) was inoculated subcutaneously to the inguinal region of CAnN.Cg-Foxnl<nu>/CrlCrlj nu/nu (BALB-nu/nu) mice purchased from Japan Charles River Co. Ltd. When the tumor volume reached approximately 200 mm³, the mice were subjected to the experiment.

7-2. Antibody Preparation and Administration

Each antibody was prepared at 1 mg/mL in histidine buffer solution (20 mM Histidine-HCl, 150 mM NaCl, pH 6.0), and was administered into caudal vein of human pancreatic adenocarcinoma-xenografted mice at 10 mg/kg once a week for two weeks. As a negative control, histidine buffer solution was administered similarly.

7-3. Evaluation of Antitumor Effects

The antitumor effects in the human pancreatic adenocarcinoma-xenografted mouse model were calculated as a tumor growth inhibiting effect by comparing the amount of tumor in each antibody-administered group and the amount of tumor in the negative control group seven days after the final administration.

7-4. Statistical Treatment

The tumor volume was expressed by the mean±standard deviation. Statistical analyses were carried out by comparing the control group and the treated group by the LSD method using SAS Preclinical Package Version 5.0. A 95% confidence level (*; p<0.05) was used to indicate significance.

7-5. Results

Figure 7:
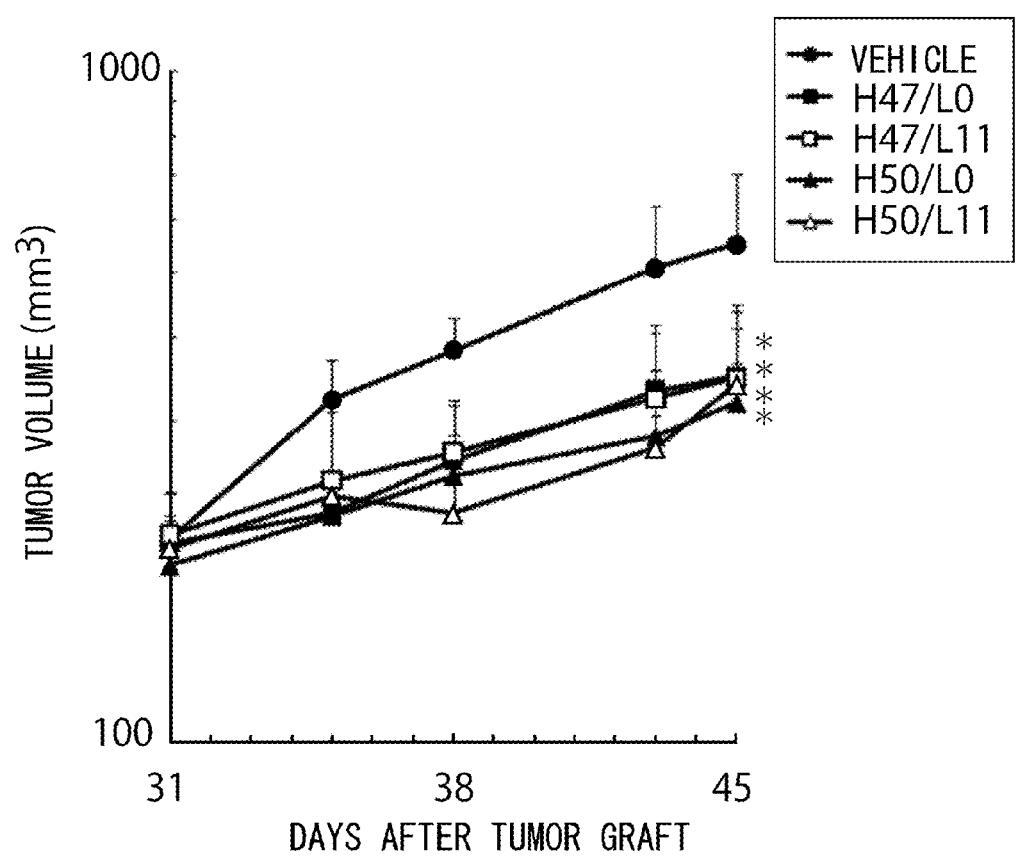
FIG. 7 depicts a graph showing the antitumor effects of humanized anti-AXL antibodies (H47/L0, H47/L11, H50/L0, and H50/L11) on human pancreatic adenocarcinoma-xenografted mouse model. The asterisk (*) indicates that p<0.05.

As shown in FIG. 7, the antibody-administered groups showed significant tumor growth inhibiting effects as compared to the histidine buffer solution-administered group.

INDUSTRIAL APPLICABILITY

The present inventors succeeded in obtaining humanized anti-AXL antibodies. The anti-AXL antibodies of the present invention have high antitumor activity, and are useful as antitumor agents and diagnostic agents for cancer.

---

The invention claimed is:

1. An antibody that recognizes fibronectin type III domain 1 (FND1) of anexelekto (AXL), which is an antibody of any one of (1) to (3) below:

(1) an antibody comprising a heavy chain variable region comprising a CDR1 comprising the amino acid sequence of any one of SEQ ID NOs: 33 to 37, a CDR2 comprising the amino acid sequence of any one of SEQ ID NOs: 38 to 48, and a CDR3 comprising the amino acid sequence of SEQ ID NO: 49; and a light chain variable region comprising a CDR1 comprising the amino acid sequence of any one of SEQ ID NOs: 84 to 89, a CDR2 comprising the amino acid sequence of SEQ ID NO: 90, and a CDR3 comprising the amino acid sequence of SEQ ID NO: 91; wherein the amino acid sequence of the heavy chain variable region comprises at least one of the following amino acid residues:

(a) the amino acid residue at position 31 by Kabat numbering in the heavy chain variable region is aspartic acid, glutamic acid, lysine, or arginine;

(b) the amino acid residue at position 40 by Kabat numbering in the heavy chain variable region is proline;

(c) the amino acid residue at position 41 by Kabat numbering in the heavy chain variable region is arginine;

(d) the amino acid residue at position 43 by Kabat numbering in the heavy chain variable region is glutamine or glutamic acid;

(e) the amino acid residue at position 44 by Kabat numbering in the heavy chain variable region is arginine;

(f) the amino acid residue at position 48 by Kabat numbering in the heavy chain variable region is isoleucine;

(g) the amino acid residue at position 61 by Kabat numbering in the heavy chain variable region is glutamic acid, lysine, or arginine;
(h) the amino acid residue at position 62 by Kabat numbering in the heavy chain variable region is glutamic acid;
(i) the amino acid residue at position 64 by Kabat numbering in the heavy chain variable region is glutamine;
(j) the amino acid residue at position 65 by Kabat numbering in the heavy chain variable region is aspartic acid; and
(k) the amino acid residue at position 105 by Kabat numbering in the heavy chain variable region is glutamic acid or arginine;
(2) an antibody comprising a heavy chain variable region of SEQ ID NO: 2 (H0); and
(3) an antibody comprising a light chain variable region of SEQ ID NO: 65 (L0).

2. A humanized antibody that recognizes FND1 domain of AXL, which is an antibody of any one of (1) to (5) below:
(1) an antibody comprising a heavy chain variable region comprising a CDR1 comprising the amino acid sequence of any one of SEQ ID NOs: 33 to 37, a CDR2 comprising the amino acid sequence of any one of SEQ ID NOs: 38 to 48, and a CDR3 comprising the amino acid sequence of SEQ ID NO: 49, as well as an FR1 comprising the amino acid sequence of SEQ ID NO: 51, an FR2 comprising the amino acid sequence of SEQ ID NO: 53, an FR3 comprising the amino acid sequence of SEQ ID NO: 109 or 58, and an FR4 comprising the amino acid sequence of SEQ ID NO: 61;
(2) an antibody comprising the heavy chain variable region of SEQ ID NO: 2 (H0);
(3) an antibody comprising a light chain variable region comprising a CDR1 comprising the amino acid sequence of any one of SEQ ID NOs: 84 to 89, a CDR2 comprising the amino acid sequence SEQ ID NO: 90, and a CDR3 comprising the amino acid sequence of SEQ ID NO: 91, as well as an FR1 comprising the amino acid sequence of SEQ ID NO: 93, an FR2 comprising the amino acid sequence of SEQ ID NO: 96, an FR3 comprising the amino acid sequence of SEQ ID NO: 101, and an FR4 comprising the amino acid sequence of SEQ ID NO: 103;
(4) an antibody comprising the light chain variable region of SEQ ID NO: 65; and
(5) an antibody comprising the heavy chain variable region of (1) and the light chain variable region of (3).

3. The antibody of claim 1, wherein the antibody comprises the heavy chain variable region of (1) with a glycine at position 94 by Kabat numbering.

4. The antibody of claim 1, wherein the antibody comprises the light chain variable region of (1), and the amino acid sequence of the light chain variable region of (1) comprises at least one of the following amino acid residues:
(1) the amino acid residue at position 17 by Kabat numbering in the light chain variable region is arginine;
(2) the amino acid residue at position 24 by Kabat numbering in the light chain variable region is glutamine;
(3) the amino acid residue at position 27 by Kabat numbering in the light chain variable region is glutamic acid or arginine;
(4) the amino acid residue at position 29 by Kabat numbering in the light chain variable region is alanine;
(5) the amino acid residue at position 42 by Kabat numbering in the light chain variable region is glutamic acid or glutamine;
(6) the amino acid residue at position 45 by Kabat numbering in the light chain variable region is lysine;
(7) the amino acid residue at position 100 by Kabat numbering in the light chain variable region is arginine;
(8) the amino acid residue at position 104 by Kabat numbering in the light chain variable region is valine; and
(9) the amino acid residue at position 107 by Kabat numbering in the light chain variable region is glutamic acid.

5. The antibody of claim 1, comprising at least any one of the following heavy chain variable regions:
(1) a heavy chain variable region comprising a CDR1 comprising the amino acid sequence of SEQ ID NO: 33, a CDR2 comprising the amino acid sequence of SEQ ID NO: 38, and a CDR3 comprising the amino acid sequence of SEQ ID NO: 49;
(2) a heavy chain variable region comprising a CDR1 comprising the amino acid sequence of SEQ ID NO: 34, a CDR2 comprising the amino acid sequence of SEQ ID NO: 38, and a CDR3 comprising the amino acid sequence of SEQ ID NO: 49;
(3) a heavy chain variable region comprising a CDR1 comprising the amino acid sequence of SEQ ID NO: 35, a CDR2 comprising the amino acid sequence of SEQ ID NO: 38, and a CDR3 comprising the amino acid sequence of SEQ ID NO: 49;
(4) a heavy chain variable region comprising a CDR1 comprising the amino acid sequence of SEQ ID NO: 33, a CDR2 comprising the amino acid sequence of SEQ ID NO: 39, and a CDR3 comprising the amino acid sequence of SEQ ID NO: 49;
(5) a heavy chain variable region comprising a CDR1 comprising the amino acid sequence of SEQ ID NO: 33, a CDR2 comprising the amino acid sequence of SEQ ID NO: 40, and a CDR3 comprising the amino acid sequence of SEQ ID NO: 49;
(6) a heavy chain variable region comprising a CDR1 comprising the amino acid sequence of SEQ ID NO: 33, a CDR2 comprising the amino acid sequence of SEQ ID NO: 41, and a CDR3 comprising the amino acid sequence of SEQ ID NO: 49;
(7) a heavy chain variable region comprising a CDR1 comprising the amino acid sequence of SEQ ID NO: 33, a CDR2 comprising the amino acid sequence of SEQ ID NO: 42, and a CDR3 comprising the amino acid sequence of SEQ ID NO: 49;
(8) a heavy chain variable region comprising a CDR1 comprising the amino acid sequence of SEQ ID NO: 33, a CDR2 comprising the amino acid sequence of SEQ ID NO: 43, and a CDR3 comprising the amino acid sequence of SEQ ID NO: 49;
(9) a heavy chain variable region comprising a CDR1 comprising the amino acid sequence of SEQ ID NO: 33, a CDR2 comprising the amino acid sequence of SEQ ID NO: 44, and a CDR3 comprising the amino acid sequence of SEQ ID NO: 49;
(10) a heavy chain variable region comprising a CDR1 comprising the amino acid sequence of SEQ ID NO: 33, a CDR2 comprising the amino acid sequence of SEQ ID NO: 45, and a CDR3 comprising the amino acid sequence of SEQ ID NO: 49;
(11) a heavy chain variable region comprising a CDR1 comprising the amino acid sequence of SEQ ID NO: 33, a CDR2 comprising the amino acid sequence of SEQ ID NO: 46, and a CDR3 comprising the amino acid sequence of SEQ ID NO: 49;
(12) a heavy chain variable region comprising a CDR1 comprising the amino acid sequence of SEQ ID NO: 36, a CDR2 comprising the amino acid sequence of SEQ ID NO: 38, and a CDR3 comprising the amino acid sequence of SEQ ID NO: 49;
(13) a heavy chain variable region comprising a CDR1 comprising the amino acid sequence of SEQ ID NO: 37, a CDR2 comprising the amino acid sequence of SEQ ID NO: 38, and a CDR3 comprising the amino acid sequence of SEQ ID NO: 49;
(14) a heavy chain variable region comprising a CDR1 comprising the amino acid sequence of SEQ ID NO: 33, a CDR2 comprising the amino acid sequence of SEQ ID NO: 47, and a CDR3 comprising the amino acid sequence of SEQ ID NO: 49; and
(15) a heavy chain variable region comprising a CDR1 comprising the amino acid sequence of SEQ ID NO: 33, a CDR2 comprising the amino acid sequence of SEQ ID NO: 48, and a CDR3 comprising the amino acid sequence of SEQ ID NO: 49.

6. The antibody of claim 1, which is selected from the group consisting of (1) to (25):
(1) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 84, 90, and 91, respectively;
(2) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 85, 90, and 91, respectively;
(3) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 86, 90, and 91, respectively;
(4) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 87, 90, and 91, respectively;
(5) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 88, 90, and 91, respectively;
(6) an antibody comprising a heavy chain variable region comprising CDRs 1, 2, and 3 comprising the amino acid sequences of SEQ ID NOs: 34, 38, and 49, respectively, and a light chain variable region comprising CDRs 1, 2, and 3 comprising the amino acid sequences of SEQ ID NOs: 84, 90, and 91, respectively;
(7) an antibody comprising a heavy chain variable region comprising CDRs 1, 2, and 3 comprising the amino acid sequences of SEQ ID NOs: 35, 38, and 49, respectively, and a light chain variable region comprising CDRs 1, 2, and 3 comprising the amino acid sequences of SEQ ID NOs: 84, 90, and 91, respectively;
(8) an antibody comprising a heavy chain variable region comprising CDRs 1, 2, and 3 comprising the amino acid sequences of SEQ ID NOs: 33, 39, and 49, respectively, and a light chain variable region comprising CDRs 1, 2, and 3 comprising the amino acid sequences of SEQ ID NOs: 84, 90, and 91, respectively;
(9) an antibody comprising a heavy chain variable region comprising CDRs 1, 2, and 3 comprising the amino acid sequences of SEQ ID NOs: 33, 40, and 49, respectively, and a light chain variable region comprising CDRs 1, 2, and 3 comprising the amino acid sequences of SEQ ID NOs: 84, 90, and 91, respectively;
(10) an antibody comprising a heavy chain variable region comprising CDRs 1, 2, and 3 comprising the amino acid sequences of SEQ ID NOs: 33, 41, and 49, respectively, and a light chain variable region comprising CDRs 1, 2, and 3 comprising the amino acid sequences of SEQ ID NOs: 84, 90, and 91, respectively;
(11) an antibody comprising a heavy chain variable region comprising CDRs 1, 2, and 3 comprising the amino acid sequences of SEQ ID NOs: 33, 42, and 49, respectively, and a light chain variable region comprising CDRs 1, 2, and 3 comprising the amino acid sequences of SEQ ID NOs: 84, 90, and 91, respectively;
(12) an antibody comprising a heavy chain variable region comprising CDRs 1, 2, and 3 comprising the amino acid sequences of SEQ ID NOs: 33, 43, and 49, respectively, and a light chain variable region comprising CDRs 1, 2, and 3 comprising the amino acid sequences of SEQ ID NOs: 84, 90, and 91, respectively;
(13) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 84, 90, and 91, respectively;
(14) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 85, 90, and 91, respectively;
(15) an antibody comprising a heavy chain variable region comprising CDRs 1, 2, and 3 comprising the amino acid sequences of SEQ ID NOs: 33, 45, and 49, respectively, and a light chain variable region comprising CDRs 1, 2, and 3 comprising the amino acid sequences of SEQ ID NOs: 84, 90, and 91, respectively;
(16) an antibody comprising a heavy chain variable region comprising CDRs 1, 2, and 3 comprising the amino acid sequences of SEQ ID NOs: 33, 46, and 49, respectively, and a light chain variable region comprising CDRs 1, 2, and 3 comprising the amino acid sequences of SEQ ID NOs: 84, 90, and 91, respectively;
(17) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 89, 90, and 91, respectively;
(18) an antibody comprising a heavy chain variable region comprising CDRs 1, 2, and 3 comprising the amino acid sequences of SEQ ID NOs: 36, 38, and 49, respectively, and a light chain variable region comprising CDRs 1, 2, and 3 comprising the amino acid sequences of SEQ ID NOs: 84, 90, and 91, respectively;
(19) an antibody comprising a heavy chain variable region comprising CDRs 1, 2, and 3 comprising the amino acid sequences of SEQ ID NOs: 37, 38, and 49, respectively, and a light chain variable region comprising CDRs 1, 2, and 3 comprising the amino acid sequences of SEQ ID NOs: 84, 90, and 91, respectively;
(20) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 84, 90, and 91, respectively;
(21) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 84, 90, and 91, respectively;
(22) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 85, 90, and 91, respectively;
(23) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 87, 90, and 91, respectively;
(24) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 85, 90, and 91, respectively; and
(25) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 87, 90, and 91, respectively.

7. The antibody of claim 1 comprising the heavy chain variable region of any one of SEQ ID NOs: 2 to 32, and the light chain variable region of any one of SEQ ID NOs: 65 to 83.

8. The antibody of claim 1, wherein the antibody comprises the light chain variable region of (1) with a lysine at position 42 by Kabat numbering.

9. A pharmaceutical composition comprising the antibody of claim 1 as an active ingredient.

10. A method of treating a cancer, the method comprising administering the antibody of claim 1 to a subject identified as having cancer, wherein the cancer comprises cells that express AXL.

11. The method of claim 10, wherein the cancer is pancreatic cancer, gastric cancer, lung cancer, osteosarcoma, colon cancer, prostate cancer, melanoma, endometrial cancer, ovarian cancer, uterine leiomyoma, thyroid cancer, cancer stem cell, breast cancer, bladder cancer, renal cancer, glioma, neuroblastoma, or esophageal cancer.

12. The method of claim 10, wherein the cancer is glioma, gastric cancer, endometrial cancer, non-small-cell lung cancer, pancreatic adenocarcinoma, or breast cancer.

13. The method of claim 10, wherein the cancer is pancreatic adenocarcinoma or breast cancer.

14. The antibody of claim 2, wherein the amino acid residue at position 94 by Kabat numbering in the heavy chain variable region is glycine.

15. The antibody of claim 2, wherein the amino acid sequence of the heavy chain variable region comprises at least one of the following amino acid residues:
(1) the amino acid residue at position 31 by Kabat numbering in the heavy chain variable region is aspartic acid, glutamic acid, lysine, or arginine;
(2) the amino acid residue at position 40 by Kabat numbering in the heavy chain variable region is proline;
(3) the amino acid residue at position 41 by Kabat numbering in the heavy chain variable region is arginine;
(4) the amino acid residue at position 43 by Kabat numbering in the heavy chain variable region is glutamine or glutamic acid;
(5) the amino acid residue at position 44 by Kabat numbering in the heavy chain variable region is arginine;
(6) the amino acid residue at position 48 by Kabat numbering in the heavy chain variable region is isoleucine;
(7) the amino acid residue at position 61 by Kabat numbering in the heavy chain variable region is glutamic acid, lysine, or arginine;
(8) the amino acid residue at position 62 by Kabat numbering in the heavy chain variable region is glutamic acid;
(9) the amino acid residue at position 64 by Kabat numbering in the heavy chain variable region is glutamine;
(10) the amino acid residue at position 65 by Kabat numbering in the heavy chain variable region is aspartic acid;
(11) the amino acid residue at position 73 by Kabat numbering in the heavy chain variable region is asparagine; and
(12) the amino acid residue at position 105 by Kabat numbering in the heavy chain variable region is glutamic acid or arginine.

16. The antibody of claim 2, wherein the amino acid sequence of the light chain variable region comprises at least one of the following amino acid residues:
(1) the amino acid residue at position 17 by Kabat numbering in the light chain variable region is arginine;
(2) the amino acid residue at position 24 by Kabat numbering in the light chain variable region is glutamine;
(3) the amino acid residue at position 27 by Kabat numbering in the light chain variable region is glutamic acid or arginine;
(4) the amino acid residue at position 29 by Kabat numbering in the light chain variable region is alanine;
(5) the amino acid residue at position 42 by Kabat numbering in the light chain variable region is glutamic acid or glutamine;
(6) the amino acid residue at position 45 by Kabat numbering in the light chain variable region is lysine;
(7) the amino acid residue at position 100 by Kabat numbering in the light chain variable region is arginine;
(8) the amino acid residue at position 104 by Kabat numbering in the light chain variable region is valine; and
(9) the amino acid residue at position 107 by Kabat numbering in the light chain variable region is glutamic acid.

17. The antibody of claim 2, comprising at least any one of the following heavy chain variable regions:
(1) a heavy chain variable region comprising a CDR1 comprising the amino acid sequence of SEQ ID NO: 33, a CDR2 comprising the amino acid sequence of SEQ ID NO: 38, and a CDR3 comprising the amino acid sequence of SEQ ID NO: 49;
(2) a heavy chain variable region comprising a CDR1 comprising the amino acid sequence of SEQ ID NO: 34, a CDR2 comprising the amino acid sequence of SEQ ID NO: 38, and a CDR3 comprising the amino acid sequence of SEQ ID NO: 49;
(3) a heavy chain variable region comprising a CDR1 comprising the amino acid sequence of SEQ ID NO: 35, a CDR2 comprising the amino acid sequence of SEQ ID NO: 38, and a CDR3 comprising the amino acid sequence of SEQ ID NO: 49;
(4) a heavy chain variable region comprising a CDR1 comprising the amino acid sequence of SEQ ID NO: 33, a CDR2 comprising the amino acid sequence of SEQ ID NO: 39, and a CDR3 comprising the amino acid sequence of SEQ ID NO: 49;
(5) a heavy chain variable region comprising a CDR1 comprising the amino acid sequence of SEQ ID NO: 33, a CDR2 comprising the amino acid sequence of SEQ ID NO: 40, and a CDR3 comprising the amino acid sequence of SEQ ID NO: 49;
(6) a heavy chain variable region comprising a CDR1 comprising the amino acid sequence of SEQ ID NO: 33, a CDR2 comprising the amino acid sequence of SEQ ID NO: 41, and a CDR3 comprising the amino acid sequence of SEQ ID NO: 49;
(7) a heavy chain variable region comprising a CDR1 comprising the amino acid sequence of SEQ ID NO: 33, a CDR2 comprising the amino acid sequence of SEQ ID NO: 42, and a CDR3 comprising the amino acid sequence of SEQ ID NO: 49;
(8) a heavy chain variable region comprising a CDR1 comprising the amino acid sequence of SEQ ID NO: 33, a CDR2 comprising the amino acid sequence of SEQ ID NO: 43, and a CDR3 comprising the amino acid sequence of SEQ ID NO: 49;
(9) a heavy chain variable region comprising a CDR1 comprising the amino acid sequence of SEQ ID NO: 33, a CDR2 comprising the amino acid sequence of SEQ ID NO: 44, and a CDR3 comprising the amino acid sequence of SEQ ID NO: 49;
(10) a heavy chain variable region comprising a CDR1 comprising the amino acid sequence of SEQ ID NO: 33, a CDR2 comprising the amino acid sequence of SEQ ID NO: 45, and a CDR3 comprising the amino acid sequence of SEQ ID NO: 49;
(11) a heavy chain variable region comprising a CDR1 comprising the amino acid sequence of SEQ ID NO: 33, a CDR2 comprising the amino acid sequence of SEQ ID NO: 46, and a CDR3 comprising the amino acid sequence of SEQ ID NO: 49;
(12) a heavy chain variable region comprising a CDR1 comprising the amino acid sequence of SEQ ID NO: 36, a CDR2 comprising the amino acid sequence of SEQ ID NO: 38, and a CDR3 comprising the amino acid sequence of SEQ ID NO: 49;
(13) a heavy chain variable region comprising a CDR1 comprising the amino acid sequence of SEQ ID NO: 37, a CDR2 comprising the amino acid sequence of SEQ ID NO: 38, and a CDR3 comprising the amino acid sequence of SEQ ID NO: 49;
(14) a heavy chain variable region comprising a CDR1 comprising the amino acid sequence of SEQ ID NO: 33, a CDR2 comprising the amino acid sequence of SEQ ID NO: 47, and a CDR3 comprising the amino acid sequence of SEQ ID NO: 49; and
(15) a heavy chain variable region comprising a CDR1 comprising the amino acid sequence of SEQ ID NO: 33, a CDR2 comprising the amino acid sequence of SEQ ID NO: 48, and a CDR3 comprising the amino acid sequence of SEQ ID NO: 49.

18. The antibody of claim 2, which is selected from the group consisting of (1) to (25) below:
(1) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 84, 90, and 91, respectively;
(2) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 85, 90, and 91, respectively;
(3) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 86, 90, and 91, respectively;
(4) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 87, 90, and 91, respectively;
(5) an antibody comprising a heavy chain variable region comprising CDRs 1, 2, and 3 comprising the amino acid sequences of SEQ ID NOs: 33, 38, and 49, respectively, and a light chain variable region comprising CDRs 1, 2, and 3 comprising the amino acid sequences of SEQ ID NOs: 88, 90, and 91, respectively;
(6) an antibody comprising a heavy chain variable region comprising CDRs 1, 2, and 3 comprising the amino acid sequences of SEQ ID NOs: 34, 38, and 49, respectively, and a light chain variable region comprising CDRs 1, 2, and 3 comprising the amino acid sequences of SEQ ID NOs: 84, 90, and 91, respectively;
(7) an antibody comprising a heavy chain variable region comprising CDRs 1, 2, and 3 comprising the amino acid sequences of SEQ ID NOs: 35, 38, and 49, respectively, and a light chain variable region comprising CDRs 1, 2, and 3 comprising the amino acid sequences of SEQ ID NOs: 84, 90, and 91, respectively;
(8) an antibody comprising a heavy chain variable region comprising CDRs 1, 2, and 3 comprising the amino acid sequences of SEQ ID NOs: 33, 39, and 49, respectively, and a light chain variable region comprising CDRs 1, 2, and 3 comprising the amino acid sequences of SEQ ID NOs: 84, 90, and 91, respectively;
(9) an antibody comprising a heavy chain variable region comprising CDRs 1, 2, and 3 comprising the amino acid sequences of SEQ ID NOs: 33, 40, and 49, respectively, and a light chain variable region comprising CDRs 1, 2, and 3 comprising the amino acid sequences of SEQ ID NOs: 84, 90, and 91, respectively;
(10) an antibody comprising a heavy chain variable region comprising CDRs 1, 2, and 3 comprising the amino acid sequences of SEQ ID NOs: 33, 41, and 49, respectively, and a light chain variable region comprising CDRs 1, 2, and 3 comprising the amino acid sequences of SEQ ID NOs: 84, 90, and 91, respectively;
(11) an antibody comprising a heavy chain variable region comprising CDRs 1, 2, and 3 comprising the amino acid sequences of SEQ ID NOs: 33, 42, and 49, respectively, and a light chain variable region comprising CDRs 1, 2, and 3 comprising the amino acid sequences of SEQ ID NOs: 84, 90, and 91, respectively;
(12) an antibody comprising a heavy chain variable region comprising CDRs 1, 2, and 3 comprising the amino acid sequences of SEQ ID NOs: 33, 43, and 49, respectively, and a light chain variable region comprising CDRs 1, 2, and 3 comprising the amino acid sequences of SEQ ID NOs: 84, 90, and 91, respectively;
(13) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 84, 90, and 91, respectively;
(14) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 85, 90, and 91, respectively;
(15) an antibody comprising a heavy chain variable region comprising CDRs 1, 2, and 3 comprising the amino acid sequences of SEQ ID NOs: 33, 45, and 49, respectively, and a light chain variable region comprising CDRs 1, 2, and 3 comprising the amino acid sequences of SEQ ID NOs: 84, 90, and 91, respectively;
(16) an antibody comprising a heavy chain variable region comprising CDRs 1, 2, and 3 comprising the amino acid sequences of SEQ ID NOs: 33, 46, and 49, respectively, and a light chain variable region comprising CDRs 1, 2, and 3 comprising the amino acid sequences of SEQ ID NOs: 84, 90, and 91, respectively;
(17) an antibody comprising a heavy chain variable region comprising CDRs 1, 2, and 3 comprising the amino acid sequences of SEQ ID NOs: 33, 44, and 49, respectively, and a light chain variable region comprising CDRs 1, 2, and 3 comprising the amino acid sequences of SEQ ID NOs: 89, 90, and 91, respectively;
(18) an antibody comprising a heavy chain variable region comprising CDRs 1, 2, and 3 comprising the amino acid sequences of SEQ ID NOs: 36, 38, and 49, respectively, and a light chain variable region comprising CDRs 1, 2, and 3 comprising the amino acid sequences of SEQ ID NOs: 84, 90, and 91, respectively;
(19) an antibody comprising a heavy chain variable region comprising CDRs 1, 2, and 3 comprising the amino acid sequences of SEQ ID NOs: 37, 38, and 49, respectively, and a light chain variable region comprising CDRs 1, 2, and 3 comprising the amino acid sequences of SEQ ID NOs: 84, 90, and 91, respectively;
(20) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 84, 90, and 91, respectively;
(21) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 84, 90, and 91, respectively;
(22) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 85, 90, and 91, respectively;
(23) an antibody comprising a heavy chain variable region comprising CDRs 1, 2, and 3 comprising the amino acid sequences of SEQ ID NOs: 33, 48, and 49, respectively, and a light chain variable region comprising CDRs 1, 2, and 3 comprising the amino acid sequences of SEQ ID NOs: 87, 90, and 91, respectively;
(24) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 85, 90, and 91, respectively; and
(25) an antibody comprising a heavy chain variable region comprising CDRs 1, 2, and 3 comprising the amino acid sequences of SEQ ID NOs: 33, 47, and 49, respectively, and a light chain variable region comprising CDRs 1, 2, and 3 comprising the amino acid sequences of SEQ ID NOs: 87, 90, and 91, respectively.

19. The antibody of claim 2 comprising the heavy chain variable region of any one of SEQ ID NOs: 2 to 32, and the light chain variable region of any one of SEQ ID NOs: 65 to 83.

20. A method of treating a cancer, the method comprising administering the antibody of claim 2 to a subject identified as having cancer, wherein the cancer comprises cells that express AXL.

21. The method of claim 20, wherein the cancer is pancreatic cancer, gastric cancer, lung cancer, osteosarcoma, colon cancer, prostate cancer, melanoma, endometrial cancer, ovarian cancer, uterine leiomyoma, thyroid cancer, cancer stem cell, breast cancer, bladder cancer, renal cancer, glioma, neuroblastoma, or esophageal cancer.

22. The method of claim 20, wherein the cancer is glioma, gastric cancer, endometrial cancer, non-small-cell lung cancer, pancreatic adenocarcinoma, or breast cancer.

23. The method of claim 20, wherein the cancer is pancreatic adenocarcinoma or breast cancer.

* * * * *

SEQUENCE LISTING

```
<160> NUMBER OF SEQ ID NOS: 117

<210> SEQ ID NO 1
<211> LENGTH: 119
<212> TYPE: PRT
<213> ORGANISM: Artificial
<220> FEATURE:
<223> OTHER INFORMATION: an artificially synthesized sequence

<400> SEQUENCE: 1

Gln Val Gln Leu Lys Gln Ser Gly Pro Gly Leu Val Ala Pro Ser Gln
1               5                   10                  15

Ser Leu Ser Ile Thr Cys Thr Val Ser Gly Leu Ser Leu Thr Ser Phe
            20                  25                  30

Gly Val Asp Trp Val Arg Gln Ser Pro Gly Lys Gly Leu Glu Trp Leu
```

```
            35                  40                  45
Gly Val Ile Trp Gly Gly Ser Thr Asn Tyr Asn Ser Ala Leu Lys
         50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Gly Glu Gly Ser Lys Tyr Gly Ala Trp Phe Ala Tyr Trp Gly Gln Gly
                100                 105                 110

Thr Leu Val Thr Val Ser Ala
        115

<210> SEQ ID NO 2
<211> LENGTH: 119
<212> TYPE: PRT
<213> ORGANISM: Artificial
<220> FEATURE:
<223> OTHER INFORMATION: an artificially synthesized sequence

<400> SEQUENCE: 2

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Ser Phe
                 20                  25                  30

Gly Val Asp Trp Val Arg Gln Ala Pro Gly Lys Gly Leu Glu Trp Met
             35                  40                  45

Gly Val Ile Trp Gly Gly Ser Thr Asn Tyr Asn Ser Ala Leu Lys
         50                  55                  60

Ser Arg Leu Thr Ile Ser Lys Asp Thr Ser Lys Ser Gln Val Val Leu
 65                  70                  75                  80

Thr Met Thr Asn Met Asp Pro Val Asp Thr Ala Thr Tyr Tyr Cys Ala
                 85                  90                  95

Gly Glu Gly Ser Lys Tyr Gly Ala Trp Phe Ala Tyr Trp Gly Gln Gly
                100                 105                 110

Thr Leu Val Thr Val Ser Ser
        115

<210> SEQ ID NO 3
<211> LENGTH: 119
<212> TYPE: PRT
<213> ORGANISM: Artificial
<220> FEATURE:
<223> OTHER INFORMATION: an artificially synthesized sequence

<400> SEQUENCE: 3

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Ser Phe
                 20                  25                  30

Gly Val Asp Trp Val Arg Gln Ala Pro Gly Lys Gly Leu Glu Trp Met
             35                  40                  45

Gly Val Ile Trp Gly Gly Ser Thr Asn Tyr Asn Ser Ala Leu Lys
         50                  55                  60

Ser Arg Leu Thr Ile Ser Lys Asp Asn Ser Lys Ser Gln Val Val Leu
 65                  70                  75                  80

Thr Met Thr Asn Met Asp Pro Val Asp Thr Ala Thr Tyr Tyr Cys Ala
                 85                  90                  95
```

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 4
<211> LENGTH: 119
<212> TYPE: PRT
<213> ORGANISM: Artificial
<220> FEATURE:
<223> OTHER INFORMATION: an artificially synthesized sequence

<400> SEQUENCE: 4

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asp Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial
<220> FEATURE:
<223> OTHER INFORMATION: an artificially synthesized sequence

<400> SEQUENCE: 5

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Glu Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial

<220> FEATURE:
<223> OTHER INFORMATION: an artificially synthesized sequence

<400> SEQUENCE: 6

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Gln Gly Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 7
<211> LENGTH: 119
<212> TYPE: PRT
<213> ORGANISM: Artificial
<220> FEATURE:
<223> OTHER INFORMATION: an artificially synthesized sequence

<400> SEQUENCE: 7

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Pro Pro Gly Gln Gly Leu Glu Trp Ile
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 8
<211> LENGTH: 119
<212> TYPE: PRT
<213> ORGANISM: Artificial
<220> FEATURE:
<223> OTHER INFORMATION: an artificially synthesized sequence

<400> SEQUENCE: 8

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
            35                  40                  45

Gly Val Ile Trp Gly Gly Ser Thr Asn Tyr Asn Glu Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
            115

<210> SEQ ID NO 9
<211> LENGTH: 119
<212> TYPE: PRT
<213> ORGANISM: Artificial
<220> FEATURE:
<223> OTHER INFORMATION: an artificially synthesized sequence

<400> SEQUENCE: 9

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
                20                  25                  30

Gly Val Asp Trp Val Arg Gln Ala Pro Gly Lys Gly Leu Glu Trp Met
            35                  40                  45

Gly Val Ile Trp Gly Gly Ser Thr Asn Tyr Asn Ser Glu Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
            115

<210> SEQ ID NO 10
<211> LENGTH: 119
<212> TYPE: PRT
<213> ORGANISM: Artificial
<220> FEATURE:
<223> OTHER INFORMATION: an artificially synthesized sequence

<400> SEQUENCE: 10

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
                20                  25                  30

Gly Val Asp Trp Val Arg Gln Ala Pro Gly Lys Gly Leu Glu Trp Met
            35                  40                  45

Gly Val Ile Trp Gly Gly Ser Thr Asn Tyr Asn Ser Ala Leu Gln
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
                100                 105                 110

Thr Leu Val Thr Val Ser Ser
        115

<210> SEQ ID NO 11
<211> LENGTH: 119
<212> TYPE: PRT
<213> ORGANISM: Artificial
<220> FEATURE:
<223> OTHER INFORMATION: an artificially synthesized sequence

<400> SEQUENCE: 11

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Lys
    50                  55                  60

Asp Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
                100                 105                 110

Thr Leu Val Thr Val Ser Ser
        115

<210> SEQ ID NO 12
<211> LENGTH: 119
<212> TYPE: PRT
<213> ORGANISM: Artificial
<220> FEATURE:
<223> OTHER INFORMATION: an artificially synthesized sequence

<400> SEQUENCE: 12

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Gln
    50                  55                  60

Asp Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
                100                 105                 110

Thr Leu Val Thr Val Ser Ser
        115

<210> SEQ ID NO 13
<211> LENGTH: 119
<212> TYPE: PRT

<213> ORGANISM: Artificial
<220> FEATURE:
<223> OTHER INFORMATION: an artificially synthesized sequence

<400> SEQUENCE: 13

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Ser Phe
            20                  25                  30
Gly Val Asp Trp Val Arg Gln Ala Pro Gly Lys Gly Leu Glu Trp Met
        35                  40                  45
Gly Val Ile Trp Gly Gly Ser Thr Asn Tyr Asn Glu Ala Leu Gln
    50                  55                  60
Asp Arg Leu Thr Ile Ser Lys Asp Asn Ser Lys Ser Gln Val Val Leu
65                  70                  75                  80
Thr Met Thr Asn Met Asp Pro Val Asp Thr Ala Thr Tyr Tyr Cys Ala
                85                  90                  95
Gly Glu Gly Ser Lys Tyr Gly Ala Trp Phe Ala Tyr Trp Gly Gln Gly
            100                 105                 110
Thr Leu Val Thr Val Ser Ser
        115
```

<210> SEQ ID NO 14
<211> LENGTH: 119
<212> TYPE: PRT
<213> ORGANISM: Artificial
<220> FEATURE:
<223> OTHER INFORMATION: an artificially synthesized sequence

<400> SEQUENCE: 14

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Ser Phe
            20                  25                  30
Gly Val Asp Trp Val Arg Gln Ala Pro Gly Lys Gly Leu Glu Trp Met
        35                  40                  45
Gly Val Ile Trp Gly Gly Ser Thr Asn Tyr Asn Ser Glu Leu Gln
    50                  55                  60
Asp Arg Leu Thr Ile Ser Lys Asp Asn Ser Lys Ser Gln Val Val Leu
65                  70                  75                  80
Thr Met Thr Asn Met Asp Pro Val Asp Thr Ala Thr Tyr Tyr Cys Ala
                85                  90                  95
Gly Glu Gly Ser Lys Tyr Gly Ala Trp Phe Ala Tyr Trp Gly Gln Gly
            100                 105                 110
Thr Leu Val Thr Val Ser Ser
        115
```

<210> SEQ ID NO 15
<211> LENGTH: 119
<212> TYPE: PRT
<213> ORGANISM: Artificial
<220> FEATURE:
<223> OTHER INFORMATION: an artificially synthesized sequence

<400> SEQUENCE: 15

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Ser Phe
            20                  25                  30
```

Gly Val Asp Trp Val Arg Gln Ala Pro Gly Lys Gly Leu Glu Trp Met
            35                  40                  45

Gly Val Ile Trp Gly Gly Ser Thr Asn Tyr Asn Glu Glu Leu Gln
        50                  55                  60

Asp Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
            115

<210> SEQ ID NO 16
<211> LENGTH: 119
<212> TYPE: PRT
<213> ORGANISM: Artificial
<220> FEATURE:
<223> OTHER INFORMATION: an artificially synthesized sequence

<400> SEQUENCE: 16

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
            35                  40                  45

Gly Val Ile Trp Gly Gly Ser Thr Asn Tyr Asn Ser Ala Leu Lys
        50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Glu Gly
            100                 105                 110

Thr Leu Val Thr Val Ser Ser
            115

<210> SEQ ID NO 17
<211> LENGTH: 119
<212> TYPE: PRT
<213> ORGANISM: Artificial
<220> FEATURE:
<223> OTHER INFORMATION: an artificially synthesized sequence

<400> SEQUENCE: 17

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Gln Gly Leu Glu Trp Met
            35                  40                  45

Gly Val Ile Trp Gly Gly Ser Thr Asn Tyr Asn Glu Ala Leu Gln
        50                  55                  60

Asp Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala

```
                        85                  90                  95

Gly Glu Gly Ser Lys Tyr Gly Ala Trp Phe Ala Tyr Trp Gly Gln Gly
                100                 105                 110

Thr Leu Val Thr Val Ser Ser
            115

<210> SEQ ID NO 18
<211> LENGTH: 119
<212> TYPE: PRT
<213> ORGANISM: Artificial
<220> FEATURE:
<223> OTHER INFORMATION: an artificially synthesized sequence

<400> SEQUENCE: 18

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
                20                  25                  30

Gly Val Asp Trp Val Arg Gln Ala Pro Gly Lys Gly Leu Glu Trp Met
            35                  40                  45

Gly Val Ile Trp Gly Gly Gly Ser Thr Asn Tyr Asn Glu Ala Leu Gln
        50                  55                  60

Asp Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Glu Gly
                100                 105                 110

Thr Leu Val Thr Val Ser Ser
            115

<210> SEQ ID NO 19
<211> LENGTH: 119
<212> TYPE: PRT
<213> ORGANISM: Artificial
<220> FEATURE:
<223> OTHER INFORMATION: an artificially synthesized sequence

<400> SEQUENCE: 19

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
                20                  25                  30

Gly Val Asp Trp Val Arg Gln Ala Pro Gly Gln Gly Leu Glu Trp Met
            35                  40                  45

Gly Val Ile Trp Gly Gly Gly Ser Thr Asn Tyr Asn Glu Ala Leu Gln
        50                  55                  60

Asp Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Glu Gly
                100                 105                 110

Thr Leu Val Thr Val Ser Ser
            115

<210> SEQ ID NO 20
<211> LENGTH: 119
```

```
<212> TYPE: PRT
<213> ORGANISM: Artificial
<220> FEATURE:
<223> OTHER INFORMATION: an artificially synthesized sequence

<400> SEQUENCE: 20

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Lys Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: Artificial
<220> FEATURE:
<223> OTHER INFORMATION: an artificially synthesized sequence

<400> SEQUENCE: 21

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 22
<211> LENGTH: 119
<212> TYPE: PRT
<213> ORGANISM: Artificial
<220> FEATURE:
<223> OTHER INFORMATION: an artificially synthesized sequence

<400> SEQUENCE: 22

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
```

```
                    20                  25                  30
Gly Val Asp Trp Val Arg Gln Ala Arg Gly Gln Arg Leu Glu Trp Met
            35                  40                  45

Gly Val Ile Trp Gly Gly Ser Thr Asn Tyr Asn Ser Ala Leu Lys
        50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
            115

<210> SEQ ID NO 23
<211> LENGTH: 119
<212> TYPE: PRT
<213> ORGANISM: Artificial
<220> FEATURE:
<223> OTHER INFORMATION: an artificially synthesized sequence

<400> SEQUENCE: 23

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
            35                  40                  45

Gly Val Ile Trp Gly Gly Gly Ser Thr Asn Tyr Asn Arg Ala Leu Lys
        50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
            115

<210> SEQ ID NO 24
<211> LENGTH: 119
<212> TYPE: PRT
<213> ORGANISM: Artificial
<220> FEATURE:
<223> OTHER INFORMATION: an artificially synthesized sequence

<400> SEQUENCE: 24

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
            35                  40                  45

Gly Val Ile Trp Gly Gly Gly Ser Thr Asn Tyr Asn Lys Ala Leu Lys
        50                  55                  60

Ser Arg Leu Thr Ile Ser Lys Asp Asn Ser Lys Ser Gln Val Val Leu
65                  70                  75                  80
```

```
Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 25
<211> LENGTH: 119
<212> TYPE: PRT
<213> ORGANISM: Artificial
<220> FEATURE:
<223> OTHER INFORMATION: an artificially synthesized sequence

<400> SEQUENCE: 25

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Pro Gly Lys Gly Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Arg Gly
            100                 105                 110

Thr Leu Val Thr Val Ser Ser
        115

<210> SEQ ID NO 26
<211> LENGTH: 119
<212> TYPE: PRT
<213> ORGANISM: Artificial
<220> FEATURE:
<223> OTHER INFORMATION: an artificially synthesized sequence

<400> SEQUENCE: 26

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Lys Phe
            20                  25                  30

Gly Val Asp Trp Val Arg Gln Ala Arg Gly Gln Arg Leu Glu Trp Met
        35                  40                  45

Gly Val Ile Trp Gly Gly Gly Ser Thr Asn Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
            100                 105                 110

Thr Leu Val Thr Val Ser Ser
        115

<210> SEQ ID NO 27
```

<211> LENGTH: 119
<212> TYPE: PRT
<213> ORGANISM: Artificial
<220> FEATURE:
<223> OTHER INFORMATION: an artificially synthesized sequence

<400> SEQUENCE: 27

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Arg Phe
            20                  25                  30
Gly Val Asp Trp Val Arg Gln Ala Arg Gly Gln Arg Leu Glu Trp Met
        35                  40                  45
Gly Val Ile Trp Gly Gly Gly Ser Thr Asn Tyr Asn Ser Ala Leu Lys
    50                  55                  60
Ser Arg Leu Thr Ile Ser Lys Asp Asn Ser Lys Ser Gln Val Val Leu
65                  70                  75                  80
Thr Met Thr Asn Met Asp Pro Val Asp Thr Ala Thr Tyr Tyr Cys Ala
                85                  90                  95
Gly Glu Gly Ser Lys Tyr Gly Ala Trp Phe Ala Tyr Trp Gly Gln Gly
            100                 105                 110
Thr Leu Val Thr Val Ser Ser
        115
```

<210> SEQ ID NO 28
<211> LENGTH: 119
<212> TYPE: PRT
<213> ORGANISM: Artificial
<220> FEATURE:
<223> OTHER INFORMATION: an artificially synthesized sequence

<400> SEQUENCE: 28

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Ser Phe
            20                  25                  30
Gly Val Asp Trp Val Arg Gln Ala Arg Gly Gln Arg Leu Glu Trp Met
        35                  40                  45
Gly Val Ile Trp Gly Gly Gly Ser Thr Asn Tyr Asn Lys Ala Leu Lys
    50                  55                  60
Ser Arg Leu Thr Ile Ser Lys Asp Asn Ser Lys Ser Gln Val Val Leu
65                  70                  75                  80
Thr Met Thr Asn Met Asp Pro Val Asp Thr Ala Thr Tyr Tyr Cys Ala
                85                  90                  95
Gly Glu Gly Ser Lys Tyr Gly Ala Trp Phe Ala Tyr Trp Gly Gln Gly
            100                 105                 110
Thr Leu Val Thr Val Ser Ser
        115
```

<210> SEQ ID NO 29
<211> LENGTH: 119
<212> TYPE: PRT
<213> ORGANISM: Artificial
<220> FEATURE:
<223> OTHER INFORMATION: an artificially synthesized sequence

<400> SEQUENCE: 29

```
Gln Val Thr Leu Lys Glu Ser Gly Pro Val Leu Val Lys Pro Thr Glu
1               5                   10                  15
```

Thr Leu Thr Leu Thr Cys Thr Val Ser Gly Phe Ser Leu Ser Ser Phe
            20                  25                  30

Gly Val Asp Trp Val Arg Gln Ala Arg Gly Gln Arg Leu Glu Trp Met
            35                  40                  45

Gly Val Ile Trp Gly Gly Gly Ser Thr Asn Tyr Asn Arg Ala Leu Lys
        50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Gln Gly
                100                 105                 110

Thr Leu Val Thr Val Ser Ser
            115

<210> SEQ ID NO 30
<211> LENGTH: 119
<212> TYPE: PRT
<213> ORGANISM: Artificial
<220> FEATURE:
<223> OTHER INFORMATION: an artificially synthesized sequence

<400> SEQUENCE: 30

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Arg Gly Gln Arg Leu Glu Trp Met
            35                  40                  45

Gly Val Ile Trp Gly Gly Gly Ser Thr Asn Tyr Asn Ser Ala Leu Lys
        50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Arg Gly
                100                 105                 110

Thr Leu Val Thr Val Ser Ser
            115

<210> SEQ ID NO 31
<211> LENGTH: 119
<212> TYPE: PRT
<213> ORGANISM: Artificial
<220> FEATURE:
<223> OTHER INFORMATION: an artificially synthesized sequence

<400> SEQUENCE: 31

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Arg Gly Gln Arg Leu Glu Trp Met
            35                  40                  45

Gly Val Ile Trp Gly Gly Gly Ser Thr Asn Tyr Asn Lys Ala Leu Lys
        50                  55                  60

Ser Arg Leu Thr Ile Ser Lys Asp Asn Ser Lys Ser Gln Val Val Leu
65                  70                  75                  80

```
Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Arg Gly
            100                 105                 110

Thr Leu Val Thr Val Ser Ser
        115

<210> SEQ ID NO 32
<211> LENGTH: 119
<212> TYPE: PRT
<213> ORGANISM: Artificial
<220> FEATURE:
<223> OTHER INFORMATION: an artificially synthesized sequence

<400> SEQUENCE: 32

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Phe
            20                  25                  30

Gly Val Asp Trp Val Arg Gln Ala Arg Gly Gln Arg Leu Glu Trp Met
        35                  40                  45

Gly Val Ile Trp Gly Gly Gly Ser Thr Asn Tyr Asn Arg Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Gly Glu Gly Ser Lys Tyr Gly Ala Trp Phe Ala Tyr Trp Gly Arg Gly
            100                 105                 110

Thr Leu Val Thr Val Ser Ser
        115

<210> SEQ ID NO 33
<211> LENGTH: 5
<212> TYPE: PRT
<213> ORGANISM: Artificial
<220> FEATURE:
<223> OTHER INFORMATION: an artificially synthesized sequence

<400> SEQUENCE: 33

Ser Phe Gly Val Asp
1               5

<210> SEQ ID NO 34
<211> LENGTH: 5
<212> TYPE: PRT
<213> ORGANISM: Artificial
<220> FEATURE:
<223> OTHER INFORMATION: an artificially synthesized sequence

<400> SEQUENCE: 34

Asp Phe Gly Val Asp
1               5

<210> SEQ ID NO 35
<211> LENGTH: 5
<212> TYPE: PRT
<213> ORGANISM: Artificial
<220> FEATURE:
<223> OTHER INFORMATION: an artificially synthesized sequence

<400> SEQUENCE: 35
```

```
Glu Phe Gly Val Asp
1               5

<210> SEQ ID NO 36
<211> LENGTH: 5
<212> TYPE: PRT
<213> ORGANISM: Artificial
<220> FEATURE:
<223> OTHER INFORMATION: an artificially synthesized sequence

<400> SEQUENCE: 36

Lys Phe Gly Val Asp
1               5

<210> SEQ ID NO 37
<211> LENGTH: 5
<212> TYPE: PRT
<213> ORGANISM: Artificial
<220> FEATURE:
<223> OTHER INFORMATION: an artificially synthesized sequence

<400> SEQUENCE: 37

Arg Phe Gly Val Asp
1               5

<210> SEQ ID NO 38
<211> LENGTH: 16
<212> TYPE: PRT
<213> ORGANISM: Artificial
<220> FEATURE:
<223> OTHER INFORMATION: an artificially synthesized sequence

<400> SEQUENCE: 38

Val Ile Trp Gly Gly Gly Ser Thr Asn Tyr Asn Ser Ala Leu Lys Ser
1               5                   10                  15

<210> SEQ ID NO 39
<211> LENGTH: 16
<212> TYPE: PRT
<213> ORGANISM: Artificial
<220> FEATURE:
<223> OTHER INFORMATION: an artificially synthesized sequence

<400> SEQUENCE: 39

Val Ile Trp Gly Gly Gly Ser Thr Asn Tyr Asn Glu Ala Leu Lys Ser
1               5                   10                  15

<210> SEQ ID NO 40
<211> LENGTH: 16
<212> TYPE: PRT
<213> ORGANISM: Artificial
<220> FEATURE:
<223> OTHER INFORMATION: an artificially synthesized sequence

<400> SEQUENCE: 40

Val Ile Trp Gly Gly Gly Ser Thr Asn Tyr Asn Ser Glu Leu Lys Ser
1               5                   10                  15

<210> SEQ ID NO 41
<211> LENGTH: 16
<212> TYPE: PRT
<213> ORGANISM: Artificial
<220> FEATURE:
<223> OTHER INFORMATION: an artificially synthesized sequence

<400> SEQUENCE: 41
```

```
Val Ile Trp Gly Gly Gly Ser Thr Asn Tyr Asn Ser Ala Leu Gln Ser
1               5                   10                  15

<210> SEQ ID NO 42
<211> LENGTH: 16
<212> TYPE: PRT
<213> ORGANISM: Artificial
<220> FEATURE:
<223> OTHER INFORMATION: an artificially synthesized sequence

<400> SEQUENCE: 42

Val Ile Trp Gly Gly Gly Ser Thr Asn Tyr Asn Ser Ala Leu Lys Asp
1               5                   10                  15

<210> SEQ ID NO 43
<211> LENGTH: 16
<212> TYPE: PRT
<213> ORGANISM: Artificial
<220> FEATURE:
<223> OTHER INFORMATION: an artificially synthesized sequence

<400> SEQUENCE: 43

Val Ile Trp Gly Gly Gly Ser Thr Asn Tyr Asn Ser Ala Leu Gln Asp
1               5                   10                  15

<210> SEQ ID NO 44
<211> LENGTH: 16
<212> TYPE: PRT
<213> ORGANISM: Artificial
<220> FEATURE:
<223> OTHER INFORMATION: an artificially synthesized sequence

<400> SEQUENCE: 44

Val Ile Trp Gly Gly Gly Ser Thr Asn Tyr Asn Glu Ala Leu Gln Asp
1               5                   10                  15

<210> SEQ ID NO 45
<211> LENGTH: 16
<212> TYPE: PRT
<213> ORGANISM: Artificial
<220> FEATURE:
<223> OTHER INFORMATION: an artificially synthesized sequence

<400> SEQUENCE: 45

Val Ile Trp Gly Gly Gly Ser Thr Asn Tyr Asn Ser Glu Leu Gln Asp
1               5                   10                  15

<210> SEQ ID NO 46
<211> LENGTH: 16
<212> TYPE: PRT
<213> ORGANISM: Artificial
<220> FEATURE:
<223> OTHER INFORMATION: an artificially synthesized sequence

<400> SEQUENCE: 46

Val Ile Trp Gly Gly Gly Ser Thr Asn Tyr Asn Glu Glu Leu Gln Asp
1               5                   10                  15

<210> SEQ ID NO 47
<211> LENGTH: 16
<212> TYPE: PRT
<213> ORGANISM: Artificial
<220> FEATURE:
<223> OTHER INFORMATION: an artificially synthesized sequence

<400> SEQUENCE: 47

Val Ile Trp Gly Gly Gly Ser Thr Asn Tyr Asn Arg Ala Leu Lys Ser
```

<210> SEQ ID NO 48
<211> LENGTH: 16
<212> TYPE: PRT
<213> ORGANISM: Artificial
<220> FEATURE:
<223> OTHER INFORMATION: an artificially synthesized sequence

<400> SEQUENCE: 48

Val Ile Trp Gly Gly Gly Ser Thr Asn Tyr Asn Lys Ala Leu Lys Ser
1               5                   10                  15

<210> SEQ ID NO 49
<211> LENGTH: 11
<212> TYPE: PRT
<213> ORGANISM: Artificial
<220> FEATURE:
<223> OTHER INFORMATION: an artificially synthesized sequence

<400> SEQUENCE: 49

Glu Gly Ser Lys Tyr Gly Ala Trp Phe Ala Tyr
1               5                   10

<210> SEQ ID NO 50
<211> LENGTH: 30
<212> TYPE: PRT
<213> ORGANISM: Artificial
<220> FEATURE:
<223> OTHER INFORMATION: an artificially synthesized sequence

<400> SEQUENCE: 50

Gln Val Gln Leu Lys Gln Ser Gly Pro Gly Leu Val Ala Pro Ser Gln
1               5                   10                  15
Ser Leu Ser Ile Thr Cys Thr Val Ser Gly Leu Ser Leu Thr
            20                  25                  30

<210> SEQ ID NO 51
<211> LENGTH: 30
<212> TYPE: PRT
<213> ORGANISM: Artificial
<220> FEATURE:
<223> OTHER INFORMATION: an artificially synthesized sequence

<400> SEQUENCE: 51

Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser
            20                  25                  30

<210> SEQ ID NO 52
<211> LENGTH: 14
<212> TYPE: PRT
<213> ORGANISM: Artificial
<220> FEATURE:
<223> OTHER INFORMATION: an artificially synthesized sequence

<400> SEQUENCE: 52

Trp Val Arg Gln Ser Pro Gly Lys Gly Leu Glu Trp Leu Gly
1               5                   10

<210> SEQ ID NO 53
<211> LENGTH: 14
<212> TYPE: PRT
<213> ORGANISM: Artificial
<220> FEATURE:

```
<223> OTHER INFORMATION: an artificially synthesized sequence

<400> SEQUENCE: 53

Trp Val Arg Gln Ala Pro Gly Lys Gly Leu Glu Trp Met Gly
1               5                   10

<210> SEQ ID NO 54
<211> LENGTH: 14
<212> TYPE: PRT
<213> ORGANISM: Artificial
<220> FEATURE:
<223> OTHER INFORMATION: an artificially synthesized sequence

<400> SEQUENCE: 54

Trp Val Arg Gln Ala Pro Gly Gln Gly Leu Glu Trp Met Gly
1               5                   10

<210> SEQ ID NO 55
<211> LENGTH: 14
<212> TYPE: PRT
<213> ORGANISM: Artificial
<220> FEATURE:
<223> OTHER INFORMATION: an artificially synthesized sequence

<400> SEQUENCE: 55

Trp Val Arg Gln Pro Pro Gly Glu Gly Leu Glu Trp Ile Gly
1               5                   10

<210> SEQ ID NO 56
<211> LENGTH: 14
<212> TYPE: PRT
<213> ORGANISM: Artificial
<220> FEATURE:
<223> OTHER INFORMATION: an artificially synthesized sequence

<400> SEQUENCE: 56

Trp Val Arg Gln Ala Arg Gly Gln Arg Leu Glu Trp Met Gly
1               5                   10

<210> SEQ ID NO 57
<211> LENGTH: 32
<212> TYPE: PRT
<213> ORGANISM: Artificial
<220> FEATURE:
<223> OTHER INFORMATION: an artificially synthesized sequence

<400> SEQUENCE: 57

Arg Leu Ser Ile Ser Lys Asp Asn Ser Lys Ser Gln Val Phe Leu Lys
1               5                   10                  15

Met Asn Ser Leu Gln Thr Asp Asp Thr Ala Met Tyr Tyr Cys Ala Gly
            20                  25                  30

<210> SEQ ID NO 58
<211> LENGTH: 32
<212> TYPE: PRT
<213> ORGANISM: Artificial
<220> FEATURE:
<223> OTHER INFORMATION: an artificially synthesized sequence

<400> SEQUENCE: 58

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Gly
            20                  25                  30
```

```
<210> SEQ ID NO 59
<211> LENGTH: 32
<212> TYPE: PRT
<213> ORGANISM: Artificial
<220> FEATURE:
<223> OTHER INFORMATION: an artificially synthesized sequence

<400> SEQUENCE: 59

Arg Leu Thr Ile Ser Lys Asp Asn Ser Lys Ser Gln Val Val Leu Thr
1               5                   10                  15

Met Thr Asn Met Asp Pro Val Asp Thr Ala Thr Tyr Tyr Cys Ala Gly
            20                  25                  30

<210> SEQ ID NO 60
<211> LENGTH: 11
<212> TYPE: PRT
<213> ORGANISM: Artificial
<220> FEATURE:
<223> OTHER INFORMATION: an artificially synthesized sequence

<400> SEQUENCE: 60

Trp Gly Gln Gly Thr Leu Val Thr Val Ser Ala
1               5                   10

<210> SEQ ID NO 61
<211> LENGTH: 11
<212> TYPE: PRT
<213> ORGANISM: Artificial
<220> FEATURE:
<223> OTHER INFORMATION: an artificially synthesized sequence

<400> SEQUENCE: 61

Trp Gly Gln Gly Thr Leu Val Thr Val Ser Ser
1               5                   10

<210> SEQ ID NO 62
<211> LENGTH: 11
<212> TYPE: PRT
<213> ORGANISM: Artificial
<220> FEATURE:
<223> OTHER INFORMATION: an artificially synthesized sequence

<400> SEQUENCE: 62

Trp Gly Glu Gly Thr Leu Val Thr Val Ser Ser
1               5                   10

<210> SEQ ID NO 63
<211> LENGTH: 11
<212> TYPE: PRT
<213> ORGANISM: Artificial
<220> FEATURE:
<223> OTHER INFORMATION: an artificially synthesized sequence

<400> SEQUENCE: 63

Trp Gly Arg Gly Thr Leu Val Thr Val Ser Ser
1               5                   10

<210> SEQ ID NO 64
<211> LENGTH: 112
<212> TYPE: PRT
<213> ORGANISM: Artificial
<220> FEATURE:
<223> OTHER INFORMATION: an artificially synthesized sequence

<400> SEQUENCE: 64

Asp Val Leu Met Thr Gln Thr Pro Leu Ser Leu Pro Val Ser Leu Gly
1               5                   10                  15
```

```
Asp Gln Ala Ser Ile Ser Cys Arg Ser Ser Gln Asn Ile Val His Thr
            20                  25                  30

Asn Gly Asn Thr Tyr Leu Glu Trp Tyr Leu Gln Lys Pro Gly Gln Ser
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Phe Thr Phe Gly Thr Gly Thr Lys Leu Glu Ile Lys
            100                 105                 110
```

<210> SEQ ID NO 65
<211> LENGTH: 112
<212> TYPE: PRT
<213> ORGANISM: Artificial
<220> FEATURE:
<223> OTHER INFORMATION: an artificially synthesized sequence

<400> SEQUENCE: 65

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Thr
            20                  25                  30

Asn Gly Asn Thr Tyr Leu Glu Trp Tyr Gln Gln Lys Pro Gly Lys Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Leu Glu Ile Lys
            100                 105                 110
```

<210> SEQ ID NO 66
<211> LENGTH: 112
<212> TYPE: PRT
<213> ORGANISM: Artificial
<220> FEATURE:
<223> OTHER INFORMATION: an artificially synthesized sequence

<400> SEQUENCE: 66

```
Asp Val Val Met Thr Gln Ser Pro Leu Ser Leu Pro Val Thr Leu Gly
1               5                   10                  15

Gln Pro Ala Ser Ile Ser Cys Gln Ser Ser Gln Asn Ile Val His Thr
            20                  25                  30

Asn Gly Asn Thr Tyr Leu Glu Trp Tyr Gln Gln Lys Pro Gly Lys Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Leu Glu Ile Lys
```

<210> SEQ ID NO 67
<211> LENGTH: 112
<212> TYPE: PRT
<213> ORGANISM: Artificial
<220> FEATURE:
<223> OTHER INFORMATION: an artificially synthesized sequence

<400> SEQUENCE: 67

Asp Val Val Met Thr Gln Ser Pro Leu Ser Leu Pro Val Thr Leu Gly
1               5                   10                  15

Gln Pro Ala Ser Ile Ser Cys Gln Ser Ser Glu Asn Ile Val His Thr
            20                  25                  30

Asn Gly Asn Thr Tyr Leu Glu Trp Tyr Gln Gln Lys Pro Gly Lys Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Leu Glu Ile Lys
            100                 105                 110

<210> SEQ ID NO 68
<211> LENGTH: 112
<212> TYPE: PRT
<213> ORGANISM: Artificial
<220> FEATURE:
<223> OTHER INFORMATION: an artificially synthesized sequence

<400> SEQUENCE: 68

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Thr
            20                  25                  30

Asn Gly Asn Thr Tyr Leu Glu Trp Tyr Gln Gln Lys Pro Gly Glu Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Leu Glu Ile Lys
            100                 105                 110

<210> SEQ ID NO 69
<211> LENGTH: 112
<212> TYPE: PRT
<213> ORGANISM: Artificial
<220> FEATURE:
<223> OTHER INFORMATION: an artificially synthesized sequence

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Thr
            20                  25                  30

```
Asn Gly Asn Thr Tyr Leu Glu Trp Tyr Gln Gln Lys Pro Gly Gln Ala
            35                  40                  45

Pro Glu Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Leu Glu Ile Lys
                100                 105                 110
```

<210> SEQ ID NO 70
<211> LENGTH: 112
<212> TYPE: PRT
<213> ORGANISM: Artificial
<220> FEATURE:
<223> OTHER INFORMATION: an artificially synthesized sequence

<400> SEQUENCE: 70

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Asn Ile Val His Thr
                 20                  25                  30

Asn Gly Asn Thr Tyr Leu Glu Trp Tyr Gln Gln Lys Pro Gly Lys Ala
            35                  40                  45

Pro Glu Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Val Glu Ile Glu
                100                 105                 110
```

<210> SEQ ID NO 71
<211> LENGTH: 112
<212> TYPE: PRT
<213> ORGANISM: Artificial
<220> FEATURE:
<223> OTHER INFORMATION: an artificially synthesized sequence

<400> SEQUENCE: 71

```
Asp Val Val Met Thr Gln Ser Pro Leu Ser Leu Pro Val Thr Leu Gly
 1               5                  10                  15

Gln Pro Ala Ser Ile Ser Cys Gln Ser Ser Gln Asn Ile Val His Thr
                 20                  25                  30

Asn Gly Asn Thr Tyr Leu Glu Trp Tyr Gln Gln Lys Pro Gly Lys Ala
            35                  40                  45

Pro Glu Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Val Glu Ile Glu
                100                 105                 110
```

-continued

```
<210> SEQ ID NO 72
<211> LENGTH: 112
<212> TYPE: PRT
<213> ORGANISM: Artificial
<220> FEATURE:
<223> OTHER INFORMATION: an artificially synthesized sequence

<400> SEQUENCE: 72

Asp Val Val Met Thr Gln Ser Pro Leu Ser Leu Pro Val Thr Leu Gly
1               5                   10                  15

Gln Pro Ala Ser Ile Ser Cys Gln Ser Gln Asn Ile Val His Thr
            20                  25                  30

Asn Gly Asn Thr Tyr Leu Glu Trp Tyr Gln Gln Lys Pro Gly Glu Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Val Glu Ile Glu
            100                 105                 110

<210> SEQ ID NO 73
<211> LENGTH: 112
<212> TYPE: PRT
<213> ORGANISM: Artificial
<220> FEATURE:
<223> OTHER INFORMATION: an artificially synthesized sequence

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Gln Ser Gln Asn Ile Val His Thr
            20                  25                  30

Asn Gly Asn Thr Tyr Leu Glu Trp Tyr Gln Gln Lys Pro Gly Gln Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Val Glu Ile Glu
            100                 105                 110

<210> SEQ ID NO 74
<211> LENGTH: 112
<212> TYPE: PRT
<213> ORGANISM: Artificial
<220> FEATURE:
<223> OTHER INFORMATION: an artificially synthesized sequence

<400> SEQUENCE: 74

Asp Val Val Met Thr Gln Ser Pro Leu Ser Leu Pro Val Thr Leu Gly
1               5                   10                  15

Arg Pro Ala Ser Ile Ser Cys Arg Ser Ser Gln Asn Ile Val His Thr
            20                  25                  30

Asn Gly Asn Thr Tyr Leu Glu Trp Tyr Gln Gln Lys Pro Gly Lys Ala
        35                  40                  45
```

Pro Glu Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Leu Glu Ile Lys
            100                 105                 110

<210> SEQ ID NO 75
<211> LENGTH: 112
<212> TYPE: PRT
<213> ORGANISM: Artificial
<220> FEATURE:
<223> OTHER INFORMATION: an artificially synthesized sequence

<400> SEQUENCE: 75

Asp Val Val Met Thr Gln Ser Pro Leu Ser Leu Pro Val Thr Leu Gly
 1               5                  10                  15

Gln Pro Ala Ser Ile Ser Cys Arg Ser Arg Asn Ile Val His Thr
                 20                  25                  30

Asn Gly Asn Thr Tyr Leu Glu Trp Tyr Gln Gln Lys Pro Gly Lys Ala
             35                  40                  45

Pro Glu Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Leu Glu Ile Lys
            100                 105                 110

<210> SEQ ID NO 76
<211> LENGTH: 112
<212> TYPE: PRT
<213> ORGANISM: Artificial
<220> FEATURE:
<223> OTHER INFORMATION: an artificially synthesized sequence

<400> SEQUENCE: 76

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Asn Ile Val His Thr
                 20                  25                  30

Asn Gly Asn Thr Tyr Leu Glu Trp Tyr Gln Gln Lys Pro Gly Lys Ala
             35                  40                  45

Pro Lys Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Leu Glu Ile Lys
            100                 105                 110

<210> SEQ ID NO 77
<211> LENGTH: 112
<212> TYPE: PRT

<213> ORGANISM: Artificial
<220> FEATURE:
<223> OTHER INFORMATION: an artificially synthesized sequence

<400> SEQUENCE: 77

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Thr
            20                  25                  30

Asn Gly Asn Thr Tyr Leu Glu Trp Tyr Gln Gln Lys Pro Gly Lys Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Arg Gly Thr Lys Leu Glu Ile Lys
                100                 105                 110
```

<210> SEQ ID NO 78
<211> LENGTH: 112
<212> TYPE: PRT
<213> ORGANISM: Artificial
<220> FEATURE:
<223> OTHER INFORMATION: an artificially synthesized sequence

<400> SEQUENCE: 78

```
Asp Val Val Met Thr Gln Ser Pro Leu Ser Leu Pro Val Thr Leu Gly
1               5                   10                  15

Gln Pro Ala Ser Ile Ser Cys Arg Ser Ser Arg Asn Ile Val His Thr
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Leu Glu Ile Lys
                100                 105                 110
```

<210> SEQ ID NO 79
<211> LENGTH: 112
<212> TYPE: PRT
<213> ORGANISM: Artificial
<220> FEATURE:
<223> OTHER INFORMATION: an artificially synthesized sequence

<400> SEQUENCE: 79

```
Asp Val Val Met Thr Gln Ser Pro Leu Ser Leu Pro Val Thr Leu Gly
1               5                   10                  15

Arg Pro Ala Ser Ile Ser Cys Arg Ser Ser Arg Asn Ile Val His Thr
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Leu Glu Ile Lys
            100                 105                 110

<210> SEQ ID NO 80
<211> LENGTH: 112
<212> TYPE: PRT
<213> ORGANISM: Artificial
<220> FEATURE:
<223> OTHER INFORMATION: an artificially synthesized sequence

<400> SEQUENCE: 80

Asp Val Val Met Thr Gln Ser Pro Leu Ser Leu Pro Val Thr Leu Gly
 1               5                  10                  15

Gln Pro Ala Ser Ile Ser Cys Arg Ser Ser Arg Asn Ile Val His Thr
                 20                  25                  30

Asn Gly Asn Thr Tyr Leu Glu Trp Tyr Gln Gln Lys Pro Gly Lys Ala
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Arg Gly Thr Lys Leu Glu Ile Lys
            100                 105                 110

<210> SEQ ID NO 81
<211> LENGTH: 112
<212> TYPE: PRT
<213> ORGANISM: Artificial
<220> FEATURE:
<223> OTHER INFORMATION: an artificially synthesized sequence

<400> SEQUENCE: 81

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Asn Ile Val His Thr
                 20                  25                  30

Asn Ala Asn Thr Tyr Leu Glu Trp Tyr Gln Gln Lys Pro Gly Lys Ala
             35                  40                  45

Pro Glu Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Phe Thr Phe Gly Gln Gly Thr Lys Leu Glu Ile Lys
            100                 105                 110

<210> SEQ ID NO 82
<211> LENGTH: 112
<212> TYPE: PRT
<213> ORGANISM: Artificial
<220> FEATURE:
<223> OTHER INFORMATION: an artificially synthesized sequence
```

<400> SEQUENCE: 82

Asp Val Val Met Thr Gln Ser Pro Leu Ser Leu Pro Val Thr Leu Gly
1               5                   10                  15

Arg Pro Ala Ser Ile Ser Cys Arg Ser Ser Arg Asn Ile Val His Thr
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Arg Gly Thr Lys Leu Glu Ile Lys
            100                 105                 110

<210> SEQ ID NO 83
<211> LENGTH: 112
<212> TYPE: PRT
<213> ORGANISM: Artificial
<220> FEATURE:
<223> OTHER INFORMATION: an artificially synthesized sequence

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Gln Ser Ser Gln Asn Ile Val His Thr
            20                  25                  30

Asn Ala Asn Thr Tyr Leu Glu Trp Tyr Gln Gln Lys Pro Gly Lys Ala
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Phe Thr Phe Gly Gln Gly Thr Lys Val Glu Ile Glu
            100                 105                 110

<210> SEQ ID NO 84
<211> LENGTH: 16
<212> TYPE: PRT
<213> ORGANISM: Artificial
<220> FEATURE:
<223> OTHER INFORMATION: an artificially synthesized sequence

<400> SEQUENCE: 84

Arg Ser Ser Gln Asn Ile Val His Thr Asn Gly Asn Thr Tyr Leu Glu
1               5                   10                  15

<210> SEQ ID NO 85
<211> LENGTH: 16
<212> TYPE: PRT
<213> ORGANISM: Artificial
<220> FEATURE:
<223> OTHER INFORMATION: an artificially synthesized sequence

<400> SEQUENCE: 85

Gln Ser Ser Gln Asn Ile Val His Thr Asn Gly Asn Thr Tyr Leu Glu

```
<210> SEQ ID NO 86
<211> LENGTH: 16
<212> TYPE: PRT
<213> ORGANISM: Artificial
<220> FEATURE:
<223> OTHER INFORMATION: an artificially synthesized sequence

<400> SEQUENCE: 86

Gln Ser Ser Glu Asn Ile Val His Thr Asn Gly Asn Thr Tyr Leu Glu
 1               5                  10                  15

<210> SEQ ID NO 87
<211> LENGTH: 16
<212> TYPE: PRT
<213> ORGANISM: Artificial
<220> FEATURE:
<223> OTHER INFORMATION: an artificially synthesized sequence

<400> SEQUENCE: 87

Arg Ser Ser Arg Asn Ile Val His Thr Asn Gly Asn Thr Tyr Leu Glu
 1               5                  10                  15

<210> SEQ ID NO 88
<211> LENGTH: 16
<212> TYPE: PRT
<213> ORGANISM: Artificial
<220> FEATURE:
<223> OTHER INFORMATION: an artificially synthesized sequence

<400> SEQUENCE: 88

Arg Ser Ser Gln Asn Ile Val His Thr Asn Ala Asn Thr Tyr Leu Glu
 1               5                  10                  15

<210> SEQ ID NO 89
<211> LENGTH: 16
<212> TYPE: PRT
<213> ORGANISM: Artificial
<220> FEATURE:
<223> OTHER INFORMATION: an artificially synthesized sequence

<400> SEQUENCE: 89

Gln Ser Ser Gln Asn Ile Val His Thr Asn Ala Asn Thr Tyr Leu Glu
 1               5                  10                  15

<210> SEQ ID NO 90
<211> LENGTH: 7
<212> TYPE: PRT
<213> ORGANISM: Artificial
<220> FEATURE:
<223> OTHER INFORMATION: an artificially synthesized sequence

<400> SEQUENCE: 90

Lys Val Ser Asn Arg Phe Ser
 1               5

<210> SEQ ID NO 91
<211> LENGTH: 9
<212> TYPE: PRT
<213> ORGANISM: Artificial
<220> FEATURE:
<223> OTHER INFORMATION: an artificially synthesized sequence

<400> SEQUENCE: 91

Phe Gln Gly Ser His Ile Pro Phe Thr
 1               5
```

<210> SEQ ID NO 92
<211> LENGTH: 23
<212> TYPE: PRT
<213> ORGANISM: Artificial
<220> FEATURE:
<223> OTHER INFORMATION: an artificially synthesized sequence

<400> SEQUENCE: 92

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 93
<211> LENGTH: 23
<212> TYPE: PRT
<213> ORGANISM: Artificial
<220> FEATURE:
<223> OTHER INFORMATION: an artificially synthesized sequence

<400> SEQUENCE: 93

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 94
<211> LENGTH: 23
<212> TYPE: PRT
<213> ORGANISM: Artificial
<220> FEATURE:
<223> OTHER INFORMATION: an artificially synthesized sequence

<400> SEQUENCE: 94

Asp Val Val Met Thr Gln Ser Pro Leu Ser Leu Pro Val Thr Leu Gly
1               5                   10                  15

Arg Pro Ala Ser Ile Ser Cys
            20

<210> SEQ ID NO 95
<211> LENGTH: 15
<212> TYPE: PRT
<213> ORGANISM: Artificial
<220> FEATURE:
<223> OTHER INFORMATION: an artificially synthesized sequence

<400> SEQUENCE: 95

Trp Tyr Leu Gln Lys Pro Gly Gln Ser Pro Glu Leu Leu Ile Tyr
1               5                   10                  15

<210> SEQ ID NO 96
<211> LENGTH: 15
<212> TYPE: PRT
<213> ORGANISM: Artificial
<220> FEATURE:
<223> OTHER INFORMATION: an artificially synthesized sequence

<400> SEQUENCE: 96

Trp Tyr Gln Gln Lys Pro Gly Lys Ala Pro Glu Leu Leu Ile Tyr
1               5                   10                  15

<210> SEQ ID NO 97
<211> LENGTH: 15
<212> TYPE: PRT

```
<213> ORGANISM: Artificial
<220> FEATURE:
<223> OTHER INFORMATION: an artificially synthesized sequence

<400> SEQUENCE: 97

Trp Tyr Gln Gln Lys Pro Gly Glu Ala Pro Glu Leu Leu Ile Tyr
1               5                   10                  15

<210> SEQ ID NO 98
<211> LENGTH: 15
<212> TYPE: PRT
<213> ORGANISM: Artificial
<220> FEATURE:
<223> OTHER INFORMATION: an artificially synthesized sequence

<400> SEQUENCE: 98

Trp Tyr Gln Gln Lys Pro Gly Gln Ala Pro Glu Leu Leu Ile Tyr
1               5                   10                  15

<210> SEQ ID NO 99
<211> LENGTH: 15
<212> TYPE: PRT
<213> ORGANISM: Artificial
<220> FEATURE:
<223> OTHER INFORMATION: an artificially synthesized sequence

<400> SEQUENCE: 99

Trp Tyr Gln Gln Lys Pro Gly Lys Ala Pro Lys Leu Leu Ile Tyr
1               5                   10                  15

<210> SEQ ID NO 100
<211> LENGTH: 32
<212> TYPE: PRT
<213> ORGANISM: Artificial
<220> FEATURE:
<223> OTHER INFORMATION: an artificially synthesized sequence

<400> SEQUENCE: 100

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 101
<211> LENGTH: 32
<212> TYPE: PRT
<213> ORGANISM: Artificial
<220> FEATURE:
<223> OTHER INFORMATION: an artificially synthesized sequence

<400> SEQUENCE: 101

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 102
<211> LENGTH: 10
<212> TYPE: PRT
<213> ORGANISM: Artificial
<220> FEATURE:
<223> OTHER INFORMATION: an artificially synthesized sequence

<400> SEQUENCE: 102

Phe Gly Thr Gly Thr Lys Leu Glu Ile Lys
1               5                   10
```

<210> SEQ ID NO 103
<211> LENGTH: 10
<212> TYPE: PRT
<213> ORGANISM: Artificial
<220> FEATURE:
<223> OTHER INFORMATION: an artificially synthesized sequence

<400> SEQUENCE: 103

Phe Gly Gln Gly Thr Lys Leu Glu Ile Lys
1               5                   10

<210> SEQ ID NO 104
<211> LENGTH: 10
<212> TYPE: PRT
<213> ORGANISM: Artificial
<220> FEATURE:
<223> OTHER INFORMATION: an artificially synthesized sequence

<400> SEQUENCE: 104

Phe Gly Gln Gly Thr Lys Val Glu Ile Glu
1               5                   10

<210> SEQ ID NO 105
<211> LENGTH: 10
<212> TYPE: PRT
<213> ORGANISM: Artificial
<220> FEATURE:
<223> OTHER INFORMATION: an artificially synthesized sequence

<400> SEQUENCE: 105

Phe Gly Arg Gly Thr Lys Leu Glu Ile Lys
1               5                   10

<210> SEQ ID NO 106
<211> LENGTH: 328
<212> TYPE: PRT
<213> ORGANISM: Artificial
<220> FEATURE:
<223> OTHER INFORMATION: an artificially synthesized sequence

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

-continued

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 107
<211> LENGTH: 107
<212> TYPE: PRT
<213> ORGANISM: Homo sapiens

<400> SEQUENCE: 107

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 108
<211> LENGTH: 119
<212> TYPE: PRT
<213> ORGANISM: Artificial
<220> FEATURE:
<223> OTHER INFORMATION: an artificially synthesized sequence

<400> SEQUENCE: 108

Gln Val Gln Leu Lys Gln Ser Gly Pro Gly Leu Val Ala Pro Ser Gln
1               5                   10                  15

Ser Leu Ser Ile Thr Cys Thr Val Ser Gly Leu Ser Leu Thr Ser Phe
            20                  25                  30

Gly Val Asp Trp Val Arg Gln Ser Pro Gly Lys Gly Leu Glu Trp Leu
            35                  40                  45

Gly Val Ile Trp Gly Gly Ser Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Gly Ser Lys Tyr Gly Ala Trp Phe Ala Tyr Trp Gly Gln Gly
            100                 105                 110

Thr Leu Val Thr Val Ser Ala
        115

<210> SEQ ID NO 109
<211> LENGTH: 32
<212> TYPE: PRT
<213> ORGANISM: Artificial
<220> FEATURE:
<223> OTHER INFORMATION: an artificially synthesized sequence

<400> SEQUENCE: 109

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 110
<211> LENGTH: 4
<212> TYPE: PRT
<213> ORGANISM: Artificial
<220> FEATURE:
<223> OTHER INFORMATION: an artificially synthesized sequence

<400> SEQUENCE: 110

Gly Gly Gly Ser
1

<210> SEQ ID NO 111
<211> LENGTH: 4
<212> TYPE: PRT
<213> ORGANISM: Artificial
<220> FEATURE:
<223> OTHER INFORMATION: an artificially synthesized sequence

<400> SEQUENCE: 111

Ser Gly Gly Gly
1

<210> SEQ ID NO 112
<211> LENGTH: 5
<212> TYPE: PRT
<213> ORGANISM: Artificial
<220> FEATURE:
<223> OTHER INFORMATION: an artificially synthesized sequence

<400> SEQUENCE: 112

Gly Gly Gly Gly Ser
1               5

<210> SEQ ID NO 113
<211> LENGTH: 5
<212> TYPE: PRT
<213> ORGANISM: Artificial
<220> FEATURE:

```
<223> OTHER INFORMATION: an artificially synthesized sequence

<400> SEQUENCE: 113

Ser Gly Gly Gly Gly
1               5

<210> SEQ ID NO 114
<211> LENGTH: 6
<212> TYPE: PRT
<213> ORGANISM: Artificial
<220> FEATURE:
<223> OTHER INFORMATION: an artificially synthesized sequence

<400> SEQUENCE: 114

Gly Gly Gly Gly Gly Ser
1               5

<210> SEQ ID NO 115
<211> LENGTH: 6
<212> TYPE: PRT
<213> ORGANISM: Artificial
<220> FEATURE:
<223> OTHER INFORMATION: an artificially synthesized sequence

<400> SEQUENCE: 115

Ser Gly Gly Gly Gly Gly
1               5

<210> SEQ ID NO 116
<211> LENGTH: 7
<212> TYPE: PRT
<213> ORGANISM: Artificial
<220> FEATURE:
<223> OTHER INFORMATION: an artificially synthesized sequence

<400> SEQUENCE: 116

Gly Gly Gly Gly Gly Gly Ser
1               5

<210> SEQ ID NO 117
<211> LENGTH: 7
<212> TYPE: PRT
<213> ORGANISM: Artificial
<220> FEATURE:
<223> OTHER INFORMATION: an artificially synthesized sequence

<400> SEQUENCE: 117

Ser Gly Gly Gly Gly Gly Gly
1               5
```